United States Patent [19]

Oshima et al.

[11] Patent Number: 5,302,602
[45] Date of Patent: Apr. 12, 1994

[54] TRICYCLIC THROMBOXANE A₂ ANTAGONISTS

[75] Inventors: Etsuo Oshima, Shizuoka; Hiroyuki Obase, Mishima; Akira Karasawa; Kazuhiro Kubo, both of Shizuoka; Ichiro Miki, Tokyo; Akio Ishii; Hidee Ishii, both of Shizuoka; Kenji Ohmori, Mishima, all of Japan

[73] Assignee: Kyowa Hakko Kogyo Co., Ltd., Tokyo, Japan

[21] Appl. No.: 884,208

[22] Filed: May 18, 1992

Related U.S. Application Data

[62] Division of Ser. No. 616,095, Nov. 20, 1990, Pat. No. 5,143,922, which is a division of Ser. No. 281,545, Dec. 8, 1988, Pat. No. 4,994,463.

[30] Foreign Application Priority Data

Dec. 14, 1987 [JP] Japan .................. 62-315769
Feb. 3, 1988 [JP] Japan .................. 63-23543

[51] Int. Cl.⁵ ............... A61K 31/445; C07D 211/22
[52] U.S. Cl. ................... 514/325; 514/212; 514/424; 514/428; 540/604; 540/609; 540/610; 546/203; 546/204; 548/525
[58] Field of Search ............... 546/203, 204; 548/528; 540/604, 609, 610; 514/325, 212, 424, 428

[56] References Cited

U.S. PATENT DOCUMENTS

| | | | |
|---|---|---|---|
| 3,354,155 | 11/1967 | Tretter | 260/240 |
| 3,420,851 | 1/1969 | Bloom et al. | 260/333 |
| 4,282,365 | 8/1981 | Rokach et al. | 548/252 |
| 4,585,788 | 4/1986 | Helsley et al. | 514/450 |
| 4,596,809 | 6/1986 | Takizawa et al. | 514/25 |
| 4,749,703 | 6/1988 | Uso et al. | 514/253 |
| 4,912,222 | 3/1990 | Griffith et al. | 546/196 |

FOREIGN PATENT DOCUMENTS

| | | |
|---|---|---|
| 0085870 | 8/1983 | European Pat. Off. . |
| 188802 | 7/1986 | European Pat. Off. . |
| 214779 | 3/1987 | European Pat. Off. . |
| 0235796 | 9/1987 | European Pat. Off. . |
| 2407661 | 8/1974 | Fed. Rep. of Germany . |
| 152673 | 7/1986 | Japan . |
| 152674 | 7/1986 | Japan . |
| 152675 | 7/1986 | Japan . |
| 152676 | 7/1986 | Japan . |
| 257981 | 11/1986 | Japan . |
| 153280 | 7/1987 | Japan . |
| 1330966 | 9/1973 | United Kingdom . |
| 1347935 | 2/1974 | United Kingdom . |

OTHER PUBLICATIONS

Arz.—Forsch., 13, 1039 (1963).
Arz.-Forsch., 14, 100 (1964).
J. Med. Chem. 21, 633 (1978).
Chem. Abstracts, vol. 72, 308 (1970) No. 3387d.
Chem. Abstracts, vol. 81, 424 (1974), No. 25566z.
Eur. J. Med. Chem.-Chimica Therapeutica, P. Dostert et al., "Composes Tricycliques portant une chaine alkylaminoalkylthio. Synthese et activite pharmacologique," May-Jun. 1974-9, No. 3, p. 259.
J. Med. Chem., M. Cerelli et al., "Antiinflammatory and Aldose Reductase Inhibitory Activity of Some Tricyclic Arylacetic Acids," vol. 29, 2347 (1986).

Primary Examiner—C. Warren Ivy
Assistant Examiner—James H. Turnipseed
Attorney, Agent, or Firm—Fitzpatrick, Cella, Harper & Scinto

[57] ABSTRACT

Novel tricyclic compounds having a TXA₂ antagonizing activity represented by formula (I):

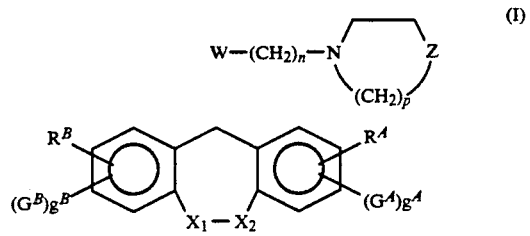

possess a potent antagonizing against thromboxane A₂ and also an antiallergic and/or antihistaminic activity, and are expected to have preventive and therapeutic effects on ischemic diseases, cerebro-vascular diseases, etc.

10 Claims, No Drawings

TRICYCLIC THROMBOXANE A₂ ANTAGONISTS

This application is a division of application Ser. No. 616,095, filed Nov. 20, 1990, now U.S. Pat. No. 5,143,922 which is a division of application Ser. No. 281,545, filed Dec. 8, 1988, now U.S. Pat. No. 4,994,463.

BACKGROUND OF THE INVENTION

The present invention relates to novel tricyclic compounds which strongly antagonize an action of thromboxane A₂ (hereafter referred to as TXA₂) and possess an antiallergic and/or antihistaminic activity.

It is hitherto known that TXA₂ strongly aggregates platelets and is a potent vasoconstrictor [cf. Arachidonic Acid Cascade and Drugs, edited by Shozo Yamamoto, Gendai Iryo Publishing Co., Ltd. (1985)]. Further TXA₂ is a powerful vasoconstrictor against bronchus and bronchial smooth muscle. Therefore, TXA₂is considered to take part in pathological conditions over a wide range. As examples, the following diseases can be exemplified.

(1) Ischemic disease
For example, myocardial infarction, angina pectoris, and thrombosis (2) Cerebro-vascular disease
For example, transient ischemic attack, migraine, cerebral hemorrhage, and cerebral infarction (3) Peripheral vascular diseases and disease caused by unbalanced lipid metabolism
For example, atherosclerosis, capillary convulsion, peripheral circulation disorders, hypertension, and pulmonary embolism (4) Inflammatory and allergic disease
For example, bronchial asthma, bronchitis, pneumonia, nephritis, and hepatitis (5) Shock (6) Cancer metastasis Accordingly, compounds that antagonize the action of TXA₂ are expected to have therapeutic effects in preventing or treating one or more of the diseases described above or other diseases involving TXA₂. Furthermore, in those instances where use of a particular drug was limited due to side effects mediated by TXA₂ or considered to be mediated by TXA₂, it is expected to alleviate the side effects by the use of compounds which antagonize the action of TXA₂.

In recent years, TXA₂ is also thought to play a role in the pathogenesis of allergic diseases, especially of an asthma (cf. J. Allergy Clin. Immunol., 77, 122 (1986); Arch. Pharmacol., 327, 148 (1984)].

As an antagonist of TXA₂, representative compounds are exemplified in Thrombosis Research, 44, 377 (1986).

Furthermore, an indole compound having the following structure:

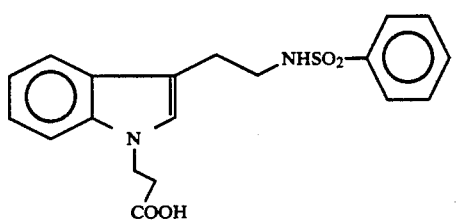

and the like are disclosed in Japanese Published Unexamined Patent Application No. 249960/1986 [West German Patent Application (DE) No. 3,514,696] and a compound having the following structure:

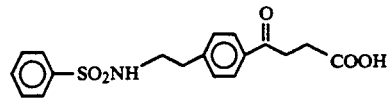

and the like are disclosed in Japanese Publisher Unexamined Patent Application No. 212552/1986 [West German Patent Application (DE) No. 3,508,692]. These compounds have a phenylsulfonamide group as a side chain and exhibit an activity of antagonizing TXA₂.

On the other hand, in tricyclic compounds represented by the following formula:

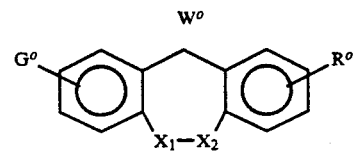

wherein $R^0$ as a substituent on the aromatic ring has carboxyl or a derivative thereof (for example, an ester, an amide, etc.; hereafter collectively referred to as carboxylic acid group) directly or via an alkylene chain, etc. and $W^0$ is hydrogen or a substituent such as oxo (=O), methylene (=CH₂), hydroxyl, alkoxyl, etc., oxepine derivatives wherein $X_1$-$X_2$ is —CH₂O— are known as showing antiinflammatory or antiallergic activities, etc. [J. Med. Chem., 19, 941 (1976); ibid., 20, 1499 (1977); ibid, 21, 633 (1978); U.S. Pat. No. 4,282,365 (Japanese Published Unexamined Patent Application No. 21679/1983); U.S. Pat. No. 4,585,788; Japanese Published Unexamined Patent Application Nos. 152673/1986; 152674/1986 and 152675/1986].

Further, it is also known that oxepine derivatives wherein $R^0$ is hydrogen or a substituent other than the carboxylic acid group, such as, alkyl, alkoxyl, halogen, etc. and $W^0$ has a (di)alkylaminoalkyl chain via —S— show antiasthmatic activities [Japanese Published Unexamined Patent Application No. 126883/1983 (EP 0085870A)]. It is also known that derivatives such as oxepine or thiepine (wherein $X_1$-$X_2$ is —CH₂S—) wherein $W^0$ is alkylaminoalkylidene show an antidepressant action, etc. [U.S. Pat. Nos. 3,354,155 and 3,420,851; Drugs, 13, 161 (1977); Arz.-Forsch., 13, 1039 (1963); ibid., 14, 100 (1964)]. Furthermore, it is also known that derivatives such as cycloheptene (wherein $X_1$-$X_2$ is —CH=CH—) or thiepine wherein $W^0$ has an alkyl chain substituted with an alicyclic nitrogen-containing heterocyclic group such as piperazine, etc. at the terminal thereof via —NHCO— are known to have a calcium antagonizing activity [Japanese Published Unexamined Patent Application Nos. 47466/1986 (EP 191867A) and 153280/1987].

Further oxepine derivatives having an antiallergic activity wherein $R^0$ has a carboxylic acid group and $W^0$ has a (di)alkylaminoalkyl chain via —S— are known [Japanese Published Unexamined Patent Application Nos. 28972/1985 (U.S. Pat. No. 4,596,804); 152669/1986, 152670/1986, 152671/1986 and 15672/1986 (all of them correspond to EP 188802A); 152676/1986 and 257981/1986]. Furthermore, oxepine or cycloheptene (wherein $X_1$-$X_2$ is —CH₂CH₂—) derivatives showing an antihistaminic activity wherein $W^0$ is a (di)alkylaminoalkylidene are known [Japanese Published Unexamined Patent Application No. 45557/1986 (EP 214779A)]. Still further, oxepine derivatives wherein $W^0$ is an alkylidene substituted with an alicyclic nitrogen-containing heterocyclic group such as 4-methylpiperazinyl, 4-methylhomopiperazinyl, piperidino, pyrrolidinyl, thiomorpholino or morpholino or with a (di)alkyl-substituted amino at the terminal thereof are known as showing an antiallergic and antiinflammatory activity [Japanese Published Unexamined Patent Application No. 10784/1988 (EP 0235796A)].

Novel and useful $TXA_2$ antagonists are expected to have preventive and therapeutic effects on various diseases, and are in demand. Further antiallergic agents having a $TXA_2$-antagonizing activity are expected to have preventive and therapeutic effects on allergic diseases, and are in demand.

SUMMARY OF THE INVENTION

An object of the present invention is to provide novel tricyclic compounds having a $TXA_2$- antagonizing activity and antiallergic activity by containing both a carboxylic acid group as the foresaid $R^0$, and, as the aforesaid $W^0$, an alkylthio chain or alkylidene chain substituted at the terminal thereof with an alicyclic nitrogen-containing heterocyclic group having a substituent such as aryl, aralkyl, etc. thereon.

The present invention relates to a tricyclic compound [hereafter referred to as Compound (I); compounds having other formula numbers are also the same] represented by formula (I):

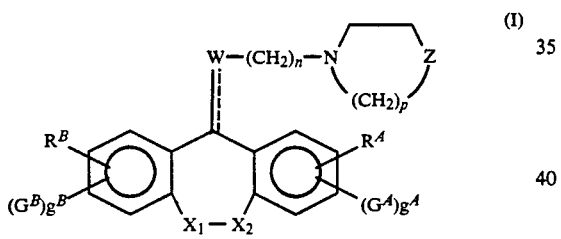

wherein ======= represents single bond or double bond;
$X_1X_2$ represents $-CH_2O-$,

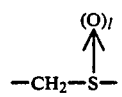

wherein l represents 0, 1 or 2, $-CH_2-CH_2-$, or $-CH=CH-$;
W represents $-S-$ or $=CH-$;
n is 1, 2, 3, or 4;
one of $R^A$ and $R^B$ represents hydrogen and the other represents $-Y-M$ wherein Y represents single bond, $-CR^1R^2-(CH_2)_m-$, or $-CR^1=CR^2-(CH_2)_m-$ wherein each of $R^1$ and $R^2$ independently represents hydrogen or lower alkyl and m is 0, 1, 2, 3 or 4, in which the left side of each formula is bound to the mother nucleus; and M represents $-COOR^3$ wherein $R^3$ represents hydrogen or lower alkyl, $-CONR^{3a}R^{3b}$ wherein each of $R^{3a}$ and $R^{3b}$ independently has the same significances for $R^3$ as described above, or tetrazolyl;

each of $G^A$ and $G^B$ independently represents lower alkyl, halogen, hydroxyl, or lower alkoxyl;
each of $g^A$ and $g^B$ independently represents 0, 1, 2 or 3;
Z represents $>N-E^1-Q$ wherein $E^1$ represents single bond, $-CO-$, $-COO-$ wherein the left side of the formula is bound to the nitrogen atom, or $-SO_2-$; and Q represents optionally substituted aryl, optionally substituted aralkyl, optionally substituted aralkenyl, aromatic heterocyclic group, or

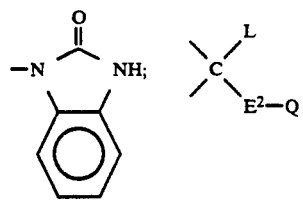

wherein L represents hydrogen, hydroxyl, or lower alkoxy; $E^2$ represents single bond, $-CO-$, or

wherein $R^4$ represents hydrogen or lower alkyl; and Q has the same significance as described above; $>C=CH-Q$ wherein Q has the same significance as described above; or

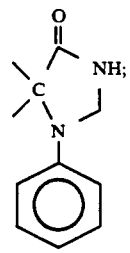

p is 1, 2 or 3;
and a pharmaceutically acceptable salt thereof.

DETAILED DESCRIPTION OF THE INVENTION

In the definition of Z in formula (I), the aryl is exemplified by phenyl and naphthyl having 6 to 10 carbon atoms, etc.; the aralkyl is exemplified by benzyl, phenethyl, benzhydryl and trityl, etc. having 7 to 20 carbon atoms, etc.; and the aralkenyl is exemplified by styryl and cinnamyl having 8 to 18 carbon atoms, etc. The substituent on each group means independently 1 to 3 substituents on the aromatic ring and includes a group selected from lower alkyl, halogen, trifluoromethyl, hydroxyl, lower alkoxyl and methylenedioxy formed together with the ortho-position thereof. Likewise, the aromatic heterocyclic, group shown by Q represents a group selected from furyl, thienyl, pyridyl, pyrimidinyl, quinolyl and isoquinolyl.

Further in the definition of each group in formula (I), the alkyl moiety in the lower alkyl and lower alkoxyl is a straight or branched alkyl having 1 to 6 carbon, atoms, for example, methy, ethyl, propyl, isopropyl, butyl, isobutyl, sec-butyl, tert-butyl, pentyl, neopentyl, hexyl, etc.; the halogen includes, for example, fluorine, chlorine, bromine and iodine.

The pharmaceutically acceptable salt of Compound (I) includes an acid addition salt, a metal salt, an ammonium salt, an organic amine addition salt, an amino acid addition salt, etc. which are pharmaceutically acceptable.

As the pharmaceutically acceptable acid addition salt of Compound (I), mention may be made of the inorganic acid salt such as hydrochloride, sulfate, phosphate, etc. and the organic acid salt such as acetate, malate, fumarate, tartarate, citrate, etc. As the pharmaceutically acceptable metal salt, the alkali metal salt such as sodium salt, potassium salt, etc.; alkaline earth metal salt such as magnesium salt, calcium salt, etc. and further the aluminum salt and the zinc salt are appropriate. As the ammonium salt, mention may be made of the salt of ammonium, tetramethylammonium, etc. As the pharmaceutically acceptable organic amine addition salt, mention may be made of an addition salt of morpholine, piperidine, etc. As the pharmaceutically acceptable amino acid addition salt, an addition salt of lysine, glycine, phenylalanine and the like are mentioned.

Hereafter processes for producing Compound (I) are described but the production of Compound (I) is not deemed to be limited thereto. Further in various processes, the reaction conditions can be appropriately chosen from those described below.

The reaction solvent may be chosen from water or an organic solvent which does not participate in the reaction and can be used alone or in combination. The organic solvent includes, for example, an alcohol such as methanol, ethanol, propanol, isopropanol, etc.; an ether such as diethyl ether, dioxane, tetrahydrofuran, ethylene glycol monomethyl ether, ethylene glycol dimethyl ether, etc.; a hydrocarbon such as benzene, toluene, xylene, hexane, cyclohexane, petroleum ether, ligroin, decalin, etc.; a ketone such as acetone, methyl ethyl ketone, etc., an amide such as formamide, dimethylformamide, hexamethylphosphoric triamide, etc.; acetonitrile, ethyl acetate, dimethylsulfoxide, sulfolane or a halogenated hydrocarbon such as methylene chloride, dichloroethane, tetrachloroethane, chloroform or carbon tetrachloride, etc. Further in case that bases or acids later described are liquid, they may also be used as a solvent.

As the appropriate base, an inorganic or organic base can be used. These bases include an alkali metal hydroxide, for example, lithium hydroxide, sodium hydroxide or potassium hydroxide; an alkali metal carbonate, for example, sodium carbonate, sodium hydrogencarbonate or potassium carbonate; an alkali metal acetate, for example, sodium acetate or potassium acetate; an alkali metal alkoxide, for example, sodium methoxide, sodium ethoxide or potassium tert-butoxide; or an organic metal compound, for example, sodium hydride, n-butyl lithium, sec-butyl lithium; and an organic amine, for example, triethylamine, tri-n-butylamine, pyridine, N,N-dimethylaminopyridine, picoline, lutidine, N,N-dimethylaniline, dicyclohexylmethylamine, N-methylpiperidine, morpholine, diazabicyclooctane, diazabicycloundecene or N7-benzyltrimethylammonium hydroxide (Triton B), etc.

As the appropriate acid, an inorganic or organic acid or Lewis acid can be used. Examples of the inorganic acid include hydrochloric acid, hydrobromic acid, hydroiodic acid, sulfuric acid, nitric acid, hypochloric acid, sulfurous acid or nitrous acid, etc. Examples of the organic acid include formic acid, acetic acid, trifluoroacetic acid, benzoic acid, p-toluenesulfonic acid, camphorsulfonic acid or methanesulfonic acid, etc. Examples of the Lewis acid include aluminum chloride, zinc chloride, tin chloride, boron trifluoride, boron ttifluoride diethyl ether complex, titanium tetrachloride, etc.

The reaction temperature is generally from $-80°$ C. to a boiling point of a solvent. Heating without a solvent is also possible. The reaction may generally be carried out under normal pressure but it is also possible to apply pressure. In this case, the reaction temperature may be raised to a temperature higher than the boiling point of a solvent.

The reaction time is generally in a range of one minute to one week.

In the following description, preferred reaction conditions are given.

Further in the following description, the tricyclic moiety which does not directly participate in the reaction:

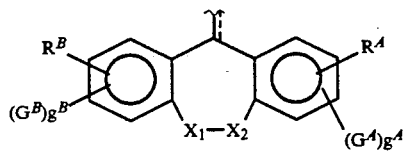

wherein ------,
$X_1-X_2$, $R^A$, $R^B$, $G^A$, $G^B$, $g^A$ and $g^B$ have the same significances as described above; is sometimes referred to as:

Compound (I) can be prepared from Compound (II) or from Compounds (IIIa through d), etc. obtained from Compound (II) according to the following reaction steps:

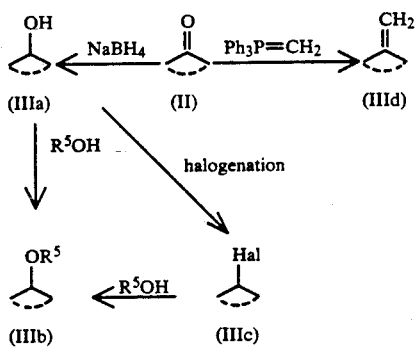

wherein

has the same significance as described above; $R^5$ represents lower alkyl, Hal represents halogen and Ph represents phenyl.

Herein the halogen shown by Hal represents chlorine, bromine and iodine and the lower alkyl has the same significance as defined for the lower alkyl in each group in formula (I).

Compounds (II) are either described in J. Med. Chem., 19, 941 (1976); ibid., 21, 1035 (1978); ibid., 20, 1557 (1977); ibid., 20, 1499 (1977); ibid., 29, 2347 (1986); ibid., 21, 633 (1978); ibid., 20, 456 (1977); U.S. Pat. Nos. 4,172,949 and 4,282,365; Japanese Published Unexamined Patent Application Nos. 21679/1983; 28972/1985; 152669/1986; 152672/1986; 152673/1986; 152675/1986 and 10784/1988 etc. or can be synthesized according to methods described in these publications or in a manner similar thereto.

Moreover Compounds (IIIA to d) can be synthesized from Compound (II) according to methods described in Japanese Published Unexamined Patent Application Nos. 150083/1981; 28972/1985; 152670/1986; 152671/1986; 152672/1986; 152675/1986 and 10784/1988, etc. or in a manner similar thereto.

Method 1-1

[Synthesis of Compound (Ia) in Compound (I), wherein W is —S—(part 1)]

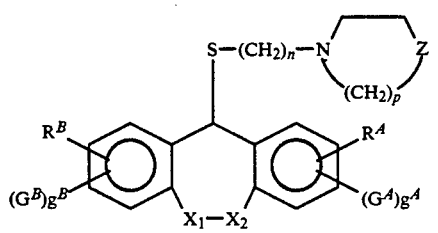

wherein $X_1-X_2$, $R^A$, $R^B$, $G^A$, $G^B$, $Z$, $g^A$, $g^B$, n and p have the same significances as described above.

Compound (Ia) can be obtained from Compounds (IIIA to c) and (IVa) according to the following reaction step.

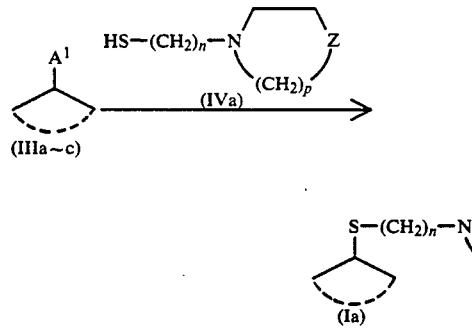

wherein $A^1$ represents OH, $OR^5$ or Hal; and

$Z$, $R^5$, Hal and p have the same significances as described above.

Compound (Ia) or acid addition salts thereof can be obtained by reacting Compound (IIIA) with 1 to 5 molar equivalents of an appropriate dehydration condensing agent, for example, trifluoroacetic anhydride at from 0° C. to room temperature for 1 to 24 hours in an inert solvent such as methylene chloride, chloroform, etc., then adding 1 to 5 molar equivalents of Compound (IVa) or acid addition salts thereof (for example, hydrochloride, hydrobromide, acetate, trifluoroacetate, p-toiuenesulfonate, etc.; theisame is applied hereafter) to the reaction solution and carrying out the reaction at 0° C. to a boiling point of the solvent for 1 to 24 hours, if necessary, in the presence of an appropriate acid catalyst, for example, boron trifluoride diethyl ether complex.

Likewise, Compound (Ia) or acid addition salts thereof can be obtained by reacting Compound (IIIB) with 1 to 5 molar equivalents of Compound (IVa) or acid addition salts thereof in an inert solvent such as methylene chloride, chloroform, etc., at 0° C. to a boiling point of the solvent for 1 to 24 hours, if necessary, in the presence of an appropriate acid catalyst, for example, boron trifluoride diethyl ether complex.

Furthermore, Compound (Ia) or acid addition salts thereof can be obtained by reacting Compound (IIIC) with 1 to 10 molar equivalents of Compound (IVa) or acid addition salts thereof in an inert solvent such as methylene chloride, chloroform, dimethylformamide, etc., at 0° C. to a boiling point of the solvent for 1 to 24 hours, if necessary, in the presence of a base such as triethylamine, sodium hydride, etc.

Method 1-2

[Synthesis of Compound (Ia) (part 2)]

Likewise, Compound (Ia) can be obtained from Compounds (IIIa-c) according to the following reaction steps.

Firstly, Compound (VIb) or (VIc) is prepared from Compounds (IIIa-c) according to the following reaction steps:

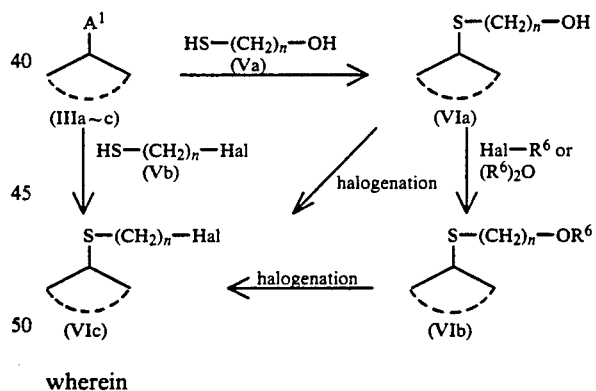

wherein

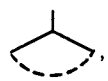

$A^1$, Hal and n have the same significances as described above; and $R^6$ represents a group capable of being split as $OR^6$.

Herein, $R^6$ means, for example, alkylsulfonyl such as methanesulfonyl, trifluoromethanesulfonyl, etc. and arylsulfonyl such as phenylsulfonyl, p-toluenesulfonyl, etc.

The corresponding Compound (VIa) or (VIc) can be obtained by reacting Compound (IIIA) with 1 to 5 molar equivalents of an appropriate dehydrating and condensing agent, for example, trifluoroacetic anhydride, in an inert solvent such as methylene chloride, chloroform, etc., at a temperature of from 0° C. to room temperature for 1 to 24 hours, then adding 1 to 10 molar equivalents of an alcohol (Va) or its halide (Vb) to this reaction solution and carrying out the reaction at a temperature of between room temperature and the boiling point of the solvent, if necessary and desired, in the presence of an appropriate acid catalyst, for example, boron trifluoride diethyl ether complex, for 1 to 24 hours.

Compound (VIa) or (VIc) can also be obtained by reacting Compound (IIIB) or (IIIC) with 1 to 10 molar equivalents of an alcohol (Va) or its halide (Vb) in an inert solvent such as methylene chloride, chloroform, etc., at a temperature of between room temperature and the boiling point of the solvent, if necessary and desired, in the presence of an appropriate acid catalyst, for example, boron trifluoride diethyl ether complex, or an appropriate base such as triethylamine for 1 to 24 hours.

Further, the thus obtained Compound (VIa) may be reacted with 1 to 5 molar equivalents of Hal-$R^6$ or $(R^6)_2O$ (wherein $R^6$ and Hal have the same significances as described above) in an inert solvent such as methylene chloride, chloroform, etc., if necessary and desired, in the presence of a base such as pyridine, etc., at a temperature of from −50° C. to room temperature for 1 to 24 hours to give Compound (VIb).

Furthermore, compound (VIa) may be reacted (1) with 1 to 5 molar equivalents of a halogenating agent, for example, thionyl chloride, in an inert solvent such as methylene chloride, chloroform, etc., if necessary and desired, in the presence of a base such as pyridine, etc., at a temperature of from 0° C. to room temperature for 1 to 24 hours; (2) with 1 to 10 molar equivalents of an alkyl halide such as methyl iodide in an inert solvent such as benzene in the presence of 1 to 10 molar equivalents of triphenylphosphine and 1 to 10 molar equivalents of diethyl azodicarboxylate at a temperature of from −20° C. to a boiling point of the solvent for 1 to 24 hours; or (3) with 1 to 10 molar equivalents of a halogenating agent, for example, methanesulfonyl chloride, in dimethylformamide in the presence of 1 to 10 molar equivalents of a base such as lithium chloride, etc., at a temperature of from −20° to 100° C. for 1 to 24 hours, whereby Compound (VIc) is obtained.

Where Compound (VIc) is the chloride (Hal is Cl) or bromide (Hal is Br), the compound may be reacted further with an iodide, for example, sodium iodide, in a polar solvent such as acetonitrile to give the iodide (Hal is I). Compound (VIb) can be converted into Compound (VIc) under similar conditions.

Compound (VIb) or (VIc) can be converted into Compound (Ia) according to the following reaction step:

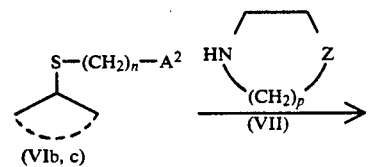

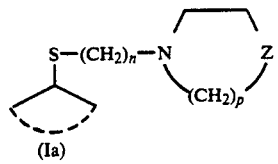

wherein $A^2$ represents $OR^6$ or Hal; and $R^6$, Hal,

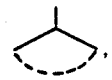

Z, p and n have the same significances as described above.

Compound (Ia) can be obtained by reacting Compound (VIb) or Compound (VIc) with 1 to 10 molar equivalents of Compound (VII), if necessary, in the presence of a molar equivalent to a largely excessive amount of a base such as sodium carbonate, triethylamine, pyridine, Triton B, sodium hydride, etc., at a temperature of between room temperature and the boiling point of the solvent for 1 to 48 hours in an inert solvent such as methylene chloride, chloroform, dichloroethane, dimethylformamide, dioxane, etc.

Further the reaction of Compound (VIc) with Compound (VII) may also be carried out in the presence of an iodide, for example, sodium iodide or potassium iodide.

METHOD 2-1

[Synthesis of Compound (Ib) in Compound (I), wherein W is =CH— (Part 1)]

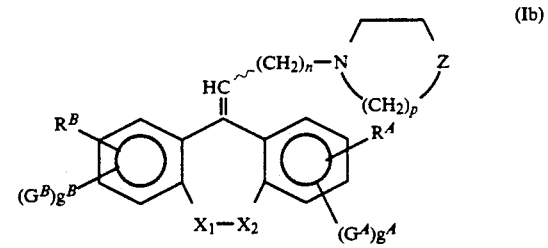

wherein $X_1$-$X_2$, $R^A$, $R^B$, $G^A$, $G^B$, z, n, $g^A$, $g^B$ and p have the same significances as described above.

Compound (Ib) can be prepared according to the following reaction steps:

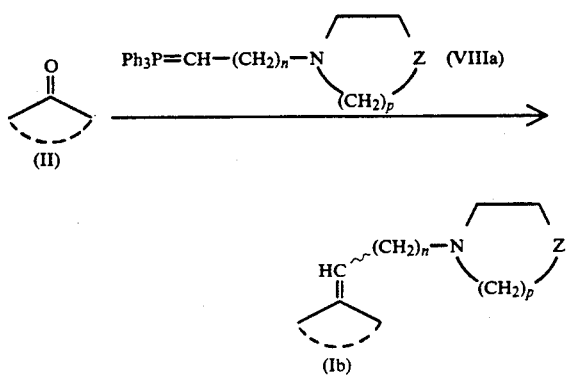

wherein

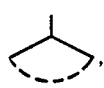

Z, Ph, n and p have the same significances as described above.

Firstly, a phosphonium salt (VIIIb):

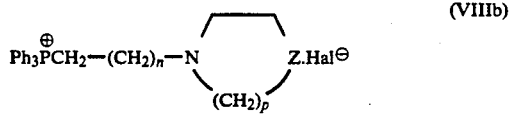

wherein Z, Hal, Ph, n and p have the same significances as described above, obtained by reacting triphenylphosphine (Ph₃P) with a halide:

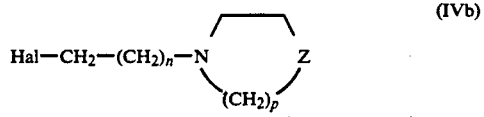

is treated with a molar equivalent of a base such as n-butyl lithium, etc. in an inert solvent, for example, tetrahydrofuran, etc., at 0° C. to room temperature to give an slide (VIIIa).

Compound (Ib) can be obtained by reacting 1 to 5 molar equivalents, based on Compound (II), of Compound (VIIIa), after or without isolation, with Compound (II) in an inert solvent, for example, tetrahydrofuran, etc., at a temperature of from 0° C. and a boiling point of the solvent.

METHOD 2-2

[Synthesis of Compound (Ib) (part 2)]

Compound (Ib) can also be obtained from Compound (II) according to the following reaction steps:

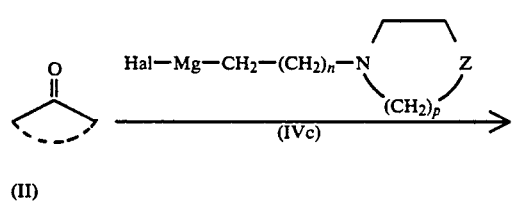

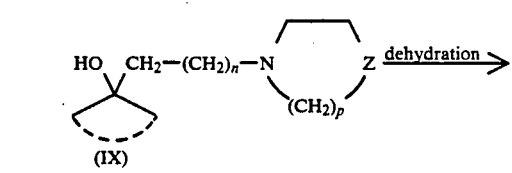

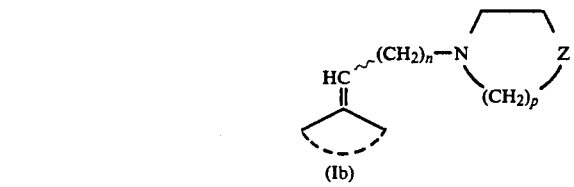

wherein

Z, Hal, n and p have the same significances as described above.

Firstly, Compound (II) is reacted with 1 to 5 molar equivalents of Grignard reagent (IVc) in an inert solvent such as tetrahydrofuran, diethyl ether, etc., at a temperature of from 0° C. to room temperature, for 1 to 48 hours to give an alcohol (IX).

Compound (IVc) can be obtained by reacting corresponding Compound (IVb) with 0.5 to 2 molar equivalents of magnesium in an inert solvent such as tetrahydrofuran, diethyl ether, etc., if necessary and desired, in the presence of a trace amount of iodine, at a temperature of from 0° C. to a boiling point of the solvent for 0.5 to 12 hours. The Grignard reagent thus formed is generally used in the following reaction without isolating the same.

The thus obtained Compound (IX) can be subjected to dehydration to give Compound (Ib). For the dehydration, a method which comprises performing the reaction in an inert solvent such as dioxane, etc., in the presence of an acid, for example, p-toluenesulfonic acid, etc., at a temperature of from room temperature to boiling point of the solvent for 1 to 12 hours, or a method which comprises reacting with a halogenating agent such as thionyl chloride, etc., in an organic base such as pyridine, etc. at a temperature of from 0° C. to a boiling point of the solvent for 1 to 12 hours, or the like is adopted.

METHOD 2-3

[Synthesis of Compound (Ib) (part 3)]

Firstly, the carbonyl group of Compound (II) is converted into Compound (Xb) according to the following reaction steps:

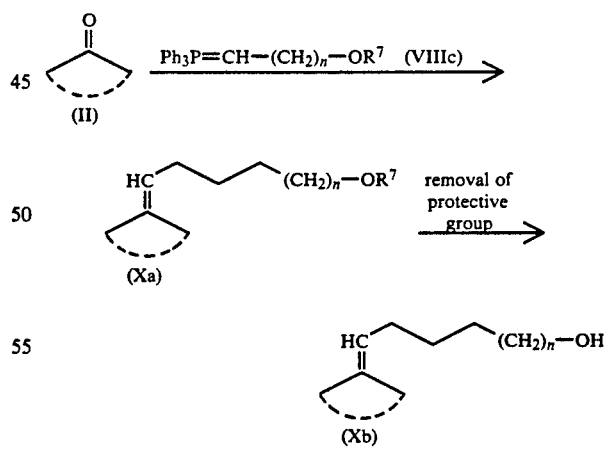

wherein

Ph and n have the same significances as described above, and R⁷ represents a hydroxyl-protecting group.

Herein, as the hydroxyl-protecting group, groups generally use as protective groups for an alcoholic hydroxyl may be used. A preferred protecting group is, for example, tetrahydropyranyl or the like.

Firstly, an ylide (VIIIc) in which hydroxyl is protected by an appropriate protective group (for example, tetrahydropyranyl, etc.) is formed in an inert solvent, for example, tetrahydrofuran [J. Org. Chem., 44, 3760 (1979)].

Then, the formed ylide (VIIIC) is reacted with 0.2 to 1 molar equivalent of Compound (II) at a temperature of from $-78°$ C. to the boiling point of the solvent for 1 to 48 hours to give Compound (Xa).

Compound (Xa) can be converted into Compound (Xb) by removing the protective group. The removal of protective group can be conducted in a conventional manner; in the case of using, for example, tetrahydropyranyl as a protective group, Compound (Xa) is treated with an acid catalyst such as p-toluenesulfonic acid, hydrochloric acid, etc. in a suitable hydrated solvent such as hydrated dioxane, hydrated tetrahydrofuran, etc., at a temperature of from $0°$ C. to a boiling point of the solvent for 1 to 24 hours to give Compound (Xb).

Compound (Xb) can be led to Compound (Ib) via Compound (Xc) or Compound (Xd) by the following reaction steps:

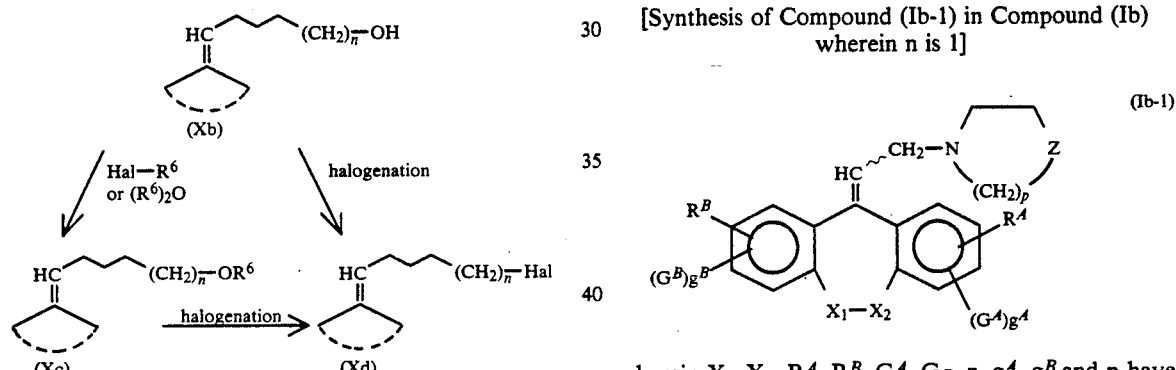

wherein

$Z$, $R^6$, Hal, $n$ and $p$ have the same significances as described above.

The reactions can be preferred in a manner similar to the method for leading from Compound (VIa) to Compound (Ia) described in Method 1-2.

METHOD 2-4

[Synthesis of Compound (Ib-1) in Compound (Ib) wherein $n$ is 1]

wherein $X_1$-$X_2$, $R^A$, $R^B$, $G^A$, $G_B$, $z$, $g^A$, $g^B$ and $p$ have the same significances as described above.

Compound (Ib-1) can be prepared according to the following reaction steps:

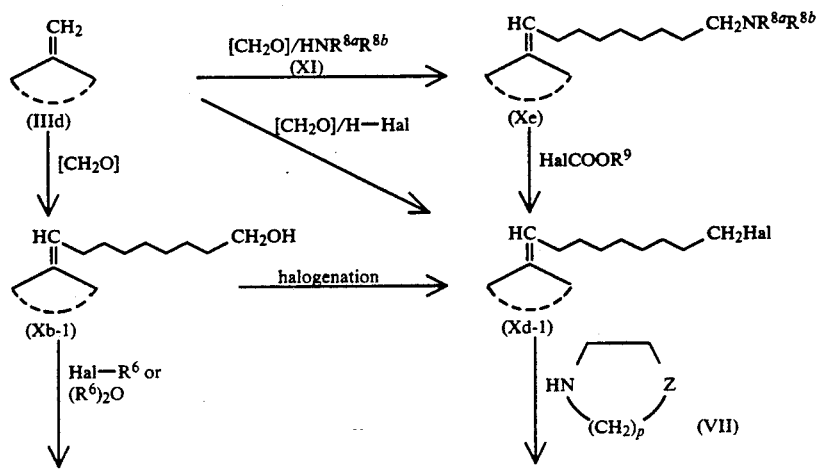

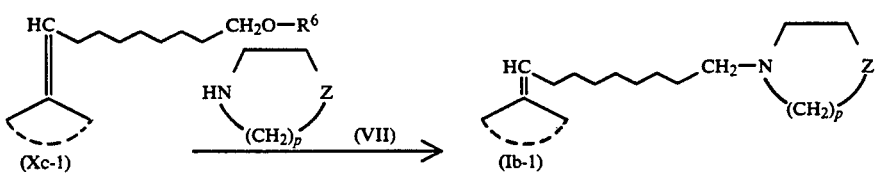

wherein

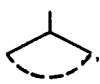

Z, $R^6$, Hal and p have the same significances as described above; [CH$_2$O] represents formaldehyde and/or a polymer thereof; $R^{8a}$ and $R^{8b}$, which may be the same or different, each represents lower alkyl or may be combined to nitrogen adjacent thereto to form a heterocyclic ring and $R^9$ represents lower alkyl.

Herein, the lower alkyl in the definitions of $R^{8a}$, $R^{8b}$ and $R^9$ has the same significance as described for the lower alkyl in formula (I). As the heterocyclic ring formed by $R^{8a}$ and $R^{8b}$, mention may be made of pyrrolidine, piperidine, N-methylpiperazine, morpholine, thiomorpholine, N-methylhomo-piperazine and the like.

Compound (IIID) is reacted with 1 to 10 molar equivalents of formaldehyde and/or a formaldehyde polymer, for example, paraformaldehyde, either in a hydrohalogenic acid, preferably hydrochloric acid or in an inert solvent, for example, dioxane, saturated with hydrogen chloride and, if necessary and desired, in the presence of a strong acid such as sulfuric acid or trifluoroacetic acid, at a temperature of from room temperature to the boiling point of the solvent, for 1 to 24 hours to give Compound (Xd-1).

Further Compound (Xb-1) can be obtained under almost the same conditions as described above except that no hydrohalogenic acid is added.

Furthermore, Compound (Xd-1) can also be obtained as follows. That is, Compound (IIID) is reacted with 1 to 2 molar equivalents of formaldehyde and/or a formaldehyde polymer, for example, paraformaldehyde, and 1 to 3 molar equivalents of a secondary amine (XI) and trifluoroacetic acid, in an inert solvent such as methylene chloride, chloroform, dichloroethane, tetrachloroethane, etc., if necessary and desired, in the presence of acetic acid, at a temperature of from room temperature to the boiling point of the solvent, for 1 to 48 hours to give Compound (Xe) or acid addition salts thereof. Compound (Xe) can be led to Compound (Xd-1) by reacting with 1 to 10 molar equivalents of a halocarbonate, preferably ethyl chloroformate in an inert solvent such as methylene chloride, chloroform, dichloroethane, tetrachloroethane, etc., if necessary, in the presence of a base such as triethyl amine and sodium acetate between at 0° C. and the boiling point of the solvent for 1 to 48 hours.

The thus obtained Compounds (Xb-1) and (Xd-1) can be converted into Compound (Ib-1) as in the synthesis of Compound (Ib) from the corresponding Compounds (Xb) and (Xd) described in Method 2-3.

Further Compound (Ib-1) can also be obtained according to the method for obtaining Compound (Xe) from Compound (IIId) in which Compound (VII) is used in place of Compound (XI).

METHOD 3

[Synthesis of Compound (Ic) in Compound (I), wherein Z is >N—E$^1$—Q]

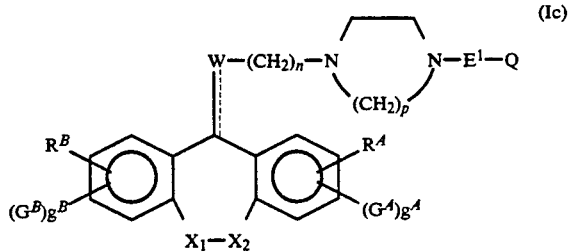

wherein ========, X$_1$-X$_2$, R$^A$, R$^B$, G$^A$, G$^B$, W, E$^1$, Q, g$^A$, g$^B$, n and p have the same significances as described above.

Compound (Ic) can be prepared from Compounds (XII) and (XIII) obtained in a manner similar to Methods 1 and 2 described above by the following reaction steps:

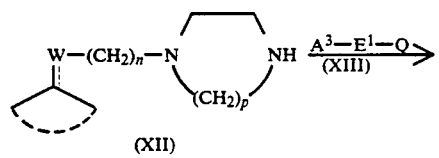

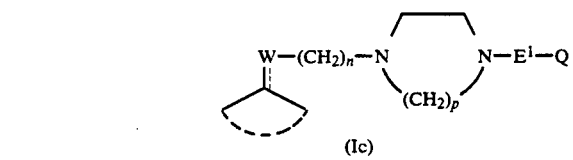

wherein

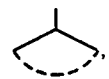

W, E$^1$, Q, n and p have the same significances as described above and A$^3$ represents a leaving group in —E$^1$—Q.

Herein, in the case that E$^1$ is single bond, leaving group A$^3$ represents halogen such as chlorine, bromine, iodine, etc. and in the case that E$^1$ is —CO—, A$^3$— E$^1$—Q represents HOOC—Q (A$^3$ is OH) or a carboxylic acid reactive derivative. The carboxylic acid reactive derivative includes an acid halide (acid chloride, acid bromide, etc.), an acid anhydride (acid anhydride formed with a dehydrating condensing agent such as N,N'-dicyclohexylcarbodiimide, etc., in the reaction system, commercially available acid anhydrides, etc.), an activated ester (p-nitrophenyl ester, N-hydroxysuccinimide ester, etc.), a mixed acid anhydride (monoethyl carbonate, monoisobutyl carbonate, etc.) and the like. Further in the case that $E^1$ is —COO—, $A^3$ represents halogen as described above and in the case that $E^1$ is —SO$_2$—, $A^3$ represents halogen or —O—SO$_2$—Q.

Compound (Ic) can be obtained by reacting Compound (XII) or acid addition salts thereof with 1 to 5 molar equivalents of Compound (XIII), either in an inert solvent such as methylene chloride, chloroform, etc., in the presence of a base such as pyridine, etc., or in a basic organic solvent such as pyridine or triethylamine, etc., at a temperature of 0° C. to room temperature for 1 to 24 hours.

METHOD 4-1

Synthesis of Compound (Id) in Compound (I), wherein M is —COOH]

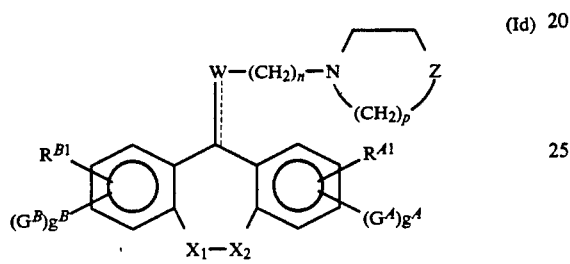

wherein one of $R^{A1}$ and $R^{B1}$ represents —Y—COOH and the other represents hydrogen; and ========, $X_1$-$X_2$, $G^A$, $G^B$, W, Z, Y, n, $g^A$, $g^B$ and p have the same significances as described above.

Compound (Id) can be obtained by hydrolysis of the corresponding carboxylic acid ester.

That is, Compound (Id) can be obtained by subjecting Compound (Ie) [in Compound (I), compound wherein M is —COOR$^{3c}$ (wherein R$^{3c}$ represents lower alkyl in the definitions for R$^3$ described above)] synthesized according to Methods 1 to 3, to an appropriate hydrolysis method, for example, by reacting with a molar equivalent to an excess of sodium hydroxide or potassium hydroxide, etc. in a solvent mixture of a lower alcohol such as methanol, ethanol, etc. and water, at a temperature of from room temperature to the boiling point of the solvent for 1 to 48 hours.

METHOD 4-2

[Synthesis of Compound (Id-1) in Compound (I), wherein Y is single bond]

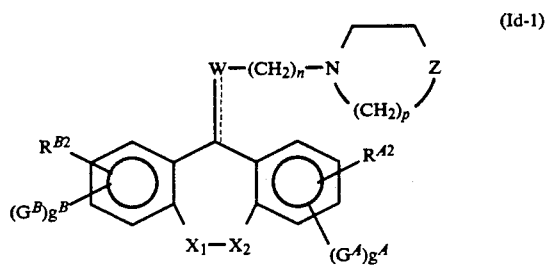

wherein one of $R^{A2}$ and $R^{B2}$ represents —COOH and the other represents hydrogen; and ========, $X_1$-$X_2$, $G^A$, $G^B$, W, Z, n, $g^A$, $g^B$ and p have the same significances as described above.

Compound (Id-1) can be obtained according to the following reaction steps:

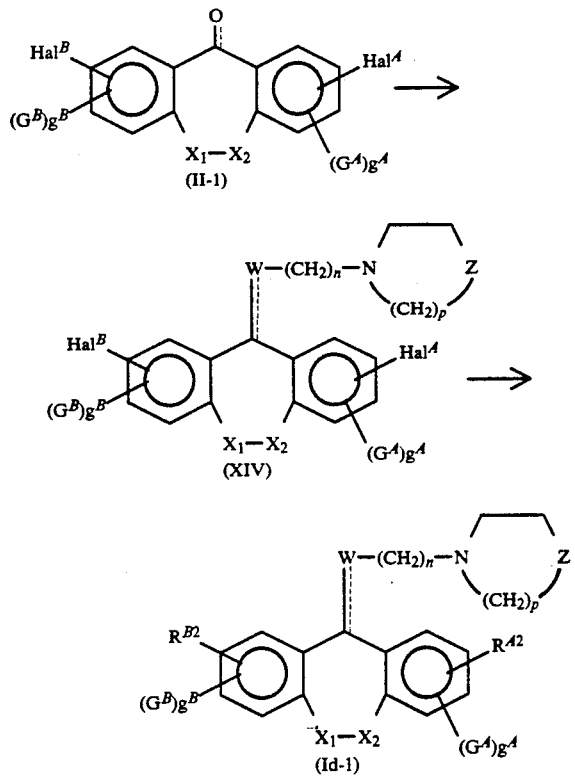

wherein one of Hal$^A$ and Hal$^B$ represents Hal and the other represents hydrogen; and ========, $X_1$-$X_2$, $R_{A2}$, $R^{B2}$, $G^A$, $G^B$, W, Z, Hal, n, $g^A$, $g^B$ and p have the same significances as described above.

Compound (Id-1) can be obtained by carboxylating Compound (XIV) synthesized from Compound (II-1) in a manner similar to Methods 1 to 3.

Carboxylation can be performed by reacting, for example, Compound (XIV) with 1 molar equivalent of a metallizing agent, e.g., n-butyl lithium, in an inert solvent such as tetrahydrofuran, etc., at a temperature of from −78° C. to room temperature, for 10 minutes to 12 hours followed by reacting the resulting reaction mixture with 1 molar equivalent to a largely excessive amount of carbon dioxide at a temperature of from −78° C. to room temperature, for 10 minutes to 12 hours. Alternatively, Compound (Id-1) can be obtained by preparing the corresponding Grignard reagent from Compound (XIV) and magnesium in an inert solvent such as diethyl ether, etc. in a manner similar to Method 2-2 and reacting the reagent with carbon dioxide, and the like method.

METHOD 5

In the methods for production shown by Methods 1 through 4, where groups defined in Compound (I) change under reaction conditions for practicing the method or are inappropriate for practicing the method, the groups may be subjected to conventional means used in organic synthesis chemistry, for example, means for protecting functional groups, means for removing protection, etc. [for example, cf., Green, Protective Groups in Organic Synthesis, John Wiley & Sons Incorporated (1981)], methods for oxidation, reduction, hydrolysis, etc. [for example, cf., SHIN-JIKKEN KAGAKU KOZA, vols. 14 and 15, Maruzen (1977)].

For example, in case that group M is —COOH, 4,4-dimethyloxazoline, etc. are preferably used as a protecting group for —COOH (for example, Japanese Published Unexamined Patent Application No. 10784/1988) in the method in which the corresponding ester is hydrolyzed (cf. Method 4-1 described above) or in the reaction using a Grignard reagent (cf., for example, Method 2-2). Further, a desired compound can be obtained by hydrolyzing (removing a protecting group in) a compound obtained by Methods 1 through 4, etc. in which group —Y—M is —Y'—CH$_2$ $_{OR}$$^{10}$ [wherein Y' represents a group obtained by removing CH$_2$ from Y and R$^{10}$ represents a protecting group for hydroxyl (e.g., acetyl, tetrahydropyranyl, etc.)] to convert into —Y'—CH$_2$OH and oxidizing the compound.

The intermediates and objective compounds in the respective methods described above can be isolated and purified by purification methods conventionally used in organic synthesis chemistry, for example, filtration, extraction, washing, drying, concentration, recrystallization, various column chromatographies, etc. Further the intermediates may also be provided in the subsequent reaction, without being particularly purified.

In Compound (I) obtained by the foregoing methods, compounds wherein W is shown by =CH— include geometrical isomers of E-form and Z-form with respect to stereochemistry. In general, the methods described above give a mixture of these isomers. Isolation and purification of these isomers can be made in a conventional manner in organic synthesis chemistry, for example, column chromatography, recrystallization, etc. It is also possible to isolate the isomers at stages of intermediates (Xa to Xe) by the various methods described above.

Further, if desired, E- and Z-forms may be isomerized from each other. This can be made by treating each isomer under reflux in, e.g., acetic acid, for 1 to 24 hours, in the presence of an appropriate acid catalyst such as p-toluenesulfonic acid, etc.

In the present invention, Compound (I) includes not only the E/Z isomers described above but also all possible stereoisomers and a mixture thereof.

When the synthesis yields Compound (I) in the form of a salt and such salt is a desired product, the thus formed compound (I) may be purified as is.

When Compound (I) is obtained in a free form, salts may be formed in a conventional manner. Furthermore, Compound (I) and pharmaceutically acceptable salts thereof may also be present in the form of addition products to water or various solvents; these adducts including the pharmaceutically acceptable salts are also included in the present invention.

Specific examples of Compound (I) obtained by various methods are shown in Table 1.

Numbering of substitution positions in Table 1 and Table 6 later described does not necessarily harmonize with the correct nomenclature [cf. see (NOTE) below]; but for purpose of simplicity, numbering of the substitution positions is systematically made as illustrated below.

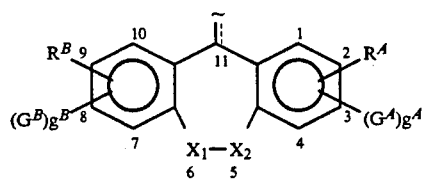

(NOTE)

In cycloheptene derivatives (wherein X$_1$-X$_2$ is —CH$_2$CH$_2$— or —CH=CH—), despite the positional number in the general formula above, for example, a substituent on the carbon at the 2-position in the formula above is correctly given as a substituent at the 3-position. However, in the tables, according to the positional numbering in the formula described above, —COOH on the carbon at the 2-position is indicated to be 2-COOH (correctly 3-COOH).

TABLE 1

| X$_1$—X$_2$ | =W—(CH$_2$)$_n$—N⟨(CH$_2$)$_p$⟩Z | R$^A$/R$^B$ | Compound No. |
|---|---|---|---|
| —CH$_2$O— | —S∼N⟨N—Q⟩ (Q = —⟨phenyl⟩) | 2-COOCH$_3$<br>2-COOH | 1a<br>1b |
| " | —S∼N⟨N—Q⟩ (Q = —⟨phenyl⟩) | 2-CH$_2$COOCH$_3$<br>2-CH$_2$COOH | 2a<br>2b |

TABLE 1-continued

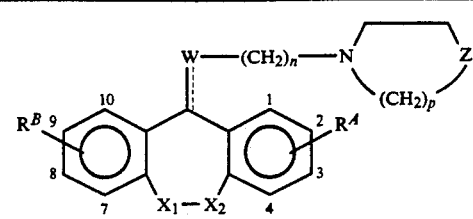

| $X_1-X_2$ | =W-(CH$_2$)$_n$-N<(CH$_2$)$_p$>Z | | $R^A/R^B$ | Compound No. |
|---|---|---|---|---|
| " | -S-CH$_2$CH$_2$-N(piperazine)N-Q | (Q = phenyl) | 2-CH$_2$CH$_2$COOCH$_3$<br>2-CH$_2$CH$_2$COOH | 3a<br>3b |
| " | -S-CH$_2$CH$_2$-N(piperazine)N-Q | (Q = phenyl) | 2-CH(CH$_3$)COOCH$_3$<br>2-CH(CH$_3$)COOH | 4a<br>4b |
| " | -S-CH$_2$CH$_2$-N(piperazine)N-Q | (Q = phenyl) | 2-(tetrazol-5-yl) | 5 |
| " | -S-CH$_2$CH$_2$-N(piperazine)N-Q | (Q = phenyl) | 3-COOCH$_3$<br>3-COOH | 6a<br>6b |
| " | -S-CH$_2$CH$_2$-N(piperazine)N-Q | (Q = phenyl) | 9-COOCH$_3$<br>9-COOH | 7a<br>7b |
| " | -S-CH$_2$CH$_2$-N(piperazine)N-Q | (Q = 4-F-phenyl) | 2-COOCH$_3$<br>2-COOH | 8a<br>8b |
| " | -S-CH$_2$CH$_2$-N(piperazine)N-Q | (Q = 2-OCH$_3$-phenyl) | 2-COOCH$_3$<br>2-COOH | 9a<br>9b |
| -CH$_2$O- | -S-CH$_2$CH$_2$-N(piperazine)N-Q | (Q = 4-OCH$_3$-phenyl) | 2-COOCH$_3$<br>2-COOH | 10a<br>10b |
| " | -S-CH$_2$CH$_2$-N(piperazine)N-Q | (Q = -CH$_2$-phenyl) | 2-COOCH$_3$<br>2-COOH | 11a<br>11b |
| " | -S-CH$_2$CH$_2$-N(piperazine)N-Q | (Q = -CH$_2$-4-Cl-phenyl) | 2-COOCH$_3$<br>2-COOH | 12a<br>12b |

TABLE 1-continued

[Structure: tricyclic system with positions 1-10, X₁-X₂ bridge at bottom, R^A at position 2, R^B at position 9, and =W-(CH₂)n-N(piperazine with (CH₂)p-Z) substituent at top]

| X₁—X₂ | =W—(CH₂)n—N⟨piperazine⟩(CH₂)p—Z | | R^A/R^B | Compound No. |
|---|---|---|---|---|
| " | —S—CH₂CH₂—N(piperazine)N—Q | (Q = —CH₂—C₆H₄—Cl) | 2-C(CH₃)₂COOCH₃<br>2-C(CH₃)₂COOH | 13a<br>13b |
| " | —S—CH₂CH₂—N(piperazine)N—Q | (Q = —CH₂—C₆H₄—OCH₃) | 2-COOCH₃<br>2-COOH | 14a<br>14b |
| " | —S—CH₂CH₂—N(piperazine)N—Q | (Q = —CH₂—C₆H₃(OCH₂O)) | 2-COOCH₃<br>2-COOH | 15a<br>15b |
| " | —S—CH₂CH₂—N(piperazine)N—Q | (Q = —CH(C₆H₅)₂) | 2-COOCH₃<br>2-COOH | 16a<br>16b |
| " | —S—CH₂CH₂—N(piperazine)N—Q | (Q = —CH(4-F-C₆H₄)₂) | 2-COOCH₃<br>2-COOH | 17a<br>17b |
| " | —S—CH₂CH₂—N(piperazine)N—Q | (Q = —C(C₆H₅)₃) | 2-COOCH₃<br>2-COOH | 18a<br>18b |
| " | —S—CH₂CH₂—N(piperazine)N—Q | (Q = —CH₂CH₂—C₆H₅) | 2-COOCH₃<br>2-COOH | 19a<br>19b |
| " | —S—CH₂CH₂—N(piperazine)N—Q | (Q = —CH₂—CH=CH—C₆H₅) | 2-COOCH₃<br>2-COOH | 20a<br>20b |
| —CH₂O— | —S—CH₂CH₂—N(piperazine)NSO₂Q | (Q = —C₆H₅) | 2-COOCH₃<br>2-COOH | 21a<br>21b |

TABLE 1-continued

[Structure shown: dibenzo-fused ring system with positions labeled 1-4 on one ring (with $R^A$ at position 2) and 7-10 on the other ring (with $R^B$ at position 9), connected via $X_1$—$X_2$ bridge at bottom and =W—(CH$_2$)$_n$—N(ring with (CH$_2$)$_p$ and Z) at top]

| $X_1$—$X_2$ | =W—(CH$_2$)$_n$—N⟨(CH$_2$)$_p$⟩Z | | $R^A/R^B$ | Compound No. |
|---|---|---|---|---|
| " | —S—CH$_2$CH$_2$—N⟨piperazine⟩N—SO$_2$Q | (Q = 4-F-C$_6$H$_4$) | 2-COOCH$_3$<br>2-COOH | 22a<br>22b |
| " | —S—CH$_2$CH$_2$—N⟨piperazine⟩N—SO$_2$Q | (Q = 4-CF$_3$-C$_6$H$_4$) | 2-COOCH$_3$<br>2-COOH | 23a<br>23b |
| " | —S—CH$_2$CH$_2$—N⟨piperazine⟩N—SO$_2$Q | (Q = —CH=CH—C$_6$H$_5$) | 2-COOCH$_3$<br>2-COOH | 24a<br>24b |
| " | —S—CH$_2$CH$_2$—N⟨piperazine⟩N—SO$_2$Q | (Q = 2-thienyl) | 2-COOCH$_3$<br>2-COOH | 25a<br>25b |
| " | —S—CH$_2$CH$_2$—N⟨piperazine⟩N—SO$_2$Q | (Q = 3-pyridyl) | 2-COOCH$_3$<br>2-COOH | 26a<br>26b |
| " | —S—CH$_2$CH$_2$—N⟨piperazine⟩N—CO—Q | (Q = 3,4,5-tri-OCH$_3$-C$_6$H$_2$) | 2-COOCH$_3$<br>2-COOH | 27a<br>27b |
| " | —S—CH$_2$CH$_2$—N⟨piperazine⟩N—CO—Q | (Q = —CH=CH—C$_6$H$_5$) | 2-COOCH$_3$<br>2-COOH | 28a<br>28b |
| " | —S—CH$_2$CH$_2$—N⟨piperazine⟩N—CO—Q | (Q = —CH=CH—C$_6$H$_4$—CF$_3$) | 2-COOCH$_3$<br>2-COOH | 29a<br>29b |
| " | —S—CH$_2$CH$_2$—N⟨piperazine⟩N—CO—O—Q | (Q = C$_6$H$_5$) | 2-COOCH$_3$<br>2-COOH | 30a<br>30b |
| " | —S—CH$_2$CH$_2$—N⟨piperazine⟩N—CO—O—Q | (Q = —CH$_2$—C$_6$H$_5$) | 2-COOCH$_3$<br>2-COOH | 31a<br>31b |

TABLE 1-continued

| $X_1-X_2$ | $=W-(CH_2)_n-N\begin{pmatrix}(CH_2)_p\end{pmatrix}Z$ | | $R^A/R^B$ | Compound No. |
|---|---|---|---|---|
| " | −S−CH₂CH₂−N(piperazine)N−Q | (Q = −CH₂−C₆H₅) | 2-COOCH₃<br>2-COOH | 32a<br>32b |
| −CH₂O− | −S−CH₂CH₂−N(piperazine)N−Q | (Q = −CH₂−CH=CH−C₆H₅) | 2-COOCH₃<br>2-COOH | 33a<br>33b |
| " | −S−CH₂CH₂−N(piperazine)NSO₂−Q | (Q = naphthyl) | 2-COOCH₃<br>2-COOH | 34a<br>34b |
| " | −S−CH₂CH₂−N(piperazine)NSO₂−Q | (Q = −CH=CH−C₆H₅) | 2-COOCH₃<br>2-COOH | 35a<br>35b |
| " | −S−CH₂CH₂−N(piperazine)NSO₂−Q | (Q = 2-thienyl) | 2-COOCH₃<br>2-COOH | 36a<br>36b |
| " | −S−CH₂CH₂−N(piperidine)−Q | (Q = −C₆H₅) | 2-COOCH₃<br>2-COOH | 37a<br>37b |
| " | −S−CH₂CH₂−N(piperidine)−Q | (Q = −CH₂−C₆H₅) | 2-COOCH₃<br>2-COOH | 38a<br>38b |
| " | −S−CH₂CH₂−N(piperidine)−Q | (Q = −CH₂−C₆H₅) | 2-CH₂COOCH₃<br>2-CH₂COOH | 39a<br>39b |
| " | −S−CH₂CH₂−N(piperidine)−Q | (Q = −CH₂−C₆H₅) | 2-CH(CH₃)COOCH₃<br>2-CH(CH₃)COOCH₃ | 40a<br>40b |
| " | −S−CH₂CH₂−N(piperidine)−Q | (Q = −CH₂−C₆H₅) | 2-C(CH₃)₂COOCH₃<br>2-C(CH₃)₂COOH | 41a<br>41b |

TABLE 1-continued

| $X_1-X_2$ | $=W-(CH_2)_n-N\begin{pmatrix}(CH_2)_p\\Z\end{pmatrix}$ | | $R^A/R^B$ | Compound No. |
|---|---|---|---|---|
| " | —S—CH₂CH₂—N⟨piperidine⟩—Q | (Q = —CH₂—C₆H₅) | 2-CH₂CH₂COOCH₃<br>2-CH₂CH₂COOH | 42a<br>42b |
| " | —S—CH₂CH₂—N⟨piperidine⟩—Q | (Q = —CH₂—C₆H₄—Cl) | 2-COOCH₃<br>2-COOH | 43a<br>43b |
| " | —S—CH₂CH₂—N⟨piperidine⟩—Q | (Q = —CH₂—C₆H₄—Cl) | 2-C(CH₃)₂COOCH₃<br>2-C(CH₃)₂COOH | 44a<br>44b |
| —CH₂O— | —S—CH₂CH₂—N⟨piperidine⟩—Q | (Q = —CH₂CH₂—C₆H₅) | 2-COOCH₃<br>2-COOH | 45a<br>45b |
| " | —S—CH₂CH₂—N⟨piperidine⟩—Q | (Q = —CH=CH—C₆H₅) | 2-COOCH₃<br>2-COOH | 46a<br>46b |
| " | —S—CH₂CH₂—N⟨piperidine⟩—Q | (Q = —N⟨benzimidazolone⟩NH) | 2-COOCH₃<br>2-COOH | 47a<br>47b |
| " | —S—CH₂CH₂—N⟨piperidine⟩—Q | (Q = —N⟨benzimidazolone⟩NH) | 2-CH₂COOCH₃<br>2-CH₂COOH | 48a<br>48b |
| " | —S—CH₂CH₂—N⟨piperidine⟩—Q | (Q = —N⟨benzimidazolone⟩NH) | 2-C(CH₃)₂COOCH₃<br>2-C(CH₃)₂COOH | 49a<br>49b |
| " | —S—CH₂CH₂—N⟨piperidine, 4-OH⟩—Q | (Q = —C₆H₅) | 2-COOCH₃<br>2-COOH | 50a<br>50b |

5,302,602

TABLE 1-continued

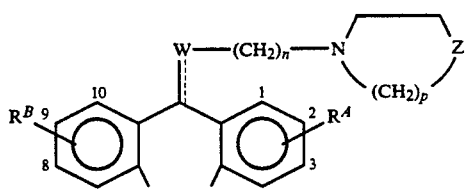

| $X_1-X_2$ | $=W-(CH_2)_n-N\underset{(CH_2)_p}{\overset{}{\subset}}Z$ | | $R^A/R^B$ | Compound No. |
|---|---|---|---|---|
| " | 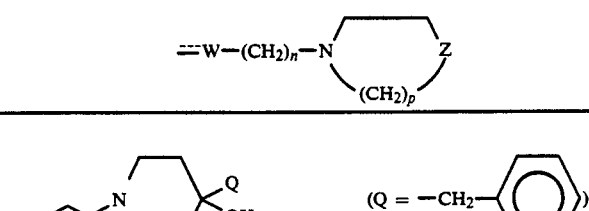 | (Q = —CH$_2$—Ph) | 2-COOCH$_3$<br>2-COOH | 51a<br>51b |
| " | 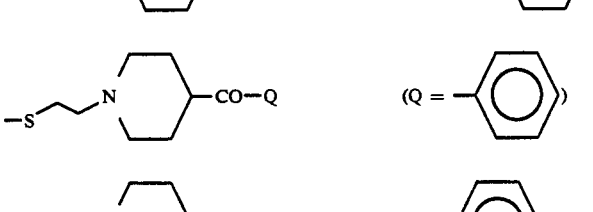 | (Q = Ph) | 2-COOCH$_3$<br>2-COOH | 52a<br>52b |
| " | 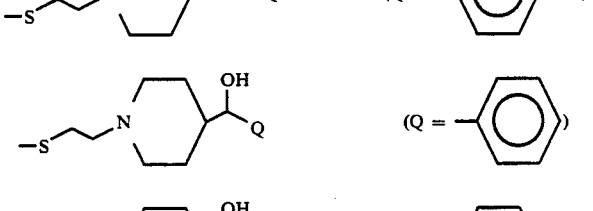 | (Q = —C$_6$H$_4$—Cl) | 2-COOCH$_3$<br>2-COOH | 53a<br>53b |
| " | 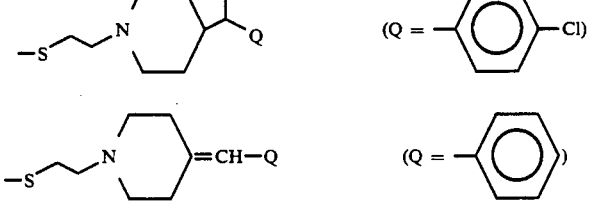 | (Q = Ph) | 2-COOCH$_3$<br>2-COOH | 54a<br>54b |
| " | 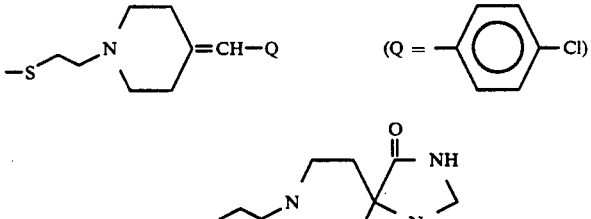 | (Q = —C$_6$H$_4$—Cl) | 2-COOCH$_3$<br>2-COOH | 55a<br>55b |
| " | 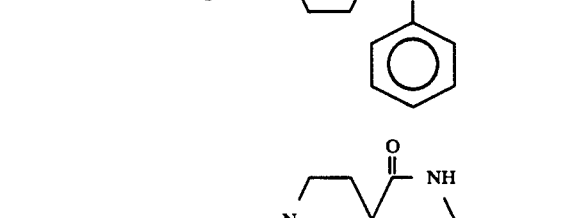 | (Q = Ph) | 2-COOCH$_3$<br>2-COOH | 56a<br>56b |
| —CH$_2$O— | 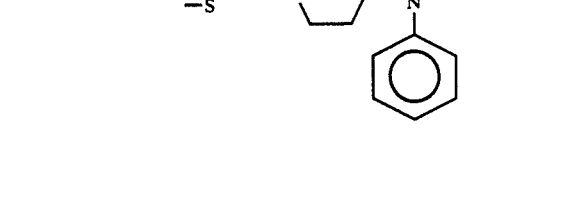 | (Q = —C$_6$H$_4$—Cl) | 2-COOCH$_3$<br>2-COOH | 57a<br>57b |
| " | 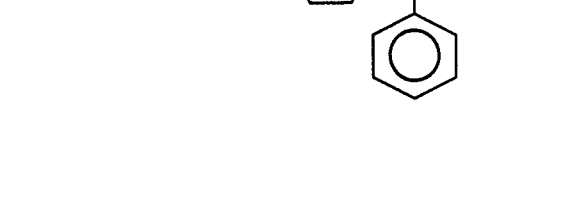 | | 2-COOCH$_3$<br>2-COOH | 58a<br>58b |
| " |  | | 2-C(CH$_3$)$_2$COOCH$_3$<br>2-C(CH$_3$)$_2$COOH | 59a<br>59b |

TABLE 1-continued

| $X_1-X_2$ | =W—(CH$_2$)$_n$—N (piperazine) Z / (CH$_2$)$_p$ | | $R^A/R^B$ | Compound No. |
|---|---|---|---|---|
| " | =CH—CH$_2$—N(piperazine)N—Q | (Q = phenyl) | 2-COOCH$_3$<br>2-COOH | 60a<br>60b |
| " | =CH—CH$_2$—N(piperazine)N—Q | (Q = phenyl) | 2-CH$_2$COOCH$_3$<br>2-CH$_2$COOH | 61a<br>61b |
| " | =CH—CH$_2$—N(piperazine)N—Q | (Q = —CH$_2$—phenyl) | 2-COOCH$_3$<br>2-COOH | 62a<br>62b |
| " | =CH—CH$_2$—N(piperazine)N—Q | (Q = —CH$_2$—phenyl) | 2-CH$_2$COOCH$_3$<br>2-CH$_2$COOH | 63a<br>63b |
| " | =CH—CH$_2$—N(piperazine)N—Q | (Q = —CH$_2$—phenyl) | 2-C(CH$_3$)$_2$COOCH$_3$<br>2-C(CH$_3$)$_2$COOH | 64a<br>64b |
| " | =CH—CH$_2$—N(piperazine)N—Q | (Q = —CH$_2$—C$_6$H$_4$—Cl) | 2-COOCH$_3$<br>2-COOH | 65a<br>65b |
| " | =CH—CH$_2$—N(piperazine)N—Q | (Q = —CH$_2$—C$_6$H$_4$—Cl) | 2-C(CH$_3$)$_2$COOCH$_3$<br>2-C(CH$_3$)$_2$COOH | 66a<br>66b |
| " | =CH—CH$_2$—N(piperazine)N—Q | (Q = —CH$_2$—C$_6$H$_4$—OCH$_3$) | 2-COOCH$_3$<br>2-COOH | 67a<br>67b |
| —CH$_2$O— | =CH—CH$_2$—N(piperazine)N—Q | (Q = —CH$_2$—CH=CH—phenyl) | 2-COOCH$_3$<br>2-COOH | 68a<br>68b |
| " | =CH—CH$_2$—N(piperazine)NSO$_2$—Q | (Q = phenyl) | 2-COOCH$_3$<br>2-COOH | 69a<br>69b |
| " | =CH—CH$_2$—N(piperazine)NSO$_2$—Q | (Q = —C$_6$H$_4$—F) | 2-COOCH$_3$<br>2-COOH | 70a<br>70b |

TABLE 1-continued

| X₁—X₂ | =W—(CH₂)ₙ—N(piperazine)Z / (CH₂)ₚ | Q group | $R^A/R^B$ | Compound No. |
|---|---|---|---|---|
| " | =CH−CH₂−N(piperazine)−NSO₂−Q | (Q = 2-thienyl) | 2-COOCH₃<br>2-COOH | 71a<br>71b |
| " | =CH−N(piperazine)−N−Q | (Q = phenyl) | 2-COOCH₃<br>2-COOH | 72a<br>72b |
| " | =CH−N(piperazine)−N−Q | (Q = 4-F-phenyl) | 2-COOCH₃<br>2-COOH | 73a<br>73b |
| " | =CH−N(piperazine)−N−Q | (Q = −CH₂−phenyl) | 2-COOCH₃<br>2-COOH | 74a<br>74b |
| " | =CH−N(piperazine)−N−Q | (Q = −CH₂−CH=CH−phenyl) | 2-COOCH₃<br>2-COOH | 75a<br>75b |
| " | =CH−N(piperazine)−N−Q | (Q = pyrimidin-2-yl) | 2-COOCH₃<br>2-COOH | 76a<br>76b |
| " | =CH−N(piperazine)−NSO₂−Q | (Q = 4-F-phenyl) | 2-COOCH₃<br>2-COOH | 77a<br>77b |
| " | =CH−N(piperazine)−NSO₂−Q | (Q = −CH=CH−phenyl) | 2-COOCH₃<br>2-COOH | 78a<br>78b |
| " | =CH−N(piperazine)−NSO₂−Q | (Q = 2-thienyl) | 2-COOCH₃<br>2-COOH | 79a<br>79b |
| −CH₂O− | =CH−N(piperazine)−NSO₂−Q | (Q = 2-thienyl) | 2-CH₂COOCH₃<br>2-CH₂COOH | 80a<br>80b |
| " | =CH−N(piperazine)−NSO₂−Q | (Q = 2-thienyl) | 2-CH(CH₃)COOCH₃<br>2-CH(CH₃)COOH | 81a<br>81b |

TABLE 1-continued

| $X_1-X_2$ | $=W-(CH_2)_n-N\begin{pmatrix}(CH_2)_p\end{pmatrix}Z$ | | $R^A/R^B$ | Compound No. |
|---|---|---|---|---|
| " | =CH—N(piperazine)NSO₂—Q | (Q = thiophene-S) | 2-C(CH₃)₂COOCH₃<br>2-C(CH₃)₂COOH | 82a<br>82b |
| " | =CH—CH₂—N(piperazine)NSO₂—Q | (Q = thiophene-S) | 2-CH₂CH₂COOCH₃<br>2-CH₂CH₂COOH | 83a<br>83b |
| " | =CH—CH₂—N(piperidine)Q | (Q = phenyl) | 2-COOCH₃<br>2-COOH | 84a<br>84b |
| " | =CH—CH₂—N(piperidine)Q | (Q = —CH₂—phenyl) | 2-COOCH₃<br>2-COOH | 85a<br>85b |
| " | =CH—CH₂—N(piperidine)Q | (Q = —CH₂—phenyl) | 2-CH₂COOCH₃<br>2-CH₂COOH | 86a<br>86b |
| " | =CH—CH₂—N(piperidine)Q | (Q = —CH₂—phenyl) | 2-CH(CH₃)COOCH₃<br>2-CH(CH₃)COOH | 87a<br>87b |
| " | =CH—CH₂—N(piperidine)Q | (Q = —CH₂—phenyl) | 2-C(CH₃)₂COOCH₃<br>2-C(CH₃)₂COOH | 88a<br>88b |
| " | =CH—CH₂—N(piperidine)Q | (Q = —CH₂—phenyl) | 2-CH₂CH₂COOCH₃<br>2-CH₂CH₂COOH | 89a<br>89b |
| " | =CH—CH₂—N(piperidine)Q | (Q = —CH₂—C₆H₄—Cl) | 2-COOCH₃<br>2-COOH | 90a<br>90b |
| " | =CH—CH₂—N(piperidine)Q | (Q = —CH₂—C₆H₄—Cl) | 2-C(CH₃)₂COOCH₃<br>2-C(CH₃)₂COOH | 91a<br>91b |
| " | =CH—CH₂—N(piperidine)Q | (Q = —CH₂—C₆H₄—OCH₃) | 2-COOCH₃<br>2-COOH | 92a<br>92b |

TABLE 1-continued

| $X_1$—$X_2$ | =W—(CH$_2$)$_n$—N⟨(CH$_2$)$_p$⟩Z | | $R^A/R^B$ | Compound No. |
|---|---|---|---|---|
| —CH$_2$O— | =CH—CH$_2$—N⟨piperidine⟩—Q | (Q = —N⟨benzimidazol-2(3H)-one⟩NH) | 2-COOCH$_3$<br>2-COOH | 93a<br>93b |
| " | =CH—N⟨piperidine⟩—Q | (Q = —phenyl) | 2-COOCH$_3$<br>2-COOH | 94a<br>94b |
| " | =CH—N⟨piperidine⟩—Q | (Q = —CH$_2$—phenyl) | 2-COOCH$_3$<br>2-COOH | 95a<br>95b |
| " | =CH—N⟨piperidine⟩—Q | (Q = —CH$_2$—phenyl) | 2-CH$_2$COOCH$_3$<br>2-CH$_2$COOH | 96a<br>96b |
| " | =CH—N⟨piperidine⟩—Q | (Q = —N⟨benzimidazol-2(3H)-one⟩NH) | 2-COOCH$_3$<br>2-COOH | 97a<br>97b |
| " | =CH—N⟨piperidine⟩—Q | (Q = —N⟨benzimidazol-2(3H)-one⟩NH) | 2-CH$_2$COOCH$_3$<br>2-CH$_2$COOH | 98a<br>98b |
| —CH$_2$S— | —S—CH$_2$—CH$_2$—N⟨piperidine⟩—CH$_2$—phenyl | | 2-COOCH$_3$<br>2-COOH | 99a<br>99b |
| " | =CH—CH$_2$—N⟨piperidine⟩—CH$_2$—phenyl | | 2-COOCH$_3$<br>2-COOH | 100a<br>100b |

TABLE 1-continued

| $X_1-X_2$ | =W—(CH₂)ₙ—N(CH₂)ₚ-Z | $R^A/R^B$ | Compound No. |
|---|---|---|---|
| —CH₂CH₂— | —S-CH₂CH₂-N(piperidin-4-yl)-CH₂-phenyl | 2-COOCH₃<br>2-COOH | 101a<br>101b |
| " | =CH-CH₂-N(piperazinyl)-NSO₂-thienyl | 2-COOCH₃<br>2-COOH | 102a<br>102b |
| —CH=CH— | —S-CH₂CH₂-N(piperidin-4-yl)-CH₂-phenyl | 2-COOCH₃<br>2-COOH | 103a<br>103b |
| " | =CH-CH₂-N(piperazinyl)-NSO₂-thienyl | 2-COOCH₃<br>2-COOH | 104a<br>104b |

The thus prepared Compound (I) possesses a potent TXA₂ antagonizing activity and some of them also exhibit an antiallergic activity and/or antihistaminic activity. Preferred examples of Compound (I) are shown in Table 2.

Names of the compounds given in Table 2, reference examples and examples later described are indicated by correct nomenclature.

TABLE 2

| Compound | No. |
|---|---|
| 11-[2-(4-Phenyl-1-piperazinyl)ethyl]thio-6,11-dihydrodibenz[b,e]oxepin-2-carboxylic acid | 1b |
| 11-[2-(4-Phenyl-1-piperazinyl)ethyl]thio-6,11-dihydrodibenz[b,e]oxepin-2-acetic acid | 2b |
| 11-[2-(4-Benzyl-1-piperazinyl)ethyl]thio-6,11-dihydrodibenz[b,e]oxepin-2-carboxylic acid | 11b |
| 11-[2-(4-Chlorobenzyl-1-piperazinyl)ethyl]thio-6,11-dihydrodibenz[b,e]oxepin-2-carboxylic acid | 12b |
| 2-Methyl-2-[11-[2-(4-chlorobenzyl-1-piperazinyl)ethyl]thio-6,11-dihydrodibenz[b,e]oxepin-2-yl]-propionic acid | 13b |
| 11[2-[4-[Bis(4-fluorophenyl)methyl]-1-piperazinyl]-ethyl]thio-6,11-dihydrodibenz[b,e]oxepin-2-carboxylic acid | 17b |
| 11-[2-(4-Benzyl-1-homopiperazinyl)ethyl]thio-6,11-dihydrodibenz[b,e]oxepin-2-carboxylic acid | 32b |
| 11-[2-(4-Phenyl-1-piperidinyl)ethyl]thio-6,11-dihydrodibenz[b,e]oxepin-2-carboxylic acid | 37b |
| 11-[2-(4-Benzyl-1-piperidinyl)ethyl]thio-6,11-dihydrodibenz[b,e]oxepin-2-carboxylic acid | 38b |
| 11-[2-(4-Benzyl-1-piperidinyl)ethyl]thio-6,11-dihydrodibenz[b,e]oxepin-2-acetic acid | 39b |
| 2-Methyl-2-[11-[2-(4-benzyl-1-piperidinyl)-ethyl]thio-6,11-dihydrodibenz[b,e]oxepin-2-yl]-propionic acid | 41b |
| 11-[2-[4-(4-Chlorobenzyl)-1-piperidinyl]ethyl]thio-6,11-dihydrodibenz[b,e]oxepin-2-carboxylic acid | 43b |
| 2-Methyl-2-[11-[2-[4-(4-chlorobenzyl-1-piperidinyl)-ethyl]thio-6,11-dihydrodibenz[b,e]oxepin-2-yl]-propionic acid | 44b |
| 11-[2-[4-[2(3H)-Benzimidazolon-1-yl]piperidino]-ethyl]thio-6,11-dihydrodibenz[b,e]oxepin-2-carboxylic acid | 47b |
| 11-[2-[4-[2(3H)-Benzimidazolon-1-yl]piperidino]-ethyl]thio-6,11-dihydrodibenz[b,e]oxepin-2-acetic acid | 48b |
| 2-Methyl-2-[11-[2-[4-[2(3H)-benzimidazolon-1-yl]-piperidino]ethyl]thio-6,11-dihydrodibenz[b,e]-oxepin-2-carboxylic acid | 49b |
| 11-[2-[1-Phenyl-1,3,8-triazaspiro[4.5]decan-4-on-8-yl]ethyl]thio-6,11-dihydrodibenz[b,e]oxepin-2-carboxylic acid | 58b |
| 2-Methyl-2-[11-[2-[1-phenyl-1,3,8-triazaspiro[4.5]-decan-4-one-8-yl]ethyl]thio-6,11-dihydrodibenz-[b,e]oxepin-2-yl]propionic acid | 59b |
| 11-[3-(4-Benzyl-1-piperazinyl)propylidene]-6,11-dihydrodibenz[b,e]oxepin-2-carboxylic acid | 62b |
| 11-[3-(4-Benzyl-1-piperazinyl)propylidene]-6,11-dihydrodibenz[b,e]oxepin-2-acetic acid | 63b |
| 2-Methyl-2-[11-[3-(4-benzyl-1-piperazinyl)propylidene-6,11-dihydrodibenz[b,e]oxepin-2-yl]propionic acid | 64b |
| 11-[3-[4-(4-Chlorobenzyl)-1-piperazinyl)propylidene]-6,11-dihydrodibenz[b,e]oxepin-2-carboxylic acid | 65b |
| 2-Methyl-2-[11-[3-[4-(4-chlorobenzyl-1-piperazinyl)-propylidene]-6,11-dihydrodibenz[b,e]oxepin-2-yl]-propionic acid | 66b |
| 11-[2-[4-(4-Thienylsulfonyl)-1-piperazinyl]-ethylidene]-6,11-dihydrodibenz[b,e]oxepin-2-carboxylic acid | 79b |
| 11-[2-[4-(2-Thienylsulfonyl)-1-piperazinyl]-ethylidene]-6,11-dihydrodibenz[b,e]oxepin-2-acetic acid | 80b |
| 2-[11-[2-[4-(2-Thienylsulfonyl)-1-piperazinyl]-ethylidene]-6,11-dihydrodibenz[b,e]oxepin-2-yl]- | 81b |

TABLE 2-continued

| Compound | No. |
|---|---|
| propionic acid | |
| 2-Methyl-2-[11-[2-[4-(2-thienylsulfonyl-1-piperazinyl)ethylidene-6,11-dihydrodibenz[b,e]oxepin-2-yl]propionic acid | 82b |
| 3-[11-[2-[4-(2-Thienylsulfonyl)-1-piperazinyl)-ethylidene]-6,11-dihydrodibenz[b,e]oxepin-2-yl]-propionic acid | 83b |
| 11-[3-(4-Phenyl-1-piperidinyl)propylidene]-6,11-dihydrodibenz[b,e]oxepin-2-carboxylic acid | 84b |
| 11-[3-(4-Benzyl-1-piperidinyl)propylidene]-6,11-dihydrodibenz[b,e]oxepin-2-carboxylic acid | 85b |
| 11-[3-(4-Benzyl-1-piperidinyl)propylidene]-6,11-dihydrodibenz[b,e]oxepin-2-acetic acid | 86b |
| 2-Methyl-2-[11-[3-(4-benzyl-1-piperidinyl)-propylidene]-6,11-dihydrodibenz[b,e]oxepin-2-yl]-propionic acid | 88b |
| 11-[3-[4-(4-Chlorobenzyl)-1-piperidinyl]propylidene]-6,11-dihydrodibenz[b,e]oxepin-2-acetic acid | 90b |
| 2-Methyl-2-[11-[3-[4-(4-chlorobenzyl-1-piperidinyl)-propylidene]-6,11-dihydrodibenz[b,e]oxepin-2-yl]-propionic acid | 91b |
| 11-[3-[4-[2(3H)-Benzimidazolon-1-yl]piperidino]-propylidene]-6,11-dihydrodibenz[b,e]oxepin-2-carboxylic acid | 93b |
| 11-[2-[4-[2(3H)-Benzimidazolon-1-yl]piperidino]-ethylidene]-6,11-dihydrodibenz[b,e]oxepin-2-acetic acid | 98b |
| 11-[2-(4-Benzyl-1-piperidinyl)ethyl]thio-6,11-dihydrodibenzo[b,e]thiepin-2-carboxylic acid | 99b |
| 11-[3-(4-Benzyl-1-piperidinyl)propylidene]-6,11-dihydrodibenzo[b,e]thiepin-2-carboxylic acid | 100b |
| 5-[2-(4-Benzyl-1-piperidinyl)ethyl]thio-10,11-dihydro-5H-dibenzo[a,d]cyclohepten-3-carboxylic acid | 101b |
| 5-[2-[4-(2-Thienyl)sulfonyl-1-piperidinyl)ethylidene]-10,11-dihydro-5H-dibenzo[a,d]cyclohepten-3-carboxylic acid | 102b |
| 5-[2-(4-Benzyl-1-piperidinyl)ethyl]thio-5H-dibenzo-[a,d]cyclohepten-3-carboxylic acid | 103b |
| 5-[2-[4-(2-Thienyl)sulfonyl-1-piperidinyl)ethylidene]-5H-dibenzo[a,d]cyclohepten-3-carboxylic acid | 104b |

Next, TXA$_2$ antagonizing activity of Compound (I) is described below.

TEST ON ANTI-PLATELET ACTIVITY (TXA$_2$ ANTAGONIZING TEST)

Using guinea pig platelets influence of the compounds in accordance with the present invention on platelet aggregation induced by U-46619 (9,11-dideoxy-9α,11α-methanoepoxyprostaglandin F$_2$α; manufactured by Cayman Chemica Co., Ltd.) which is a TXA$_2$/prostaglandin H$_2$ receptor stimulant was examined.

Male guinea pig (Hartley strain; body weight, 300 to 600 g) was anesthesized by intraperitoneal administration of sodium pentobarbital (30 mg/kg) and blood was collected from the descending aorta of the abdomen with a 1/10 volume of sodium citrate. By centrifugation (KC-70: manufactured by Kubota Co., Ltd.) at 800 rpm for 10 minutes, platelet rich plasma (PRP) was collected. Platelet aggregation induced by U-46619 (0.5–1 µM) was determined by photometry [Born, G.V.R. et al., Nature (London), 194, 927–929 (1962)]. A test compound was pretreated 3 minutes prior to aggregation induction and ability of inhibiting aggregation was measured. The minimum concentration for inhibiting platelet aggregation by 30% or more was defined as the minimum effective concentration (MEC) of the test compound.

The results are shown in Table 3.

ANTIALLERGIC ACTIVITY TEST

Antiallergic activity was examined in accordance with the passive cutaneous anaphylaxis (PCA) test using rats. As test animals, Wistar strain male rats weighing 180 to 220 g were used to collect antiserum and for the PCA test, Wistar strain male rats weighing 120 to 140 g were used.

A) PREPARATION OF ANTI-EGG WHITE ALBUMIN (EWA) RAT SERUM

Anti-EWA rat serum was prepared according to the method of Stotland and Share [Can. J. Physiol. Pharmacol., 52, 1114 (1974)]. That is, 1 mg of EWA was mixed with 20 mg of aluminum hydroxide gel and 0.5 ml of pertussis-diphtberia-tetanus mixed vaccine. The mixture was subcutaneously administered to the rat paw in 4 portions. Fourteen days after, blood was collected from the carotid artery and the serum was isolated and stored in a state frozen at −80° C. Titer of this antiserum to homologous PCA for 48 hours was 1:32.

B) HOMOLOGOUS PCA TEST FOR 48 HOURS USING RATS

Three rats were used per group. After the hair at the back was cut, 0.05 ml each of anti-EWA rat serum diluted to 8-fold with physiological saline was intracutaneously injected to each rat at the back in 2 places to passively sensitize the rat. A test compound or its solution (physiological saline solution or CMC solution) was orally administered 47 hours after and 0.5 ml/100 g of 1% Evans Blue physiological saline containing 2 mg of antigen EWA was then intravenously administered to the tail vein an hour after the administration. Thirty minutes later, the animal was bled to death. The skin was peeled off and a leaked dye amount at the blue dyed portion was measured according to the method of Katayama et al. [Microbiol. Immunol., 22, 89 (1978)]. That is, the blue dyed portion was cut off with scissors, put into a test tube charged with 1 ml of 1 N potassium hydroxide and incubated at 37° C. for 24 hours. After 9 ml of a mixture of 0.6 N phosphate:acetone (5:13) was added to the system, the mixture was shaken followed by centrifugation at 2500 rpm for 10 minutes. The absorbancy of the supernatant at 620 nm was measured and the leaked dye amount was quantitatively determined by comparison with a calibration curve previously prepared. A value of one rat was obtained from a mean value of the two portions and an inhibition rate-of each rat was calculated according to the following equation.

Inhibition rate (%) =

$$\left( \frac{\begin{array}{c}\text{A mean amount leaked in} \\ \text{the group administered} \\ \text{with solvent}\end{array} - \begin{array}{c}\text{A leaked amount in the} \\ \text{group administered} \\ \text{with test compound}\end{array}}{\begin{array}{c}\text{A mean amount leaked in the group} \\ \text{administered with solvent}\end{array}} \right) \times 100$$

The case showing that the inhibition rate is 50% or more is judged to be positive in the PCA inhibition activity and the minimum dose in which at least one out of 3 rats was recognized to be positive was defined as the minimum effective dose (MED) of the test compound.

The results are shown in Table 3.

ACUTE TOXICITY TEST

Using three dd strain male mice weighing 20±1 g, a test compound was orally (po; 300 mg/kg) or intraperitoneally (ip; 100 mg/kg) administered. MLD (the minimum lethal dose) was determined by observing the mortality for seven days after administration.

The results are shown in Table 3.

TABLE 3

| Compound No.** | Acute Toxicity (MLD) mg/kg po | Acute Toxicity (MLD) mg/kg ip | Antiallergic Activity (MED) mg/kg po | TXA$_2$ Antagonizing Activity (MEC) μg/ml |
|---|---|---|---|---|
| 1b' | >300 | >100 | 10 | 3 |
| 8b | >300 | >100 | 10 | 1 |
| 9b' | >300 | >100 | 10 | 1 |
| 11b | >300 | >100 | 10 | 1 |
| 25b | >300 | >100 | 10 | 3 |
| 37b | >300 | >100 | 1 | 10 |
| 38b | >300 | >100 | 1 | 1 |
| E-73b | >300 | >100 | >100 | 10 |
| E-75b' | >300 | >100 | 100 | 0.1 |
| E-78b | >300 | >100 | >100 | 3 |
| E-79b | >300 | >100 | >100 | 30 |
| BM13177* (reference compound) | >300 | >100 | >100 | 3 |

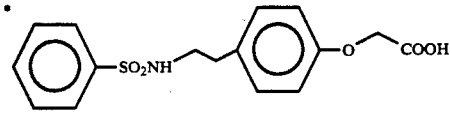

**In Compound No., symbol ' indicates an addition product of the corresponding compound in Tables 1 through 2 to a salt or solvent and, symbols E and Z represents E-form and Z-form, respectively (the same shall apply hereinafter).

As demonstrated in Table 3, Compound (I) and pharmaceutically acceptable salts thereof possess an excellent TXA$_2$antagonizing activity and some compounds also possess an antiallergic activity.

BINDING STUDY USING $^3$H-U46619 (TXA$_2$ RECEPTOR BINDING ACTIVITIES TEST)

Receptor binding was determined by a modified method of Kattelman et al. (Thrombosis Research, 41, 471 (1986)].

To a washed platelet suspension (1×10$^8$ platelets) of guinea pig were added 12 nM of tritium-labeled U46619 ($^3$H-U46619; NEN Co., Ltd.) and a test compound (final concentration: 1 μM) solution. After keeping at 37° C. for 20 minutes, the mixture was rapidly filtered through a glass fiber filter paper (GF/C; Whatman). Immediately, the filter paper was washed 5 times with 3 ml of ice-cold 50 mM Tris-hydroxymethylaminomethane buffer (containing 100 mM sodium chloride). The glass fiber filter was transferred to a vial and a scintillator (Ex-H; manufactured by Wako Pure Chemical Industries Co., Ltd.) was added thereto. The radioactivity was determined with a liquid scintillation counter.

It is already known that $^3$H-U46619 is capable of binding with TXA$_2$ receptor (see the publication supra). An inhibitory activity of the test compound against this binding means an ability of binding with the TXA$_2$ receptor. It is also known that a good relationship exists between this binding activity and the anti-platelet activity (TXA$_2$ antagonizing test).

An inhibitory activity (binding activity) of the test compound was calculated by the following equation.

(%) Inhibition =

$$\left\{ 1 - \frac{\text{Amount bound in the presence of a test compound} - \text{Amount of non-specific binding}}{\text{Amount of total binding} - \text{Amount of non-specific binding}} \right\} \times 100$$

(Notes)

Amount of the total binding is an amount of $^3$H-U46619-bound radioactivity in the absence of a test compound.

The amount of non-specific binding is used to mean an amount of $^3$H-U46619-bound radioactivity in the presence of 10 μM U-46619.

The amount bound in the presence of a test compound is an amount of $^3$H-U46619-bound radioactivity in the presence of a test compound in various concentrations.

The results are shown in Table 4.

TABLE 4

| Compound No. | % Inhibition |
|---|---|
| 11b | 70 |
| 25b | 78 |
| 38b | 81 |
| E-73b | 85 |
| E-75b' | 85 |
| E-78b | 83 |
| E-79b | 77 |
| Reference compounds: | |
| Ketotifen | −3 |
| Bm13177 | 31 |
| | −4 |

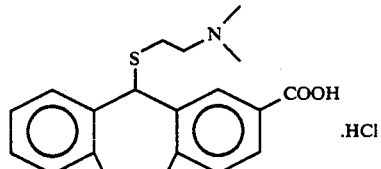

(Compound A)

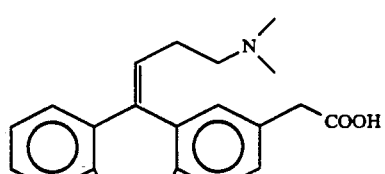

(Compound B)

As demonstrated in Table 4, Compound (I) and pharmaceutically acceptable salts thereof have an excellent binding ability to TXA$_2$receptor.

This inhibitory activity is not observed with hitherto known antiallergic agents, for example, Ketotifen [Merck Index, 10th edition, page 762 (1983)] and known antiallergic agents such as Compound (A) (Japanese Published Unexamined Patent Application No. 28972/1985) and Compound (B) (Japanese Published Unexamined Patent Application No. 10784/1988); one of excellent activity of Compound (I) is TXA$_2$receptor binding ability.

BINDING STUDY USING ³H-PYRILAMINE (HISTAMINE H₁ RECEPTOR BINDING)

Receptor binding was determined by the method of chang et al. [J. Neurochem., 32, 1953 (1979)].

The cerebellum of guinea pig was suspended in a 40-fold amount (V/W) of chilled 50 mM phosphate buffer (pH 7.5) with Polytron Homogenizer (Kinematica Co., Ltd.). The suspension was centrifuged (35,500×g, 10 minutes). The resulting precipitates were resuspended in an equal amount of fresh buffer followed by centrifugation. A 100-fold amount (V/W) of chilled buffer was added to the final precipitates.

To 1 ml of the membrane suspension adjusted as described above were added 50 μl of tritium-labeled pyrilamine (³H-pyrilamine; NEN Co., Ltd.) and 50 μl of a test compound. The mixture was allowed to stand at 25° C. for 30 minutes, 4 ml of chilled buffer was added thereto. The mixture was rapidly filtered through a glass fiber filter (GF/C; Whatman). The filter paper was further washed three times with 5 ml of buffer. Hereafter procedures were performed in a manner similar to the TXA₂ receptor binding test to determine radioactivity.

An inhibitory activity of the test compound against H₁ receptor was calculated by the following equation.

$$(\%)\text{ Inhibition} = \left(1 - \frac{\text{Amount bound in the presence of a test compound} - \text{Amount of non-specific binding}}{\text{Amount of total binding} - \text{Amount of non-specific binding}}\right) \times 100$$

(Notes)

Amount of the total binding is an amount of ³H-pyrilamine-bound radioactivity in the absence of a test compound.

The amount of non-specific binding is an amount of ³H-pyrilamine-bound radioactivity in the presence of 3 μM Astemizole (manufactured by Janesen Pharmaceutics).

The amount bound in the presence of a test compound is an amount of ³H-pyrilamine-bound radioactivity in the presence of a test compound in various concentrations.

Inhibitory activity of the test compounds at $10^{-6}$ M are shown in table 5.

TABLE 5

| Compound No. | (%) Inhibition |
|---|---|
| 1b' | 68 |
| 11b | 95 |
| 25b | 95 |
| 38b | 92 |
| Reference Compounds: | |
| Ketotifen | 100 |
| BM13177 | 0 |
| Compound A | 88 |

Compound (I) and pharmaceutically acceptable salts thereof may be administered alone but in general, it is preferably administered as combination medical preparation. These medical preparations are used for animal and human beings.

The medical preparation in accordance with the present invention may contain, as an active ingredient, Compound (I) or pharmaceutically acceptable salts thereof singly or as admixture with other optional effective components for different treatment. Further these medical preparations can be produced by optional procedures well known in the pharmaceutical field, by mixing the active ingredient together with one or more pharmaceutically acceptable carriers.

Herein, as the optional effective components for different treatment combined with Compound (I) or pharmaceutically acceptable salts thereof, mention may be made of, for example, a steroid, a non-steroid antiinflammatory agent, a peripheral analgesic, a leucotriene antagonist, a leucotriene biosynthesis inhibitor, an H₂ receptor antagonist, an antihistaminic agent, a histamine release inhibitor, a bronchodilator, an angiotensin converting enzyme inhibitor, a thromboxane A₂ biosynthesis inhibitor, an H⁺-K⁺ATPase inhibitor, a coronary dilator, a calcium antagonist, a diuretic, a xanthine oxidase inhibitor, a cerebral circulation improving agent, a celebral metabolism activator, a cerebral protecting agent, a liver protecting agent, an antiplatelet agent, a thrombolytic agent, an adrenaline α receptor antagonist, an adrenergic β receptor agent, an adrenaline β receptor antagonist, a serotonine antagonist, a platelet activation factor (PAF) antagonist, an adenosine receptor antagonist, an antihyperlipidemic agent, a cholesterol biosynthesis inhibitor, an immunostimulating agent, an immunosuppressive agent, an anticancer agent, etc.

It is preferred that the most effective route for treatment be selected as a route for administration, oral or parenteral administration such as intrarectal, topical, intranasal, intraocular, intrabuccal, subcutaneous, intramuscular and intravenfus route etc.,, As the form of administration preparations of the invention may be administered a capsule, a tablet, a granule, a powder, a syrup, an emulsion, a suppository, an ointment, an eyedrop, a nosedrop, a troche, an aerosol, an injection, etc.

A liquid preparation suited for oral administration, for example, an emulsion and a syrup can be prepared using water; sugars such as sucrose, sorbitol, fructose, etc.; glycols such as polyethylene glycol, propylene glycol, etc.; oils such as sesame oil, olive oil, soybean oil, etc.; antiseptics such as a p-hydroxybenzoic acid ester, etc.; flavors such as strawberry flavor, pepper mint, etc. Further a capsule, a tablet, a powder and a granule, etc. can be prepared using an excipient such as lactose, glucose, sucrose, mannitol, etc.; a disintegrator such as starch, sodium alginate, etc.; a lubricant such as magnesium stearate, talc, etc.; a binder such as polyvinyl alcohol, hydroxypropyl cellulose, gelatin, etc.; a surfactant such as an aliphatic ester, etc.; a plasticizer, such as glycerine, etc.

A preparation suited for parenteral administration is composed of a sterile aqueous preparation containing active compounds which are preferably isotonic to the blood of the recipient. For example, with an injection, a solution for injection is prepared using carriers composed of a saline solution, a glucose solution or a mixture of saline water and glucose solution.

A nasal spray preparation is composed of a purified aqueous solution of the active compounds which contains an antiseptic and an isotonic agent. Such a preparation is adjusted to pH compatible with the nasal membrane and to an isotonic state.

An ocular preparation is prepared in a manner similar to the nasal spray, except that pH and isotonic factors are controlled so as to fit those of eyes.

A topical preparation is prepared by dissolving or suspending the active compound in one or more media, for example, a mineral oil, petroleum, a polyvalent alcohol or other bases used for topical medical preparations.

A preparation for rectal administration is provided as a suppository using conventional carriers, for example, cacao fat, hydrogenated fat or hydrogenated fat carboxylic acid, etc.

Further these parenteral preparations may also be added with one or more auxiliary components such as a diluent, a fragrance, an antiseptic (including an antioxidant), an excipient, a disintegrator, a lubricant, a binder, a surfactant, a plasticizer and the like. YR)i Effective dose and regimen of administration of Compound (I) or pharmaceutically acceptable salts thereof vary depending upon mode of administration, age and body weight of the patient and propertier or severity of conditions to be treated. In general, daily dose is 0.01 to 1,000 mg/person which may be administered as a single or divided doses.

Hereafter, the present invention is described by referring to Reference Examples and Examples below.

Intermediates obtained in the following Reference Examples are shown in Table 6.

TABLE 6

| Compound (Reference Example) | $X_1-X_2$ | $R^o$ | $X^o$ |
|---|---|---|---|
| a (1) | —CH$_2$O— | 2-COOCH$_3$ | =O |
| b (2) | " | " | —OH |
| c (3) | " | " | =CHCH$_2$Cl |
| d (4) | " | 2-CH$_2$COOCH$_3$ | =O |
| e (5) | " | " | =CHCH$_2$Cl |
| f (6) | " | 2-C(CH$_3$)$_2$COOCH$_3$ | =O |
| g (7) | " | " | —OH |
| h (8) | " | 2-COOCH$_3$ | —S~~OH |
| i (9) | " | " | —S~~Cl |
| j (10) | " | " | —S~~I |
| k (11) | " | " | —S–CH$_2$CH$_2$–N(piperazine)NH |
| l (12) | " | 2-C(CH$_3$)$_2$COOCH$_3$ | —S~~OH |
| m (13) | —CH$_2$O— | 2-C(CH$_3$)$_2$COOCH$_3$ | —S~~Cl |
| n (14) | " | " | —S~~I |
| o (15) | —CH$_2$—CH$_2$— | 2-COOCH$_3$ | —S~~OH |
| p (16) | " | " | —S~~I |
| q (17) | —CH=CH— | " | —S~~OH |
| r (18) | " | " | —S~~I |
| s (19) | —CH$_2$O— | " | =CHCH$_2$N(piperazine)NH |
| t (20) | " | " | =CHCH$_2$CH$_2$OSO$_2$CH$_3$ |

TABLE 6-continued

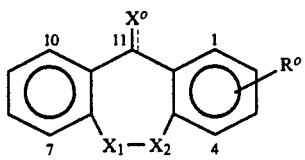

| Compound (Reference Example) | $X_1-X_2$ | $R^o$ | $X^o$ |
|---|---|---|---|
| u (21) | " | " | 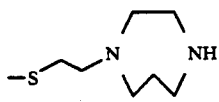 |

REFERENCE EXAMPLE 1

Methyl 11-oxo-6,11-dihydrodibenz[b,e]oxepin-2-carboxylate (Compound a)

A mixture of 348.9 g of methyl p-hydroxybenzoate sodium salt, 402.4 g of phthalide and 200 g of sodium chloride was stirred at 150° C. for 6 hours. After completion of the reaction, the reaction mixture was cooled to room temperature and 4 liters of 10% acetic acid aqueous solution were added thereto. The mixture was allowed to stand at room temperature overnight. After stirring at room temperature for 3 hours, crystals were recovered by filtration. To the crystals was added 6 liters of water. After stirring at room temperature for 30 minutes, the crystals were taken out by filtration. To the crystals was added 3 liters of toluene. The mixture was stirred at room temperature for an hour. The crystals were taken out by filtration and dried by heating under reduced pressure to give 393.9 g of 2-(4-methoxycarbonylphenoxy)methyl benzoate.

IR (KBr tablet, cm$^{-1}$): 3400, 1700, 1610, 1260, 1235.

In 5.0 liters of methylene chloride was suspended 392.7 g of the thus obtained 2-(4-methoxycarbonylphenoxy)methyl benzoate and, 266.0 g of trifluoroacetic anhydride was added to the suspension. After stirring at room temperature for an hour, 19.4 g of boron trifluoride ethyl ether complex was added to the mixture followed by stirring at-room temperature for 2 hours. The reaction solution was poured into ice water. After fractionation, the organic phase was washed with a diluted sodium hydroxide aqueous solution and then with water, dried over anhydrous magnesium sulfate and concentrated under reduced pressure. The concentrate was recrystallized from isopropyl ether to obtain 335.3 g of the objective compound as white crystals.

Melting point: 128°–129° C.

| Elemental analysis: as $C_{16}H_{12}O_4$ | | |
|---|---|---|
| | C | H |
| Found (%) | 71.55 | 4.48 |
| Calcd. (%) | 71.63 | 4.51 |

NMR (CDCl$_3$, δ, ppm): 3.84(s, 3 H), 5.14(s, 2 H), 6.87–8.93(m, 7 H).

IR (KBr tablet, cm$^{-1}$): 1710, 1650, 1610, 1250, 1010.

REFERENCE EXAMPLE 2

Methyl 11-hydroxy-6,11-dihydrodibenz[b,e]oxepin-2-carboxylate (Compound b)

Compound a, 50 g, obtained in Reference Example 1 was suspended in 300 ml of methanol and 6.3 g of sodium borohydride was added to the suspension. The mixture was stirred at room temperature for 2 hours. After completion of the reaction, 10 ml of acetic acid and 300 ml of water were added thereto followed by stirring for 30 minutes. Insoluble matters were taken out by filtration and washed with methanol and then with water. By drying with heating under reduced pressure, 40 g of the objective compound was obtained.

NMR (CDCl$_3$, δ, ppm): 2.16(s, 6 H), 2.30–2.76(m, 4 H), 3.83(s, 3 H), 4.83 and 6.40(ABq, J=12.6 Hz, 2 H), 5.01(s, 1 H), 6.79–7.93(m, 7 H).

IR (neat, cm$^{-1}$): 2950, 1710, 1240, 1015.

REFERENCE EXAMPLE 3

Methyl (E)-11-(2-chloroethylidene)-6,11-dihydrodibenz[b,e]oxepin -2-carboxylate (Compound c)

4-Methylpiperazine, 30 ml, and 74 g of paraformaldehyde were dissolved in 2 l of tetrachloroethane and 100 ml of trifluoroacetic acid was dropwise added to the solution. After stirring at 60° C. for 2 hours, a solution of 36 g of methyl 11-methylene-6,11-dihydrodibenz[b,e]-oxepin-2-carboxylate in 600 ml of tetrachloroethane was dropwise added to the reaction mixture followed by stirring at 90° C. for further 3 hours. The reaction mixture was concentrated to dryness under reduced pressure and 4 N hydrochloric acid aqueous solution was added to the residue to adjust pH to 1. Then, the mixture was washed with diethyl ether. Thereafter, 10 N sodium hydroxide aqueous solution was added to adjust pH to 13. Extraction was performed with 3 l of methylene chloride. After washing with saturated sodium chloride aqueous solution and drying over anhydrous sodium sulfate, the solvent was distilled off under reduced pressure. The resulting residue was subjected to silica gel column chromatography (eluent; hexane:ethyl acetate:triethylamine=5:5:1) to give 44 g of methyl 11-[2-(4-methyl-1-piperazinyl)ethylidene]-6,11-dihydrodibenz[b,e]oxepin-2-carboxylate as colorless oil.

MS (m/z): 378 (M+).

NMR (CDCl$_3$, δ, ppm): 2.24(s, 3 H), 2.45(s, 8 H), 2.94-3.32(m, 2 H), 3.84(s, 3 H), 5.22(bs, 2 H), 5.85 and 6.22(t, J=6.8 Hz, 1 H), 6.66-8.07(m, 7 H).

E-form compound, 21.5 g, isolated from the Z/E mixture described above in a conventional manner and 23.5 g of sodium acetate were suspended in 250 ml of dichloroethane and, 27.1 ml of ethyl chloroformate was dropwise added to the suspension. After completion of the dropwise addition, the mixture was stirred at room temperature for an hour and the solvent was distilled off under reduced pressure. The residue was extracted with 400 ml of ethyl acetate. After washing with saturated sodium chloride aqueous solution and drying over anhydrous sodium sulfate, the solvent was distilled off under reduced pressure. The obtained crude product was recrystallized from isopropanol to give 14.3 g of the objective compound as white crystals.

Melting point: 134°-135° C.

| Elemental analysis: as C$_{18}$H$_{15}$ClO$_3$ | | |
|---|---|---|
| | C | H |
| Found (%) | 68.55 | 4.77 |
| Calcd. (%) | 68.68 | 4.80 |

NMR (CDCl$_3$, δ, ppm): 3.90(s, 3 H), 4.16(d, J=8.1 Hz, 2 H), 4.88(bs, 1 H), 5.57(bs, 1 H), 6.31(t, J=8.1 Hz, 1 H), 6.79-8.04(m, 7 H).

REFERENCE EXAMPLE 4

Methyl 11-oxo-6,11-dihydrodibenz[b,e]oxepin-2-acetate (Compound d)

The corresponding starting material was used, treated in a manner similar to Reference Example 1 and recrystallized from methanol to give the objective compound as light yellow crystals.

Melting point: 75°-76° C.

REFERENCE EXAMPLE 5

Methyl (E)-11-(2-chloroethylidene)-6,11-dihydrodibenz[b,e]-oxepin-2-acetate (Compound e)

The corresponding starting material was used, treated in a manner similar to Reference Example 3 and recrystallized from isopropanol to give the objective compound as white crystals.

Melting point: 127°-128° C.

| Elemental analysis: as C$_{19}$H$_{17}$ClO$_3$ | | |
|---|---|---|
| | C | H |
| Found (%) | 69.37 | 5.40 |
| Calcd. (%) | 69.41 | 5.21 |

NMR (CDCl$_3$, δ, ppm): 3.55(s, 2 H), 3.69(s, 3 H), 4.14 (d, J=8.1 Hz, 2H), 4.7-5.4(m, 2 H), 6.23(t, J=8.1 Hz, 1H), 6.74(d, J=8.1 Hz, 1 H), 6.95-7.4 (m, 6H).

IR (KBr tablet, cm$^{-1}$): 1731, 1487, 1256, 1137, 1004.

REFERENCE EXAMPLE 6

Methyl 2-methyl-2-[(11-oxo-6,11-dihydrodibenz[b,e]oxepin)-2-yl]propionate (Compound f)

Compound d, 30 g, obtained in Reference Example 4 was suspended in 300 ml of dimethylformamide and 30 g of potassium hydroxide as powder and then 27 ml of methyl iodide were added to the suspension. The mixture was stirred at room temperature for 2 hours. The solvent was distilled off under reduced pressure and the residue was extracted with 500 ml of ethyl acetate. The extract was washed successively with saturated sodium bicarbonate aqueous solution and saturated sodium chloride aqueous solution. After drying over anhydrous magnesium sulfate, the solvent was distilled off under reduced pressure. The obtained residue was subjected to silica gel column chromatography (eluent; hexane:ethyl acetate=10:1) for purification to give 3.6 g of the objective compound as colorless oil.

NMR (CDCl$_3$, δ, ppm): 1.62(s, 6 H), 3.66(s, 3 H), 5.17 (s, 2 H), 7.01(d, J=8.8 Hz, 1 H), 7.2-7.9(m, 5 H), 8.22(d, J=2.6 Hz, 1 H).

IR (neat, cm$^{-1}$): 2874, 1729, 1648, 1597, 1490, 1016.

REFERENCE EXAMPLE 7

Methyl 2-methyl-2-[(11-hydroxy-6,11-dihydrodibenz[b,e]-oxepin)-2-yl]propionate (Compound g)

The objective compound was obtained as colorless oil from Compound f obtained in Reference Example 6 in a manner similar to Reference Example 2.

NMR (CDCl$_3$, δ, ppm): 1.56(s, 6 H), 3.62(s, 3 H), 4.97 and 5.90(ABq, J=13.1 Hz, 2 H), 5.61(s, 1 H), 6.87 (d, J=8.4 Hz, 1 H), 7.05-7.40(m, 6 H).

IR (neat, cm$^{-1}$): 2974, 1728, 1497, 1010.

REFERENCE EXAMPLE 8

Methyl 11-(2-hydroxyethyl)thio-6,11-dihydrodibenz[b,e]-oxepin-2-carboxylate (Compound h)

In 400 ml of methylene chloride was suspended 40.0 g of Compound b obtained in Reference Example 2. Trifluoroacetic anhydride, 21.0 ml, was added to the suspension followed by stirring at room temperature for an hour. Then, 10.7 ml of 2-mercap was added to the mixture followed by stirring for additional 4 hours. After 100 ml of methylene chloride was added to the reaction mixture, the mixture was washed with saturated aqueous sodium chloride solution. After drying over anhydrous magnesium sulfate, the solvent was distilled off under reduced pressure. The obtained crude product was recrystallized from toluene to give 37.6 g of the objective compound as white crystals.

Melting point: 128°-130° C.

| Elemental analysis: as C$_{18}$H$_{18}$O$_4$S | | |
|---|---|---|
| | C | H |
| Found (%) | 65.26 | 5.55 |
| Calcd. (%) | 65.43 | 5.49 |

NMR (CDCl$_3$, δ, ppm): 2.66(dt, J=2.1, 6.0 Hz, 2 H), 3.69 (t, J=5.9 Hz, 2H), 3.89(s, 3 H), 4.91 and 6.43(ABq, J=12.7 Hz, 2 H), 5.09(s, 1 H), 6.82-7.98(m, 7 H).

IR (KBr tablet, cm$^{-1}$): 3420, 1708, 1683, 1610, 1437, 1318, 1008.

REFERENCE EXAMPLE 9

Methyl 11-(2-chloroethyl)thio-6,11-dihydrodibenz[b,e]-oxepin-2-carboxylate (Compound i)

Compound h, 20.0 g, obtained in Reference Example 8 was dissolved in 200 ml of dimethylformamide and, 12 ml of 2,4,6-cholidine and 4.0 g of lithium chloride were added to the solution. Under ice cooling, 5.4 ml of methanesulfonyl chloride was dropwise added to the mixture. After stirring at room temperature overnight, the solvent was distilled off under reduced pressure. The residue was extracted with ethyl acetate. The extract was washed successively with 1 N hydrochloric acid aqueous solution and saturated sodium chloride aqueous solution. After drying over anhydrous magnesium sulfate, the solvent was distilled off under reduced pressure. The obtained residue was purified by silica gel column chromatography (eluent; hexane:ethyl acetate=5:1) and crystallized from hexane to give 20.8 g of the objective compound.

Melting point: 100°–102° C.

| Elemental analysis: as $C_{18}H_{17}ClO_3S$ | | |
|---|---|---|
| | C | H |
| Found (%) | 61.77 | 4.80 |
| Calcd. (%) | 61.97 | 4.91 |

NMR (CDCl$_3$, δ, ppm): 2.54–3.62(m, 4 H), 3.84(s, 3 H), 5.04(s, 1 H), 4.87 and 6.37(ABq, J=13.2 Hz, 2 H), 6.76–8.12(m, 7 H)

IR (CHCl$_3$, cm$^{-1}$): 1714, 1611, 1322, 1295, 1132, 1008

REFERENCE EXAMPLE 10

Methyl 11-(2-iodoethyl)thio-6,11-dihydrodibenz[b,e]oxepin-2-carboxylate (Compound j)

Compound i, 10.1 g, obtained in Reference Example 9 was dissolved in 150 ml of acetonitrile and, 14.6 g of sodium iodide was added to the solution. The mixture was heated under reflux for 5 hours. After allowing it to stand for cooling, the reaction mixture was extracted with ethyl acetate and the extract was washed twice with saturated sodium chloride aqueous solution. After drying over anhydrous magnesium sulfate, the solvent was distilled off under reduced pressure. The residue was purified by silica gel column chromatography (eluent; hexane:ethyl acetate=10:1) and further solidified with hexane to give 3.1 g of the objective compound as white solid.

Melting point: 111°–113° C.

| Elemental analysis: as $C_{18}H_{17}IO_3S$ | | |
|---|---|---|
| | C | H |
| Found (%) | 49.08 | 3.71 |
| Calcd. (%) | 49.10 | 3.89 |

NMR (CDCl$_3$, δ, ppm): 2.68–3.22(m, 4 H), 3.88(s, 3 H), 5.09(s, 1 H), 4.91 and 6.37(ABq, J=13.2 Hz, 2 H), 6.78–8.08(m, 7 H).

IR (CHCl$_3$, cm$^{-1}$): 1714, 1611, 1295, 1120, 1008.

REFERENCE EXAMPLE 11

Methyl [2-(1-piperazinyl)ethyl]thio-6,11-dihydrodibenz[b,e]oxepin-2-carboxylate (Compound k)

Compound j, 7.0 g, obtained in Reference Example 10 and 6.8 g of piperazine were heated under reflux for 8 hours in 300 ml of ethanol. The solvent was distilled off under reduced pressure. 4 N hydrochloric acid aqueous solution was added to the residue to adjust pH to 3 followed by washing with diethyl ether. Next, 10 N sodium hydroxide aqueous solution was added to adjust pH to 13. Extraction was performed with 500 ml of ethyl acetate. After washing successively with saturated sodium bicarbonate aqueous solution and saturated sodium chloride aqueous solution, the extract was dried over anhydrous sodium sulfate. The solvent was distilled off under reduced pressure to give 5.9 g of the objective compound as light yellow oil. The product was provided for the following reaction without further purification.

NMR (CDCl$_3$, δ, ppm): 2.19–3.33(m, 12 H), 3.84(s, 3 H), 5.06(s, 1 H), 4.86 and 6.44(ABq, J=12.7 Hz, 2 H), 6.76–8.12(m, 7 H).

MS (m/Z): 402 (M+).

REFERENCE EXAMPLE 12

Methyl 2-methyl-2-[11-(2-hydroxyethyl)thio-6,11-dihydrodibenz[b,e]oxepin]-2-yl]propionate (Compound l)

The objective compound was obtained as colorless oil in a manner similar to Reference Example 8 using Compound g obtained in Reference Example 7.

NMR (CDCl$_3$, δ, ppm): 1.56(s, 6 H), 2.64(dt, J=2.2, 6.0 Hz, 2 H), 3.65(s, 3 H), 4.85 and 6.27(ABq, J=13.1 Hz, 2 H), 5.01(s, 1 H), 6.7–7.4(m, 7 H).

REFERENCE EXAMPLE 13

Methyl 2-methyl-2-[[11-(2-chloroethyl)thio-6,11-dihydrodibenz[b,e]oxepin]-2-yl]propionate (Compound m)

The objective compound was obtained as colorless oil in a manner similar to Reference Example 9 using Compound l obtained in Reference Example 12.

NMR (CDCl$_3$, δ, ppm): 1.57(s, 6 H), 2.6–2.9(m, 2 H), 3.2–3.4(m, 2 H), 3.65(s, 3 H), 4.85 and 6.23(ABq, J=13.1 Hz, 2 H), 5.04(s, 1 H), 6.7–7.4(m, 7 H).

REFERENCE EXAMPLE 14

Methyl 2-methyl-2-[[11-(2-iodoethyl)thio-6,11-dihydro-dibenz[b,e]oxepin]-2-yl]propionate (Compound n)

The objective compound was obtained as colorless oil in a manner similar to Reference Example 10 using Compound m obtained in Reference Example 13.

NMR (CDCl$_3$, δ, ppm): 1.56(s, 6 H), 3.64(s, 3 H), 5.27 (s, 1 H)

REFERENCE EXAMPLE 15

Methyl 5-(2-hydroxyethyl)thio-10,11-dihydro-5 H-dibenzo-[a,d]cyclohepten-3-carboxylate (Compound o)

In 15.3 ml of methylene chloride was suspended 0.51 g of methyl 5-hydroxy-10,11-dihydro-5 H-dibenzo[a,d]-cyclohepten-3-carboxylate. Under ice cooling, 0.27 ml of trifluoroacetic anhydride was added to the suspension followed by stirring at room temperature for an hour. Then, 0.14 ml of 2-mercaptoethanol was added to the mixture followed by stirring for further an hour. After 10 ml of methylene chloride was added to the reaction mixture, the mixture was washed with saturated aqueous sodium chloride solution. After drying over anhydrous magnesium sulfate, the solvent was distilled off under reduced pressure. The obtained residue was purified by silica gel column chromatography (eluent; hexane:ethyl acetate=1:1) and recrystallized from toluene to give 0.51 g of the objective compound as light yellow crystals.

Melting point: 107°–109° C.

NMR (CDCl₃, δ, ppm): 2.51–2.65(m 3 H), 2.75–3.03(m, 2 H), 3.56–3.98(m, 4 H), 3.87(s, 3 H), 5.16(s, 1 H), 7.14–7.25(m, 5 H), 7.82(dd, J=1.5, 7.9 Hz, 1 H), 7.91(s, 1 H).

REFERENCE EXAMPLE 16

Methyl 5-(2-iodoethyl)thio-10,11-dihydro-5 H-dibenzo[a,d]-cyclohepten-3-carboxylate (Compound p)

Compound o, 0.46 g, obtained in Reference Example 15 and 1.10 g of triphenyl phosphine were suspended in 9.2 ml of benzene. While stirring under ice cooling, 0.65 ml of diethyl azodicarboxylate was added to the suspension followed by stirring at room temperature for 10 minutes. Then, 0.26 ml of iodomethane was added to the mixture followed by stirring at room temperature for 30 minutes, After 10 ml of ethyl acetate and 10 ml of water were added thereto, the mixture was extracted with ethyl acetate. The extract was washed with saturated aqueous sodium chloride solution. After drying over anhydrous magnesium sulfate, the solvent was distilled off under reduced pressure. The obtained residue was purified by silica gel column chromatography (eluent; hexane:ethyl acetate=3:1) to give 0.57 g of the objective compound as pale yellow oil.

NMR (CDCl₃, δ, ppm): 2.70–3.08(m, 6 H), 3.63–3.81(m, 2 H), 3.89(s, 3 H), 5.17(s, 1 H), 7.17–7.32(m, 5 H), 7.84(dd, J=1.7, 7.8 Hz, 1 H), 7.92(s, 1 H).

REFERENCE EXAMPLE 17

Methyl 5-(2-hydroxyethyl)thio-5 H-dibenzo[a,d]cyclohepten -3-carboxylate (Compound q)

The corresponding starting material was used, treated in a manner similar to Reference Example 15 and recrystallized from toluene to give the objective compound as pale yellow crystals.

Melting point: 130°–132° C.

NMR (CDCl₃, δ, ppm): 2.30–2.50(m, 3 H), 3.51(t, J=6.2 Hz, 2 H), 3.89(s, 3 H), 5.31(s, 1 H), 7.00(s, 1 H), 7.02(s, 1 H), 7.09–7.41(m, 5 H), 7.91(dd, J=1.5, 7.9 Hz, 1 H), 8.01(s, 1 H).

REFERENCE EXAMPLE 18

Methyl 5-(2-iodoethyl)thio-5 H-dibenzo[a,d]cyclohepten-3-carboxylate (Compound r)

Compound q obtained in Reference Example 17 was used and treated in a manner similar to Reference Example 16 to give the objective compound as pale yellow oil.

NMR (CDCl₃, δ, ppm): 2.57–3.07(m, 4 H), 3.92(s, 3 H), 5.31(s, 1 H), 7.01(s, 1 H), 7.02(s, 1H), 7.09–7.41 (m, 5 H), 7.91(dd, J=1.5, 7.9 Hz, 1 H), 8.01(s, 1 H).

REFERENCE EXAMPLE 19

Methyl (E)-11-[2-(1-piperazinyl)ethyl]thio-6,11-dihydro-dibenz[b,e]oxepin-2-acetate (Compound s)

The objective compound was obtained as colorless oil from Compound c (E-form) obtained in Reference Example 3 in a manner similar to Reference Example 11.

NMR (CDCl₃, δ, ppm): 1.95–3.0(m, 7 H), 3.10(d, J=7.0 Hz, 2 H), 3.83(s, 3H), 4.75–5.5(m, 2 H), 6.20(t, J=7.0 Hz, 1 H), 6.71(d, J=8.5 Hz, 1 H), 6.95–7.45(m, 4 H), 7.73(dd, J=2.2, 8.5 HZ, 1 H), 7.99(d, J=2.2 Hz, 1 H).

REFERENCE EXAMPLE 20

Methyl (E,Z)-11-[3-(methylsulfonyl)oxy]propylidene-6,11-dihydrodibenz[b,e]oxepin-2-carboxylate (Compound t)

[3-[(Tetrahydro-2 H-pyran-2-yl)oxy]propyl]triphenylphosphonium bromide, 40.0 g, was suspended in 250 ml of tetrahydrofuran. Under ice cooling in nitrogen atmosphere, 50 ml of n-butyl lithium/hexane solution (1.6 N) was dropwise added to the suspension. After stirring at room temperature for an hour, 15.0 g of Compound a obtained in Reference Example 1 was added thereto followed by stirring at room temperature for 12 hours. After 50 ml of water was added to the reaction mixture, the mixture was extracted with 1 l of ethyl acetate. After washing thrice with saturated sodium chloride aqueous solution and drying over anhydrous sodium sulfate, the solvent was distilled off under reduced pressure. The obtained residue was dissolved in 500 ml of dioxane and 200 ml of water and 1.0 g of p-toluenesulfonic acid were added to the solution followed by heating under reflux for an hour. The mixture was concentrated under reduced pressure and the obtained residue was extracted with 1 k of ethyl acetate. After washing successively with saturated sodium bicarbonate aqueous solution and saturated sodium chloride aqueous solution, the extract was dried over anhydorus sodium sulfate. The solvent was distilled off under reduced pressure. The resulting residue was subjected to silica gel column chromatography (eluent; toluene:ethyl acetate=1:1) to give 9.8 g of methyl (E,Z)-11-(3-hydroxy)propylidene -6,11-dihydrodibenz[b,e]oxepin-2-carboxylate. A ratio of E/Z was approximately 3:7 by NMR.

The obtained product, 4.8 g, mainly composed of the Z-form and 10.0 g of p-toluenesulfonic acid were stirred in 250 ml of acetic acid at 100° C. for 42 hours. After completion of the reaction, the solvent was distilled off under reduced pressure and 200 ml of methanol was added to the residue followed by heating under reflux for 3 hours. The solvent was distilled off and reduced pressure and the residue was extracted with 500 ml of ethyl acetate. After washing with saturated sodium bicarbonate aqueous solution and drying over anhydrous sodium sulfate, the solvent was distilled off under reduced pressure. The obtained residue was subjected to silica gel column chromatography (eluent; hexane:ethyl acetate=1:1) to give 4.5 g of the product showing an E/Z ratio of about 1:1.

NMR (CDCl₃, δ, ppm): 2.17–2.72(m, 2 H), 3.37–3.76(m, 2 H), 3.77(s, 3 H), 4.68–5.43(m, 1 H), 5.70(t, J=7.4 Hz, 1.5 H; Z form), 6.40(t, J=6.9 Hz, 1.5 H; E form), 6.52–8.12(m, 7 H).

The aforesaid product, 3.5 g, showing an E/Z ratio of about 1:1 was dissolved in 50 ml of pyridine and 1.7 ml of methanesulfonyl chloride was dropwise added under ice cooling. After stirring for an hour under ice cooling, the solvent was distilled off under reduced pressure. The residue was extracted with 200 ml of ethyl acetate. The extract was washed in succession with 1N hydrochloric acid aqueous solution, saturated sodium bicarbonate aqueous solution and saturated sodium chloride aqueous solution. After drying over anhydrous magnesium sulfate, the solvent was distilled off under reduced pressure to give 4.3 g of the objective compound as colorless oil.

NMR (CDCl$_3$, δ, ppm): —SO$_2$CH$_3$; 2.93(s, 1.5 H; E form), 3.00(s, 1.5 H; Z form).

This product was provided for use in the following reaction step without particular purification. A ratio of E/Z was about 1:1.

REFERENCE EXAMPLE 21

Methyl 11-[2-(1-homopiperazinyl)ethyl]thio-6,11-dihydrodibenz[b,e]oxepin-2-carboxylate (Compound u)

The objective compound was obtained as colorless oil in a manner similar to Reference Example 11, using Compound j obtained in Reference Example 10 and homopiperazine.

NMR (CDCl$_3$, δ, ppm): 1.4–2.0(m, 2 H), 2.4–3.1(m, 12 H), 3.85(s, 3 H), 5.02(s, 1 H), 4.87 and 6.44(ABq, J=12.9 Hz, 2 H), 6.75–8.05(m, 7 H).

IR (neat, cm$^{-1}$): 2928, 1716, 1610, 1249, 1118, 1007.

EXAMPLE 1

Methyl 11-[2-(4-phenyl-1-piperazinyl)ethyl]thio-6,11-dihydrodibenz[b,e]oxepin-2-carboxylate (Compound 1a)

After 6.1 g of Compound j obtained in Reference Example 10 and 6.0 ml of 1-phenylpiperazine were heated under reflux in 300 ml of ethanol for 7.5 hours, the solvent was distilled 6,L3f under reduced pressure. The residue was extracted with 500 ml of ethyl acetate. The extract was washed in succession with saturated sodium bicarbonate aqueous solution and saturated sodium chloride aqueous solution and dried over anhydrous sodium sulfate. Thereafter, the solvent was distilled off under reduced pressure. The obtained residue was subjected to silica gel column chromatography (eluent; hexane:ethyl acetate:triethylamine=30:10:3). The resulting crude product was solidified with diethyl ether to give 3.1 g of the objective compound.

EXAMPLE 2

Methyl 11-[2-(4-phenyl-1-piperazinyl)ethyl]thio-6,11-dihydrodibenz[b,e]oxepin-2-carboxylate.dihydrochloride (Compound 1a')

Compound 1a, 1.2 g, obtained in Example 1 was dissolved in 200 ml of isopropanol and 2 ml of 6 N hydrochloric acid/isopropanol solution was added to the solution followed by stirring at room temperature for 2 hours. The solvent was distilled off under reduced pressure. The obtained crude product was recrystallized from isopropanol to give 0.9 g of the objective compound.

In Examples 3 through 7 below, the objective compound was prepared using Compound j obtained in Reference Example 10 and the corresponding piperazine compound in a manner similar to Example 1.

EXAMPLE 3

Methyl 11-[2-[4-(4-fluorophenyl)-1-piperazinyl]ethyl]thio-6,11-dihydrodibenz[b,e]oxepin-2-carboxylate (Compound 8a)

EXAMPLE 4

Methyl 11-[2-[4-(2-methoxyphenyl-1-piperazinyl)ethyl]thio-6,11-dihydrodibenz[b,e]oxepin-2-carboxylate (Compound 9a)

EXAMPLE 5

Methyl 11-[2-(4-benzyl-1-piperazinyl)ethyl]thio-6,11-dihydrodibenz[b,e]oxepin-2-carboxylate (Compound 11a)

EXAMPLE 6

Methyl 11-[2-(4-piperonyl-1-piperazinyl)ethyl]thio-6,11-dihydrodibenz[b,e]oxepin-2-carboxylate (Compound 15a)

EXAMPLE 7

Methyl 11-[2-[4-(diphenylmethyl)-1-piperazinyl]ethyl]thio-6,11-dihydrodibenz[b,e]oxepin-2-carboxylate (Compound 16a)

In Examples 8 through 14 below, the objective compound was prepared using Compound j obtained in Reference Example 10 and the corresponding piperidine compound in a manner similar to Example 1.

EXAMPLE 8

Methyl 11-[2-(4-phenyl-1-piperidinyl)ethyl]thio-6,11-dihydrodibenz[b,e]oxepin-2-carboxylate (Compound 37a)

EXAMPLE 9

Methyl 11-[2-(4-benzyl-1-piperidinyl)ethyl]thio-6,11-dihydrodibenz[b,e]oxepin-2-carboxylate (Compound 38a)

EXAMPLE 10

Methyl 11-[2-[4-[2(3 H)-benzimidazolon-1-yl]piperidino]-ethyl]thio -6,11-dihydrodibenz[b,e]oxepin-2-carboxylate (Compound 47a)

EXAMPLE 11

Methyl 11-[2-(4-phenyl-4-hydroxy-1-piperidinyl)ethyl]thio-6,11-dihydrodibenz[b,e]oxepin-2-carboxylate (Compound 50a)

EXAMPLE 12

Methyl 11-[2-(4-benzyl-4-hydroxy-1-piperidinyl)ethyl]thio-6,11-dihydrodibenz[b,e]oxepin-2-carboxylate (Compound 51a)

EXAMPLE 13

Methyl 11-[2-[4-(4-chlorobenzoyl)-1-piperidinyl]ethyl]-thio-6,11-dihydrodibenz[b,e]oxepin-2-carboxylate (Compound 53a)

EXAMPLE 14

Methyl 11-[2-(1-phenyl-1,3,8-triazaspiro[4.5]decan-4-on-8-yl)ethyl]thio-6,11-dihydrodibenz[b,e]oxepin-2-carboxylate (Compound 58a)

In Examples 15 through 17 below, the objective compound was prepared using the corresponding starting material n, p or r and 4-benzylpiperidine in a manner similar to Example 1.

EXAMPLE 15

Methyl 2-methyl-2-[11-[2-(4-benzyl-1-piperidinyl)ethyl]thio-6,11-dihydrodibenz[b,e]oxepin-2-yl]propionate (Compound 41a)

EXAMPLE 16

Methyl 5-[2-(4-benzyl-1-piperidinyl)ethyl]thio-10,11-dihydro -5 H-dibenzo[a,d]cyclohepten-3-carboxylate (Compound 101a)

EXAMPLE 17

Methyl 5-[2-(4-benzyl-1-piperidinyl)ethyl]thio- 5 H-dibenzo-[a,d]cyclohepten -3-carboxylate (Compound 103a)

EXAMPLE 18

Methyl (E,Z)-11-[3-(4-benzyl-1-piperazinyl)-propylidene]-6,11-dihydrodibenz[b,e]oxepin-2-carboxylate (Compound E/Z-85a)

The objective compound was prepared using Compound t obtained in Reference Example 20 and 4-benzylpiperidine in a manner similar to Example 1. A ratio of E/Z was 1:1.

In Examples 19 through 22 below, the objective compound was prepared using the corresponding starting material c or e and the corresponding piperazine or piperidine compound in a manner similar to Example 1.

EXAMPLE 19

Methyl (E)-11-[2-[4-(4-fluorophenyl-1-piperazinyl)ethylidene]-6,11-dihydrodibenz[b,e]oxepin-2-carboxylate (Compound E-73a)

EXAMPLE 20

Methyl (E,Z)-11-[2-[4-(2-pyrimidyl)-1-piperazinyl]ethylidene]-6,11-dihydrodibenz[b,e]oxepin-2-carboxylate (Compound E/Z-76a)

EXAMPLE 21

Methyl (E)-11-[2-(4-benzyl-1-piperidinyl)ethylidene]-6,11-dihydrodibenz [b,e]oxepin-2-acetate (Compound E-96a)

EXAMPLE 22

Methyl (E)-11-[2-[4-[2(3 H)-benzimidazolon-1-yl]piperidino]-ethylidene]-6,11-dihydrodibenz[b,e]oxepin-2-acetate (Compound E-98a)

Physicochemical properties of compounds obtained in Examples 1 through 22 are shown in Table 7-1. In Tables 7-1 to 7-5, symbol * in solvent for recrystallization means solidification by tritylation.

TABLE 7-1

| Example No. (Compound No.) | Appearance | MP (°C.) [Solvent for recrystallization] | NMR (solvent) δ, ppm | IR (method) cm$^{-1}$ | MS m/z | Elemental analysis (%) Upper column: found Lower column: calcd. | | |
|---|---|---|---|---|---|---|---|---|
| 1 (1a) | white crystal | 129–130 [isopropanol] | (CDCl$_3$) 2.30–3.34(m, 12H), 3.82 (s, 1H), 5.03(s, 1H), 4.83&6.39 (ABq, J=13.1Hz, 2H), 6.30–8.06 (m, 12H) | (KBr tablet) 3450, 2948, 2826, 1711, 1610, 1598, 1242 | 474 (M+) | C$_{28}$H$_{30}$N$_2$O$_3$S C 71.11 70.86 | H 6.23 6.37 | N 5.80 5.90 |
| 2 (1a') | white crystal | 188 (dec.) [isopropanol] | — | (KBr tablet) 1714, 1599, 1494, 1118, 1006 | — | C$_{28}$H$_{32}$Cl$_2$N$_2$O$_3$S C 61.75 61.42 | H 6.21 5.89 | N 5.15 5.12 |
| 3 (8a) | yellow amorphous | — | (CDCl$_3$) 2.4–3.3(m, 12H), 3.81 (s, 3H), 3.83(s, 3H), 4.86&6.41 (ABq, J=11.7Hz, 2H), 5.03(s, 1H), 6.7–7.4(m, 8H), 7.67(dd, J=2.5, 8.5Hz, 1H), 7.88(d, J=2.5Hz, 1H) | (CHCl$_3$) 2824, 1713, 1611, 1508, 1294, 1132, 1120, 1005 | 492 (M+) | — | | |
| 4 (9a) | colorless oil | — | (CDCl$_3$) 2.4–3.3(m, 12H), 3.81 (s, 3H), 3.83(s, 3H), 4.85&6.44 (ABq, J=12.8Hz, 2H), 5.07(s, 1H), 6.7–7.4(m, 9H), 7.76(dd, J=2.3, 8.5Hz, 1H), 7.98(d, J=2.3Hz, 1H) | (CHCl$_3$) 2936, 2806, 1708, 1610, 1496, 1005 | 504 (M+) | — | | |
| 5 (11a) | colorless oil | — | (CDCl$_3$) 2.05–2.65(m, 12H), 3.46 (s, 2H), 3.83(s, 3H), 4.86&6.45 (ABq, J=12.0Hz, 2H), 5.06(s, 1H), 6.98–7.44(m, 9H), 7.78(dd, J=2.2, 8.6Hz, 1H), 7.98(d, J=2.2Hz, 1H) | (CHCl$_3$) 2816, 1714, 1611, 1120, 1006 | 487 (M+) | — | | |
| 6 (15a) | colorless oil | — | (CDCl$_3$) 2.25–2.75(m, 12H), 3.36 (s, 2H), 3.81(s, 3H), 4.82&6.40 (ABq, J=12.2Hz, 2H), 5.03(s, 1H), 5.85(s, 2H), 6.55–6.8(m, 3H), 6.82(d, J=4.6Hz, 1H), 7.1–7.35 (m, 4H), 7.72(dd, J=2.5, 8.5Hz, 1H), 7.93(d, J=2.5Hz, 1H) | (CHCl$_3$) 1702, 1602, 1296, 1121, 1004 | 532 (M+) | — | | |
| 7 (16a) | colorless oil | — | (CDCl$_3$) 3.84(s, 3H), 4.20(s, 1H), 4.87&6.43(ABq, J=12.7Hz, 2H), 5.07(s, 1H), 6.84(d, J=8.6 Hz, 1H), 7.78(dd, J=2.2, 8.6Hz, 1H), 7.97(d, J=2.2Hz, 1H) | (CHCl$_3$) 1715, 1610, 1495, 1241, 1117, 1005 | 564 (M+) | — | | |
| 8 (37a) | colorless oil | — | (CDCl$_3$) 1.5–3.2(m, 13H), 3.84 (s, 3H), 4.95&6.50(ABq, J=12.7 Hz, 2H), 5.14(s, 1H), 6.87(d, J=8.5Hz, 1H), 7.05–7.45(m, 9H), 7.81(dd, J=2.2, 8.5Hz, 1H), 8.03 (d, J=2.2Hz, 1H) | (CHCl$_3$) 1719, 1609, 1496, 1247, 1128, 1009 | 473 (M+) | — | | |
| 9 (38a) | colorless oil | — | (CDCl$_3$) 1.0–2.2(m, 7H), 2.2–3.2 (m, 8H), 3.83(s, 3H), 4.85&6.41 | (CHCl$_3$) 2924, 1713, | 487 (M+) | — | | |

TABLE 7-1-continued

| Example No. (Compound No.) | Appearance | MP (°C.) [Solvent for recrystallization] | NMR (solvent) δ, ppm | IR (method) cm⁻¹ | MS m/z | Elemental analysis (%) Upper column: found Lower column: calcd. |
|---|---|---|---|---|---|---|
| | | | (ABq, J=13.9Hz, 2H), 5.06(s, 1H), 6.8–7.4(m, 10H), 7.75(dd, J=2.0, 8.5Hz, 1H), 7.95(d, J=2.0Hz, 1H) | 1611, 1295, 1120, 1007 | | |
| 10 (47a) | colorless oil | — | (DMSO-d₆) 1.5–3.0(m, 12H), 3.82 (s, 3H), 4.12(m, 1H), 5.08&6.31 (ABq, J=12.7Hz, 2H), 5.51(s, 1H), 6.91(d, J=8.6Hz, 1H), 6.95–7.5 (m, 8H), 7.75(dd, J=2.2, 8.6Hz, 1H), 8.04(d, J=2.2Hz, 1H) | (CHCl₃) 1718, 1686, 1251, 1119, 1015 | 529 (M+) | — |
| 11 (50a) | colorless oil | — | (CDCl₃) 3.87(s, 3H), 4.90&6.45 (ABq, J=12.9Hz, 2H), 5.09(s, 1H), 6.86(d, J=8.6Hz, 1H), 7.79(dd, J=2.2, 8.6Hz, 1H), 8.00(d, J=2.2Hz, 1H) | (CHCl₃) 1715, 1610, 1247, 1117, 1005 | 489 (M+) | — |
| 12 (51a) | colorless oil | — | (CDCl₃) 1.2–2.7(m, 12H), 2.73 (s, 2H), 3.86(s, 3H), 4.88&6.44 (ABq, J=12.7Hz, 2H), 5.06(s, 1H), 6.84(d, J=8.6Hz, 1H), 7.00–7.40 (m, 9H), 7.78(dd, J=2.2, 8.6Hz, 1H), 7.98(d, J=2.2Hz, 1H) | (neat) 2916, 1696, 1609, 1570, 1491, 1113, 1008 | 503 (M+) | — |
| 13 (53a) | colorless oil | — | (CDCl₃) 1.80–3.50(m, 13H), 3.87 (s, 3H), 4.90&6.43(ABq, J=12.7 Hz, 2H), 5.09(s, 1H), 6.86(d, J= 8.6Hz, 1H), 7.20–7.35(m, 4H), 7.43(d, J=8.6Hz, 2H), 7.85(d, J=8.6Hz, 2H), 7.70–7.95(m, 2H) | (CHCl₃) 2954, 2930, 1715, 1293, 1132, 1121 | 536 (M+) | — |
| 14 (58a) | colorless oil | — | (CDCl₃) 1.6–1.8(m, 2H), 2.4–3.0 (m, 10H), 3.86(s, 3H), 4.72(s, 2H), 4.90&6.46(ABq, J=12.8Hz, 2H), 5.13(s, 1H), 6.6–7.4(m, 10H), 7.75(dd, J=2.0, 8.5H, 1H), 8.00(d, J=2.0Hz, 1H) | (CHCl₃) 2926, 1703, 1600, 1499, 1376, 1243, 1118, 1006 | 543 (M+) | — |
| 15 (41a) | colorless oil | — | (CDCl₃) 1.1–2.9(m, 15H), 1.55(s, 6H), 3.61(s, 3H), 4.99(s, 1H), 4.80&6.29(ABq, J=13.0Hz, 2H), 6.7–7.35(m, 12H) | (CHCl₃) 2922, 1726, 1496, 1265, 1147, 1124, 1105, 1013, 906 | 529 (M+) | — |
| 16 (101a) | pale yellow oil | — | (CDCl₃) 1.13–1.99(m, 9H), 2.35–2.99 (m, 8H), 3.62–3.96(m, 2H), 3.83(s, 3H), 5.16(s, 1H), 6.95–7.30 (m, 10H), 7.80(dd, J=1.5, 7.9Hz, 1H), 7.92(s, 1H) | (CHCl₃) 1717, 1301, 1280, 1105 | 485 (M+) | — |
| 17 (103a) | pale yellow oil | — | (CDCl₃) 1.11–2.03(m, 9H), 2.35 (s, 2H), 2.38–2.81(m, 4H), 3.90 (s, 3H), 5.29(s, 1H), 7.01(s, 1H), 7.02(s, 1H), 7.06–7.42(m, 10H), 7.92(dd, J=1.1, 9.7Hz, 1H), 7.99(s, 1H) | (CHCl₃) 1716, 1299, 1279, 1110 | 483 (M+) | — |
| 18 (E/Z-85a) | colorless oil | — | (CDCl₃) 0.8–2.0(m, 7H), 2.1–2.9 (m, 8H), 3.78(s, 3H), 5.18(bs, 2H), 5.65(t, J=7.0Hz; Z form), 5.99(t, J=7.0Hz; E form), 6.6–8.0 (m, 12H), 7.93(d, J=2.4Hz, 1H) | (neat) 2916, 1718, 1604, 1118, 1004 | 467 (M+) | — |
| 19 (E-73a) | colorless amorphous | — | (CDCl₃) 2.3–3.4(m, 10H), 3.83 (s, 3H), 4.7–5.6(m, 2H), 6.25(t, J=5.5Hz, 1H), 6.6–7.5(m, 9H), 7.73(dd, J=2.2, 8.6Hz, 1H), 8.00 (d, J=2.2Hz, 1H) | (KBr tablet) 1707, 1605, 1504, 1240, 1002 | 458 (M+) | — |
| 20 (E/Z-76a) | colorless oil | — | (CDCl₃) 2.35–2.7(m, 4H), 3.0–3.35 (m, 2H), 3.88(s, 3H), 3.65–4.0 (m, 4H), 4.6–5.6(m, 2H), 6.30 (t, J=6.8Hz; Z form), 6.45(t, J= 4.8Hz; E form), 6.79(d, J=8.6Hz, 1H), 7.0–7.5(m, 5H), 7.78(dd, J= 2.2, 8.6Hz, 1H), 8.05(d, J=2.2Hz, 1H), 8.27(d, J=4.6Hz, 2H) | (KBr tablet) 1713, 1585, 1357, 1244, 1002 | 442 (M+) | — |
| 21 (E-96a) | colorless oil | — | (CDCl₃) 1.0–3.2(m, 11H), 3.47 (s, 3H), 3.61(s, 3H), 4.85–5.3 (m, 2H), 6.14(t, J=6.8Hz, 1H), 6.66(d, J=9Hz, 1H), 6.8–7.34(m, 11H) | (neat) 2918, 1735, 1489, 1011 | 467 (M+) | — |
| 22 (E-98a) | colorless oil | — | (CDCl₃) 1.35–3.35(m, 11H), 3.54 (s, 2H), 3.68(s, 3H), 4.65–5.5 (m, 2H), 6.22(t, J=6.6Hz, 1H), 6.73(d, J=8.4Hz, 1H), 6.8–7.5 | (CHCl₃) 1689, 1486, 1148, 1008 | 509 (M+) | — |

TABLE 7-1-continued

| Example No. (Compound No.) | Appearance | MP (°C.) [Solvent for recrystallization] | NMR (solvent) δ, ppm | IR (method) cm$^{-1}$ | MS m/z | Elemental analysis (%) Upper column: found Lower column: calcd. |
|---|---|---|---|---|---|---|
| | | | (m, 10H) | | | |

EXAMPLE 23

11-[2-(4-Phenyl-1-piperazinyl)ethyl]thio-6,11-dihydrodibenz-[b,e]oxepin -2-carboxylic acid.monohydrate (Compound 1b′)

Compound 1a, 0.8 g, obtained in Example 1 was dissolved in a solvent mixture of 300 ml of methanol and 10 ml of water and, 80 mg of sodium hydroxide was added to the solution followed by heating under reflux for 4 hours. After allowing to cool, 4 N hydrochloric acid aqueous solution was added to the mixture to adjust pH to 7. The mixture was concentrated under reduced pressure. Precipitated crystals were taken by filtration. After washing with water, 0.7 g of the objective compound was obtained as white solid.

In Examples 24 through 30 below, the objective compound was precared by hydrolyzing esters of the corresponding oxepine derivatives in a manner similar to Example 23.

EXAMPLE 24

11-[2-[4-(4-Fluorophenyl-1-piperazinyl)ethyl]thio-6;11-dihydrodibenz [b,e]oxepin-2-carboxylic acid (Compound 8b)

EXAMPLE 25

11-[2-[4-(2-Methoxyphenyl-1-piperazinyl)ethyl]thio-6,11-dihydrodibenz [b,e]oxepin-2-carboxylic acid (Compound 9b)

EXAMPLE 26

11-[2-(4-Benzyl-1-piperazinyl)ethyl]thio-6,11-dihydro-dibenz [b,e]oxepin-2-carboxylic acid.monohydrate (Compound 11b′)

EXAMPLE 27

11-[2-(4-Piperonyl-1-piperazinyl)ethyl]thio-6,11-dihydro-dibenz [b,e]oxepin-2-carboxylic acid (Compound 15b)

EXAMPLE 28

11-[2-[4-(Diphenylmethyl)-1-piperazinyl]ethyl]thio-6,11-dihydrodibenz [b,e]oxepin-2-carboxylic acid (Compound 16b)

EXAMPLE 29

11-[2-(4-Phenyl-1-piperidinyl)ethyl]thio-6,11-dihydrodibenz -[b,e]oxepin-2-carboxylic acid.0.5 hydrate (Compound 37b′)

EXAMPLE 30

11-[2-(4-Benzyl-1-piperidinyl)ethyl]thio-6,11-dihydrodibenz -[b,e]oxepin-2-carboxylic acid (Compound 38b)

EXAMPLE 31

Sodium 11-[2-(4-Benzyl-1-piperidinyl)ethyl]thio-6,11-dihydrodibenz [b,e]oxepin-2-carboxylate (Compound 38b′)

Compound 38b, 45 g, obtained in Example 30 was suspended in 500 ml of methanol and 5.3 g of sodium methoxide was added to the suspension followed by stirring at room temperature for 4 hours. The solvent was distilled off under reduced pressure. The resulting crude product was solidified with hexane to give 47 g of the objective compound.

EXAMPLE 32

11-[2-[4-[2(3 H)-Benzimidazolon-1-yl]piperidino[ethyl]thio-6,11-dihydrodibenz[b,e]oxepin-2-carboxylic acid.0.5.iso-propanol .0.5 hydrate (Compound 47b′)

The objective compound was prepared by hydrolyzing Compound 47a obtained in Example 10 in a manner similar to Example 23.

EXAMPLE 33

Sodium 11-[2-[4-[2(3 H)-Benzimidazolon-1-yl]piperidino]-ethyl]thio-6,11-dihydrodibenz[b,e]oxepin-2-carboxylate.2.5 hydrate (Compound 47b″)

Compound 47b′ obtained in Example 32 was converted into the sodium salt in a manner similar to Example 31.

In Examples 34 through 38 below, the objective compound was prepared by hydrolyzing esters of the corresponding oxepine derivatives in a manner similar to Example 23.

EXAMPLE 34

11-[2-(4-Phenyl-4-hydroxy-1-piperidinyl)ethyl]thio-6,11-dihydrodibenz [b,e]oxepin-2-carboxylic acid.0.75 hydrate (Compound 50b′)

EXAMPLE 35

11-[2-(4-Benzyl-4-hydroxy-1-piperidinyl)ethyl]thio-6,11-dihydrodibenz [b,e]oxepin-2-carboxylic acid.0.2 isopropanol (Compound 51b′)

EXAMPLE 36

11-[2-[4-(4-Chlorobenzoyl-1-piperidinyl)ethyl]thio-6,11-dihydrodibenz [b,e]oxepin-2-carboxylic acid.0.1 isopropanol.0.5 hydrate (Compound 53b′)

EXAMPLE 37

11-[2-(1-Phenyl-1,3,8-triazaspiro[4.5]decan-4-on-8-yl) -ethyl]thio-6,11-dihydrodibenz[b,e]oxepin-2-carboxylic acid. 0.25 hydrate (Compound 58b′)

EXAMPLE 38

2-Methyl-2-[11-[2-(4-benzyl-1-piperidinyl)ethyl]thio-6,11-dihydrodibenz [b,e]oxepin-2-yl]propionate (Compound 41)

EXAMPLE 39

5-[2-(4-Benzyl-1-piperidinyl)ethyl]thio-10,11-dihydro-5 H-dibenzo [a,d]cyclohepten-3-carboxylic acid.0.5 fumarate (Compound 101b')

Compound 101a, 0.33 g, obtained in Example 16 was hydrolyzed in a manner similar to Example 23 to give 0.3 g of the corresponding Compound 101b. This compound was dissolved in 50 ml of acetone and 80 mg of fumaric acid was added to the solution followed by stirring at room temperature for 2 hours. The solvent was distilled off under reduced pressure. The resulting crude product was recrystallized from isopropanol to prepare 0.14 g of the objective compound.

EXAMPLE 40

5-[2-(4-Benzyl-1-piperidinyl)ethyl]thio-5 H-dibenzo[a,d]-cyclohepten -3-carboxylic acid.0.5 fumarate.0.5 isopropanol (Compound 103b')

The objective compound was prepared using Compound 103a obtained in Example 17 in a manner similar to Example 39.

EXAMPLE 41

(E,Z)-11-[3-(4-Benzyl-1-piperazinyl)propylidene]-6,11-dihydrodibenz [b,e]oxepin-2-carboxylic acid.1.5 hydrate (Compound 85b')

The objective compound was prepared by hydrolyzing Compound E/Z-85a obtained in Example 18 in a manner similar to Example 23.

A ratio of E/Z was 38:62.

In Examples 42 and 43 below, the objective compound was prepared by hydrolyzing esters of the corresponding oxepine derivatives in a manner similar to Example 23.

EXAMPLE 42

(E)-11-[2-[4-(4-Fluorophenyl)-1-piperazinyl]ethylidene]-6,11-dihydrodibenz[b,e]oxepin-2-carboxylic acid.isopropanol. monohydrate (Compound E-73b')

EXAMPLE 43

(E,Z)-11-[2-[4-(2-Pyrimidyl)-1-piperazinyl)ethylidene]-6,11-dihydrodibenz [b,e]oxepin-2-carboxylic acid (Compound E/Z-76b)

A ratio of E/Z was 85:15.

EXAMPLE 44

(E)-11-[2-(4-Benzyl-1-piperidinyl)ethylidene]-6,11-dihydro-dibenz [b,e]oxepin-2-acetic acid.0.5 fumarate (Compound E-96b')

Compound E-96a, 2.0 g, obtained in Example 21 was hydrolyzed in a manner similar to Example 23 to give 1.7 g of the corresponding Compound E-96b. This compound was dissolved in 200 ml of acetone and 0.43 g of fumaric acid was added to the solution followed by stirring at room temperature for an hour. The precipitated crystals were taken by filtration to give 1.5 g of the objective compound.

EXAMPLE 45

(E)-11-[2-[4-[2(3 H)-Benzimidazolon-1-yl]piperidino]-ethylidene ]-6,11-dihydrodibenz[b,e]oxepin-2-acetic acid. monohydrate (Compound E-98b')

The objective compound was prepared by hydrolyzing Compound E-98a obtained in Example 22 in a manner similar to Example 23.

EXAMPLE 46

Sodium (E)-11-[2-[4-[2(3 H)-benzimidazolon-1-yl]piperidino]-ethylidene]-6,11-dihydrodibenz[b,e]oxepin-2-acetate (Compound E-98b'')

Compound E-98b' obtained in Example 45 was converted into the sodium salt in a manner similar to Example 31.

Physicochemical properties of the compounds obtained in Examples 23 through 46 are shown in Table 7-2.

TABLE 7-2

| Example No. (Compound No.) | Appearance | MP (°C.) [Solvent for recrystallization] | NMR (solvent) δ, ppm | IR (method) cm$^{-1}$ | MS m/z | Elemental analysis (%) Upper column: found Lower column: calcd. | | |
|---|---|---|---|---|---|---|---|---|
| 23 (1b') | white crystal | 215 (dec.) [isopropanol] | (DMSO-d$_6$) 2.50–3.83(m, 12H), 5.08&6.23(ABq, J=12.5Hz, 2H), 5.51(s, 1H), 6.79–8.04(m, 12H) | (KBr tablet) 3400, 2936, 2824, 1694, 1599, 1232, | 460 (M+) | C$_{27}$H$_{28}$N$_2$O$_3$S.H$_2$O | | |
| | | | | | | C | H | N |
| | | | | | | 67.39 | 6.06 | 5.59 |
| | | | | | | 67.76 | 6.32 | 5.85 |
| 24 (8b) | white amorphous | 165–166 (dec.) [isopropanol]* | (DMSO-d$_6$) 2.3–2.8(m, 8H), 3.0–3.1 (m, 4H), 5.05&6.28(ABq, J= 12.6Hz, 2H), 5.45(s, 1H), 6.85–7.1 (m, 5H), 7.4–7.5(m, 4H), 7.71 (dd, J=2.2, 8.7Hz, 1H), 7.99(d, J=2.2Hz, 1H) | (KBr tablet) 3400, 1607, 1509, 1384, 1232 | 478 (M+) | C$_{27}$H$_{27}$FN$_2$O$_3$S | | |
| | | | | | | C | H | N |
| | | | | | | 67.55 | 5.65 | 5.58 |
| | | | | | | 67.76 | 5.69 | 5.85 |
| 25 (9b) | white amorphous | 171–175 [isopropanol]* | (DMSO-d$_6$) 3.0–3.7(m, 12H), 3.81 (s, 3H), 5.10&6.16(ABq, J=12.9 Hz, 2H), 5.54(s, 1H), 6.90(d, J=8.5Hz, 1H), 6.9–7.1(m, 4H), 7.4–7.65(m, 4H), 7.74(dd, J=2.2, 8.5Hz, 1H), 8.06(d, J=2.2Hz, 1H) | (KBr tablet) 1694, 1609, 1499, 1455, 1200, 1115, 1013 | 490 (M+) | C$_{28}$H$_{30}$N$_2$O$_4$S | | |
| | | | | | | C | H | N |
| | | | | | | 68.23 | 6.35 | 5.88 |
| | | | | | | 68.55 | 6.16 | 5.71 |
| 26 (11b') | white crystal | 112–115 (dec.) [iso- | (DMSO-d$_6$) 2.2–2.7(m, 12H), 3.42 (s, 2H), 5.01&6.24(ABq, J=12.7 Hz, 2H), 5.39(s, 1H), 6.81(d, J= | (KBr tablet) 3400, 1609, 1384, 1232, | 474 (M+) | C$_{28}$H$_{30}$N$_2$O$_3$S.H$_2$O | | |
| | | | | | | 68.33 | 6.25 | 5.54 |

TABLE 7-2-continued

| Example No. (Compound No.) | Appearance | MP (°C.) [Solvent for recrystallization] | NMR (solvent) δ, ppm | IR (method) cm$^{-1}$ | MS m/z | Elemental analysis (%) Upper column: found Lower column: calcd. | | |
|---|---|---|---|---|---|---|---|---|
| | | propyl ether] | 8.6Hz, 1H), 7.2–7.5(m, 9H), 7.69 (dd, J=2.2, 8.6Hz, 1H), 7.95(d, 2.2Hz, 1H) | 1008 | | 68.27 | 6.55 | 5.69 |
| 27 (15b) | white crystal | 218–220 (dec.) [isopropanol] | (DMSO-d$_6$) 2.2–2.7(m, 12H), 3.34 (s, 2H), 5.04&6.26(ABq, J=12.7 Hz, 2H), 5.43(s, 1H), 5.98(s, 2H), 6.72(d, J=7.9Hz, 1H), 6.8–6.85 (m, 2H), 6.86(d, J=8.6Hz, 1H), 7.35–7.5(m, 4H), 7.71(dd, J=2.2, 8.6Hz, 1H), 7.98(d, J=2.2Hz, 1H) | (KBr tablet) 1670, 1609, 1491, 1242, 1040 | 518 (M+) | C$_{29}$H$_{30}$N$_2$O$_5$S C    H    N 67.09  5.95  5.24 67.16  5.83  5.40 | | |
| 28 (16b) | white crystal | 145–148 [isopropanol] | (DMSO-d$_6$) 2.2–2.7(m, 12H), 4.26 (s, 1H), 5.04&6.23(ABq, J=12.6 Hz, 2H), 5.44(s, 1H), 6.86(d, J=8.6Hz, 1H), 7.70(dd, J=2.2, 8.6Hz, 1H), 7.98(d, J=2.2Hz, 1H) | (KBr tablet) 1683, 1608, 1493, 1451, 1232, 1006 | 550 (M+) | C$_{34}$H$_{34}$N$_2$O$_3$S C    H    N 73.98  6.35  5.00 74.15  6.22  5.09 | | |
| 29 (37b') | white crystal | 182–184 [isopropanol] | (DMSO-d$_6$) 1.65–3.0(m, 13H), 5.06 &6.27(ABq, J=12.7Hz, 2H), 5.48 (s, 1H), 6.88(d, J=8.5Hz, 1H), 7.15–7.5(m, 9H), 7.72(dd, J=2.2, 8.5Hz, 1H), 8.01(d, J=2.2Hz, 1H) | (KBr tablet) 1680, 1605 1494, 1318, 1233, 1104, 1007 | 459 (M+) | C$_{28}$H$_{29}$NO$_3$S.0.5H$_2$O C    H    N 71.85  6.23  2.98 71.77  6.45  2.99 | | |
| 30 (38b) | white crystal | 205–206 [isopropanol] | (DMSO-d$_6$) 1.0–1.9(m, 7H), 2.2–2.85 (m, 8H), 5.03&6.25(ABq, J= 12.6Hz, 2H), 5.42(s, 1H), 6.86 (d, J=8.6Hz, 1H), 7.1–7.5(m, 9H), 7.70(dd, J=2.2, 8.6Hz, 1H), 7.97 (d, J=2.2Hz, 1H) | (KBr tablet) 2912, 1687, 1608, 1494, 1449, 1323, 1229, 1019 | 473 (M+) | C$_{26}$H$_{31}$NO$_3$S C    H    N 73.48  6.72  2.92 73.54  6.60  2.96 | | |
| 31 (38b') | white solid | 119–121 [hexane]* | — | (KBr tablet) 2918, 1612, 1582, 1548, 1385, 1252, 1227, 1105, 1011 | — | C$_{29}$H$_{30}$NO$_3$SNa.0.5H$_2$O C    H    N 68.80  6.44  2.93 69.03  6.19  2.78 | | |
| 32 (47b') | white crystal | 185–188 [acetonitrile/ isopropanol] | (DMSO-d$_6$) 1.55–3.1(m, 12H), 4.14(m, 1H), 5.07&6.28(ABq, J= 12.7Hz, 2H), 5.48(s, 1H), 6.89 (d, J=8.6Hz, 1H), 6.95–7.5(m, 8H), 7.72(dd, J=2.2, 8.6Hz, 1H), 8.06(d, J=2.2Hz, 1H), 10.83(s, 1H) | (KBr tablet) 1695, 1485, 1386 | 515 (M+) | C$_{29}$H$_{29}$N$_3$O$_4$S.0.5C$_3$H$_8$O. 0.5C$_2$H$_3$N C    H    N 66.41  5.90  8.45 66.75  6.22  8.57 | | |
| 33 (47b'') | white crystal | 224–227 [methanol] | — | (KBr tablet) 1683, 1583, 1543, 1485, 1379, 1256, 1229, 1109, 1006 | — | C$_{29}$H$_{28}$N$_3$O$_4$SNa.2.5H$_2$O C    H    N 59.77  5.72  7.10 59.78  5.71  7.21 | | |
| 34 (50b') | white crystal | 150–154 [isopropanol] | (DMSO-d$_6$) 1.5–1.6(m, 2H), 1.8–2.0 (m, 2H), 2.35–2.75(m, 8H), 5.05&6.28(ABq, J=12.7Hz, 2H), 6.87(d, J=8.5Hz, 1H), 7.15–7.5 (m, 9H), 7.71(dd, J=2.1, 8.5Hz, 1H), 8.01(d, J=2.1Hz, 1H) | (KBr tablet) 1611, 1584, 1550, 1375, 1228, 1006 | 475 (M+) | C$_{28}$H$_{29}$NO$_4$S.0.75H$_2$O C    H    N 68.60  6.41  2.88 68.76  6.29  2.86 | | |
| 35 (51b') | white crystal | 232 [isopropanol] | (DMSO-d$_6$) 1.25–1.5(m, 4H), 2.2–2.75 (m, 8H), 2.63(s, 2H), 5.02& 6.25(ABq, J=12.6Hz, 2H), 5.41(s, 1H), 6.85(d, J=8.6Hz, 1H), 7.15–7.45 (m, 9H), 7.70(dd, J=2.2, 8.6 Hz, 1H), 7.96(d, J=2.2Hz, 1H) | (KBr tablet) 1608, 1492, 1383, 1232, 1107, 1009 | 489 (M+) | C$_{29}$H$_{31}$NO$_4$S.0.2C$_3$H$_8$O C    H    N 70.98  6.43  2.49 70.87  6.55  2.79 | | |
| 36 (53b') | pale yellow solid | 138–139 [isopropyl ether]* | (DMSO-d$_6$) 1.4–3.5(m, 13H), 5.05 &6.27(ABq, J=12.6Hz, 2H), 5.46 (s, 1H), 6.87(d, J=8.6Hz, 1H), 7.35–7.5(m, 4H), 7.59(d, J=8.6Hz, 2H), 7.71(dd, J=2.1, 8.6Hz, 1H), 7.97(d, J=8.6Hz, 2H), 7.99(d, J=2.1Hz, 1H) | (KBr tablet) 1676, 1608, 1587, 1376, 1229, 1091, 1009 | 522 (M+) | C$_{29}$H$_{28}$ClNO$_4$S.0.1 C$_6$H$_{14}$O.0.5H$_2$O C    H    N 65.81  5.39  2.22 65.46  5.68  2.58 | | |
| 37 (58b') | white solid | 186–189 [isopropanol] | (DMSO-d$_6$) 1.56(d, J=13.6Hz, 2H), 2.4–2.9(m, 10H), 4.57(s, 2H), 5.06&6.26(ABq, J=12.6Hz, 2H), 5.54(s, 1H), 6.75–7.2(m, 5H), 6.88(d, J=8.5Hz, 1H), 7.72(dd, J=2.1, 8.5Hz, 1H), 8.04(d, J= 2.1Hz, 1H), 8.64(s, 1H) | (KBr tablet) 1710, 1598, 1497, 1379, 1105, 1009 | 529 (M+) | C$_{30}$H$_{31}$N$_3$O$_4$S.0.25H$_2$O C    H    N 67.29  5.82  7.69 67.46  5.94  7.87 | | |
| 38 (41b) | white solid | 84–86 [water]* | (DMSO-d$_6$) 1.1–1.3(m, 2H), 1.35–1.6 (m, 3H), 1.43&1.45(each s, 6H), 1.85–2.0(m, 2H), 2.35–2.9 (m, 8H), 5.33(s, 1H), 4.91&6.13 (ABq, J=12.8Hz, 2H), 6.76(d, J= | (KBr tablet) 2926, 1720, 1496, 1453, 1231, 1123, 1014 | 515 (M+) | C$_{32}$H$_{37}$NO$_3$S C    H    N 74.21  7.45  2.66 74.53  7.23  2.72 | | |

TABLE 7-2-continued

| Example No. (Compound No.) | Appearance | MP (°C.) [Solvent for recrystallization] | NMR (solvent) δ, ppm | IR (method) cm$^{-1}$ | MS m/z | Elemental analysis (%) Upper column: found Lower column: calcd. |
|---|---|---|---|---|---|---|
| 39 (101b') | pale yellow crystal | 127–130 [isopropanol] | (CD$_3$OD) 1.20–1.86(m, 5H), 2.35–3.20 (m, 12H), 3.56–3.94(m, 2H), 5.21(s, 1H), 7.03–7.33(m, 10H), 7.75–7.86(m, 2H) 8.4Hz, 1H), 7.1–7.45(m, 11H) | (KBr tablet) 3420, 2920, 1695, 1585, 1453, 1372, 1244 | 469 (M+) | C$_{30}$H$_{31}$NO$_2$S.0.5C$_4$H$_4$O$_4$<br>C  H  N<br>72.60  6.60  2.55<br>72.84  6.30  2.65 |
| 40 (103b') | pale yellow crystal | 100–115 (dec.) [isopropanol] | (DMSO-d$_6$) 1.18–2.11(m, 5H), 2.26–2.60 (m, 8H), 2.63–2.92(m, 2H), 5.44(s, 1H), 6.99(s, 2H), 7.01–7.49 (m, 10H), 7.84(dd, J=1.3, 9.0Hz, 1H), 8.02(s, 1H) | (KBr tablet) 3400, 2922, 1698, 1582, 1372 | 467 (M+) | C$_{30}$H$_{29}$NO$_2$S.0.5C$_4$H$_4$O$_4$.<br>0.5C$_3$H$_8$O<br>C  H  N<br>72.23  6.51  2.41<br>72.41  6.35  2.52 |
| 41 (E/Z-85b') | white solid | 146–149 [water]* | (DMSO-d$_6$) 5.70(t, J=6.7Hz; Z form), 6.06(t, J=7.5Hz; E form), 6.80(d, J=8.4Hz; E form), 6.88 (d, J=8.6Hz; Z form), 7.76(d, J=2.2Hz; Z form), 7.87(d, J=2.0Hz; E form) | (KBr tablet) 2920, 1605, 1486, 1454, 1367, 1242, 1004 | 453 (M+) | C$_{30}$H$_{31}$NO$_3$.1.5H$_2$O<br>C  H  N<br>75.09  7.22  2.82<br>74.97  7.13  2.91 |
| 42 (E-73b') | white crystal | 236–238 (dec.) [isopropanol] | (DMSO-d$_6$) 2.4–3.7(m, 10H), 4.95–5.65 (m, 2H), 6.17(t, J=6.7Hz, 1H), 6.83(d, J=8.5Hz, 1H), 6.85–7.55 (m, 8H), 7.72(dd, J=2.2, 8.5Hz, 1H), 7.92(d, J=2.2Hz, 1H) | (KBr tablet) 1608, 1509, 1370, 1224 | 444 (M+) | C$_{27}$H$_{25}$FN$_2$O$_3$.C$_3$H$_8$O.<br>H$_2$O<br>C  H  N<br>69.10  6.60  5.33<br>68.95  6.75  5.36 |
| 43 (E/Z-76b) | pale yellow crystal | 161–165 [isopropanol] | (DMSO-d$_6$) 2.3–3.8(m, 10H), 4.9–5.65 (m, 2H), 5.86(t, J=7.1Hz; Z form), 6.18(t, J=6.6Hz; E form), 6.6–8.4(m, 10H) | (KBr tablet) 1584, 1551, 1487, 1450, 1360 | 428 (M+) | C$_{25}$H$_{24}$N$_4$O$_3$<br>C  H  N<br>69.91  5.78  13.22<br>70.08  5.65  13.08 |
| 44 (E-96b') | white solid | 203–204.5 [acetone]* | (DMSO-d$_6$) 1.1–2.55(m, 9H), 2.46 (d, J=6.6Hz, 2H), 2.92(d, J=6.6 Hz, 1H), 3.48(s, 2H), 4.0–5.5(m, 2H), 6.08(t, J=6.6Hz, 1H), 6.57 (s, 1H), 6.67(d, J=8.4Hz, 1H), 7.0–7.5(m, 11H) | (KBr tablet) 1704, 1488, 1357, 1249, 1227, 1003 | 453 (M+) | C$_{30}$H$_{31}$NO$_3$.0.5C$_4$H$_4$O$_4$<br>C  H  N<br>74.92  6.64  2.79<br>75.12  6.50  2.74 |
| 45 (E-98b') | white solid | 260–262 [isopropanol]* | (DMSO-d$_6$) 1.5–3.6(m, 10H), 3.51 (s, 2H), 4.05–4.2(m, 1H), 4.93& 5.40(each bs, 2H), 6.13(t, J=6.7 Hz, 1H), 6.68(d, J=8.5Hz, 1H), 6.95–7.5(m, 10H) | (KBr tablet) 1699, 1489, 1386, 1003 | 495 (M+) | C$_{30}$H$_{29}$N$_3$O$_4$.H$_2$O<br>C  H  N<br>70.31  6.45  8.35<br>70.16  6.08  8.18 |
| 46 (E-98b'') | white crystal | 218–219.5 [isopropanol] | (DMSO-d$_6$) 1.5–2.5(m, 4H), 2.9–3.4 (m, 6H), 3.15(s, 2H), 4.0–4.15 (m, 1H), 4.2–5.6(m, 2H), 6.10(t, J=6.7Hz, 1H), 6.57(d, J=8.3Hz, 1H), 6.9–7.5(m, 10H), 8.29(s, 1H) | (KBr tablet) 1681, 1567, 1485, 1381, 1009 | — | C$_{30}$H$_{28}$N$_3$O$_4$Na<br>C  H  N<br>69.66  5.52  8.22<br>69.62  5.45  8.12 |

EXAMPLE 47

Methyl 11-[2-(4-cinnamyl-1-piperazinyl)ethyl]thio-6,11-dihydrodibenz [b,e]oxepin-2-carboxylate (Compound 20a)

Compound k, 2.0 g, obtained in Reference Example 11 and 1.2 g of cinnamyl bromide were stirred in 100 ml of isopropanol for 4 hours at room temperature. The mixture was extracted with 300 ml of ethyl acetate. The extract was washed in succession with saturated sodium bicarbonate aqueous solution and saturated sodi=chloride aqueous solution. After drying over anhydrous sodium sulfate, the solvent was distilled off under reduced pressure. The obtained residue was purified by silica gel column chromatography (eluent; hexane:ethyl acetate:triethylamine=10:10:1) to give 0.8 g of the objective compound as pale yellow oil.

EXAMPLE 48

Methyl (E)-11-[3-(4-cinnamyl-1-piperazinyl)ethylidene]-6,11-dihydrodibenz[b,e]oxepin-2-carboxylate (Compound E-75a)

The objective compound was prepared using Compound s obtained in Reference Example 19 and cinnamyl bromide in a manner similar to Example 47.

In Examples 49 and 50 below, the objective compound was prepared by hydrolyzing esters of the corresponding oxepine derivatives and then converting the hydrolyzate into the fumarate in a manner similar to Example 44.

EXAMPLE 49

11-[2-(4-Cinnamyl-1-piperazinyl)ethyl]thio-6,11-dihydrodibenz [b,e]oxepin-2-carboxylic acid.difumarate.0.5 hydrate (Compound 20b')

EXAMPLE 50

(E)-11-[3-(4-Cinnamyl-1-piperazinyl)ethylidene]-6,11-dihydrodibenz[b,e]oxepin-2-carboxylic acid.difumarate-0.5 hydrate (Compound E-75b')

Physicochemical properties of the compounds obtained in Examples 47 to 50 are shown in Table 7-3.

TABLE 7-3

| Example No. (Compound No.) | Appearance | MP (°C.) [Solvent for recrystallization] | NMR (solvent) δ, ppm | IR (method) cm$^{-1}$ | MS m/z | Elemental analysis (%) Upper column: found Lower column: calcd. |
|---|---|---|---|---|---|---|
| 47 (20a) | pale yellow oil | — | (CDCl$_3$) 2.32–2.80(m, 12H), 3.14 (d, J=5.6Hz, 2H), 3.89(s, 3H), 4.89&6.45(ABq, J=14.5Hz, 2H), 5.10(s, 1H), 6.21–8.10(m, 14H) | (neat) 2944, 2808, 1708, 1610, 1571, 1497, 1007 | 514 (M+) | — |
| 48 (E-75a) | colorless oil | — | (CDCl$_3$) 2.48(m, 8H), 3.0–3.3(m, 4H), 3.81(s, 3H), 4.9–5.7(m, 2H), 6.05–6.5(m, 2H), 6.71(d, J=9.2Hz, 1H), 7.0–7.5(m, J=9.2Hz, 9H), 7.73(dd, J=2.2, 9.2Hz, 1H), 7.99 (d, J=2.2Hz, 1H) | (neat) 1715, 1606, 1245, 1006 | 480 (M+) | — |
| 49 (20b') | yellow solid | 210–211 [acetonitrile]* | (DMSO-d$_6$) 2.35–2.7(m, 12H), 3.25 (d, J=6.6Hz, 2H), 5.05&6.25(ABq, J=10.6Hz, 2H), 5.44(s, 1H), 6.25–6.3 (m, 1H), 6.87(d, J=8.5Hz, 1H), 7.2–7.5(m, 1H), 7.71(dd, J=2.2, 8.5Hz, 1H), 7.98(d, J=2.2Hz, 1H) | (KBr tablet) 1713, 1612, 1300, 1252, 1170 | 500 (M+) | C$_{38}$H$_{40}$N$_2$O$_{11}$S.0.5H$_2$O<br>C  H  N<br>61.48 5.42 3.88<br>61.53 5.57 3.78 |
| 50 (E-75b') | white crystal | 246 (dec.) [acetonitrile] | (DMSO-d$_6$) 2.4–3.3(m, 10H), 3.24 (d, J=6.7Hz, 2H), 4.9–5.7(m, 2H), 6.14(t, J=6.7Hz, 1H), 6.2–6.35 (m, 1H), 6.82(d, J=8.5Hz, 1H), 7.2–7.55(m, 10H), 7.72(dd, J= 2.2, 8.5Hz, 1H), 7.90(d, J=2.2Hz, 1H) | (KBr tablet) 1703, 1659, 1605, 1250, 1010, 980 | 466 (M+) | C$_{38}$H$_{38}$N$_2$O$_{11}$.0.5H$_2$O<br>C  H  N<br>64.53 5.43 4.05<br>64.49 5.55 3.96 |

EXAMPLE 51

Methyl 11-[2-[4-(4-fluorophenylsulfonyl)-1-piperazinyl]-ethyl]thio-6,11-dihydrodibenz[b,e]oxepin-2-carboxylate (Compound 22a)

Compound k, 0.8 g, obtained in Reference Example 11 was dissolved in 50 ml of pyridine and 0.5 g of 4-fluorobenzenesulfonyl chloride was added to the solution followed by stirring at room temperature for 2 hours. The solvent was distilled off under reduced pressure. The residue was extracted with 200 ml of ethyl acetate. The extract was washed in succession with saturated sodium bicarbonate aqueous solution and saturated sodium chloride aqueous solution. After drying over anhydrous magnesium sulfate, the solvent was distilled off under reduced pressure. The obtained residue was subjected to silica gel column chromatography (eluent; hexane:ethyl acetate:triethylamine=50:20:1) to give 0.6 g of the crude product. The crude product obtained was recrystallized from isopropyl ether to give 0.4 g of the objective compound.

In Examples 52 and 53 below, the objective compound was prepared using Compound k and the corresponding sulfonyl chloride compound in a manner similar to Example 51.

EXAMPLE 52

Methyl 11-[2-[4-(styrylsulfonyl)-1-piperazinyl]ethyl]thio -6,11-dihydrodibenz[b,e]oxepin-2-carboxylate (Compound 24a)

EXAMPLES 53

Methyl 11-[2-[4-(2-thienylsulfonyl)-1-piperazinyl]ethyl]-thio-6,11-dihydrodibenz[b,e]oxepin-2-carboxylate (Compound 25a)

In Examples 54 and 55 below, the objective compound was prepared using Compound k and the corresponding acid chloride compound in a manner similar to Example 51.

EXAMPLE 54

Methyl 11-[2-[4-(2,3,4-trimethoxybenzoyl)-1-piperazinyl]-ethyl]thio-6,11-dihydrodibenz[b,e]oxepin-2-carboxylate (Compound 27a)

EXAMPLE 55

Methyl 11-[2-[4-(cinnamoyl)-1-piperazinyl]ethyl]thio-6,11-dihydrodibenz[b,e]oxepin-2-carboxylate (Compound 28a)

EXAMPLE 56

Methyl 11-[2-[4-(phenoxycarbonyl)-1-piperazinyl]ethyl]thio -6,11-dihydrodibenz[b,e]oxepin-2-carboxylate (Compound 30a)

Compound k, 2.0 g, obtained in Reference Example 11 was dissolved in 100 ml of isopropanol and 0.75 ml of phenyl chloroformate was added to the solution followed by stirring at room temperature for 4 hours. The solvent was distilled off under reduced pressure and the resulting residue was extracted with 200 ml of ethyl acetate. The extract was washed in succession with saturated sodium bicarbonate aqueous solution and saturated sodium chloride aqueous solution. After drying over anhydrous magnesium sulfate, the solvent was distilled off under reduced pressure. The obtained residue was subjected to silica gel column chromatography (eluent; hexane:ethyl acetate:triethylamine=50:30:1) to give 1.7 g of the crude product. The crude product obtained was solidified with isopropyl ether to give 1.6 g of the objective compound.

EXAMPLE 57

Methyl 11-[2-[4-(benzyloxycarbonyl)-1-piperazinyl]ethyl]-thio-6,11-dihydrodibenz[b,e]oxepin-2-carboxylate (Compound 31a)

The objective compound was prepared using Compound k and benzyl chloroformate in a manner similar to Example 56.

In Examples 58 and 59 below, the objective compound was prepared from Compound s obtained in Reference Example 19 and the corresponding sulfonyl chloride compound in a manner similar to Example 51.

EXAMPLE 58

Methyl (E)-11-[2-[4-(styrylsulfonyl)-1-piperazinyl]-ethylidene]-6,11-dihydrodibenz[b,e]oxepin-2-carboxylic acid (Compound E-78a)

EXAMPLE 59

Methyl (E)-11-[2-[4-(2-thienylsulfonyl)-1-piperazinyl]-ethylidene]-6,11-dihydrodibenz[b,e]oxepin-2-carboxylic acid (Compound E-79a)

EXAMPLE 60

Methyl 11-[2-[4-(1-naphthalenesulfonyl)-1-homopiperazinyl]-ethyl]thio-6,11-dihydrodibenz[b,e]oxepin-2-carboxylate (Compound 34a)

The objective compound was prepared using 1.4 g of Compound u obtained in Reference Example 21 and 1.0 g of 1-naphthalenesulfonyl chloride in a manner similar to Example 51.

Physicochemical properties of the compounds obtained in Examples 51 to 60 are shown in Table 7-4.

TABLE 7-4

| Example No. (Compound No.) | Appearance | MP (°C.) [Solvent for recrystallization] | NMR (solvent) δ, ppm | IR (method) cm$^{-1}$ | MS m/z | Elemental analysis (%) Upper column: found Lower column: calcd. |
|---|---|---|---|---|---|---|
| 51 (22a) | yellow amorphous | 80–82 [isopropyl ether]* | (CDCl$_3$) 2.25–3.15(m, 12H), 3.80 (s, 3H), 4.85&6.39(ABq, J=13.6 Hz, 2H), 5.00(s, 1H), 6.77(d, J= 8.6Hz, 1H), 6.95–8.0(m, 10H) | (KBr tablet) 1702, 1494, 1357, 1326, 1244, 1172, 1004 | 556 (M+) | C$_{28}$H$_{29}$FN$_2$O$_5$S$_2$<br>C    H    N<br>60.60  5.39  4.88<br>60.41  5.25  5.03 |
| 52 (24a) | colorless oil | — | (CDCl$_3$) 2.4–2.75(m, 8H), 3.15–3.35 (m, 4H), 3.79(s, 3H), 4.97 (s, 1H), 4.82&6.37(ABq, J=19.2 Hz, 2H), 6.7–6.85(m, 2H), 7.1–7.5 (m, 10H), 7.71(dd, J=3.0, 12.9Hz, 1H), 7.90(d, J=3.0Hz, 1H) | (KBr tablet) 1715, 1607, 1310, 1248, 1152, 1000 | 550 (M+) | — |
| 53 (25a) | yellow solid | 80–81 [isopropyl ether]* | (CDCl$_3$) 2.28–3.26(m, 12H), 3.81 (s, 3H), 5.00(s, 1H), 4.86&6.36 (ABq, J=13.2Hz, 2H), 6.68–7.98(m, 10H) | (KBr tablet) 1714, 1609, 1353, 1242, 1007 | 544 (M+) | C$_{26}$H$_{28}$NO$_5$S$_3$<br>C    H    N<br>57.31  5.30  5.09<br>57.33  5.18  5.14 |
| 54 (27a) | colorless oil | — | (CDCl$_3$) 2.15–2.75(m, 10H), 3.15–3.45 (m, 2H), 3.8–3.9(m, 12H), 5.04(s, 1H), 4.87&6.38(ABq, J= 17.1Hz, 2H), 6.62(d, J=12.9Hz, 1H), 6.80(d, J=12.9H, 1H), 6.91 (d, J=12.9Hz, 1H), 7.1–7.47(m, 4H), 7.74(dd, J=3.0, 12.9Hz, 1H), 7.93(d, J=3.0Hz, 1H) | (CHCl$_3$) 1713, 1613, 1461, 1295, 1120, 1009 | 592 (M+) | — |
| 55 (28a) | yellow amorphous | — | (CDCl$_3$) 2.19–2.70(m, 8H), 3.36–3.83 (m, 4H), 3.83(s, 3H), 5.03(s, 1H), 4.85&6.41(ABq, J=12.8Hz, 2H), 6.61–8.06(m, 14H) | (KBr tablet) 1711, 1645, 1606, 1245, 982 | 528 (M+) | — |
| 56 (30a) | white solid | 133–135 [isopropyl ether] | (CDCl$_3$) 2.2–2.8(m, 8H), 3.3–3.7 (m, 4H), 3.85(s, 3H), 4.87&6.43 (ABq, J=12.8Hz, 2H), 5.04(s, 1H), 6.83(d, J=8.4Hz, 1H), 6.95–7.5(m, 9H), 7.76(dd, J=2.4, 8.4Hz, 1H), 7.97(d, J=2.4Hz, 1H) | (KBr tablet) 1712, 1611, 1497, 1293, 1248, 1199, 1118 | 518 (M+) | C$_{29}$H$_{30}$N$_2$O$_5$S<br>C    H    N<br>67.00  5.90  5.12<br>67.16  5.83  5.40 |
| 57 (31a) | colorless oil | — | (CDCl$_3$) 2.05–2.8(m, 8H), 3.4–3.65 (m, 4H), 3.80(s, 3H), 4.84& 6.39(ABq, J=12.6Hz, 2H), 5.02(s, 1H), 5.08(s, 2H), 6.81(d, J=8.5 Hz, 1H), 7.0–7.5(m, 9H), 7.74 (dd, J=2.4, 8.5Hz, 1H), 7.93(d, J=2.4Hz, 1H) | (neat) 2948, 1710, 1610, 1433, 1237, 1118, 1006 | 532 (M+) | — |
| 58 (E-78a) | pale yellow crystal | 193–196 [isopropanol] | (CDCl$_3$) 2.45–2.9(m, 4H), 3.0–3.6 (m, 6H), 3.91(s, 3H), 4.7–5.7(m, 2H), 6.23(t, J=7.6Hz, 1H), 6.5–8.1 (m, 14H) | (KBr tablet) 1715, 1607, 1310, 1248, 1152, 1000, 945 | 530 (M+) | C$_{30}$H$_{30}$N$_2$O$_5$S<br>C    H    N<br>67.55  5.90  5.39<br>67.90  5.70  5.28 |
| 59 (E-79a) | colorless oil | — | (CDCl$_3$) 2.45–2.6(m, 4H), 3.0–3.3 (m, 6H), 3.86(s, 3H), 4.7–5.7 (m, 2H), 6.13(t, J=6.8Hz, 1H), 7.0–7.65(m, 7H), 7.78(dd, J=2.2, 8.6Hz, 1H), 6.77(d, J=8.6Hz, 1H), 7.98(d, J=2.2Hz, 1H) | (KBr tablet) 1711, 1605, 1351, 1241, 999 | 510 (M+) | — |
| 60 (34a) | colorless oil | — | (CDCl$_3$) 1.6–2.0(m, 2H), 2.45–2.85 (m, 8H), 3.3–3.6(m, 4H), 3.86 (s, 3H), 4.88&6.43(ABq, J=12.1 | (KBr tablet) 1713, 1609, 1321, 1243, | 602 (M+) | — |

TABLE 7-4-continued

| Example No. (Compound No.) | Appearance | MP (°C.) [Solvent for recrystallization] | NMR (solvent) δ, ppm | IR (method) cm$^{-1}$ | MS m/z | Elemental analysis (%) Upper column: found Lower column: calcd. |
|---|---|---|---|---|---|---|
| | | | Hz, 2H), 4.99(s, 1H), 7.25–8.85 (m, 13H) | 1005 | | |

In Examples 61 through 63 below, the objective compound was prepared by hydrolyzing esters of the corresponding oxepine derivatives in a manner similar to Example 23.

EXAMPLE 61

11-[2-[4-(Styrylsulfonyl)-1-piperazinyl]ethyl]thio-6,11-dihydrodibenz[b,e]oxepin-2-carboxylic acid.0.5 hydrate (Compound 24b′)

EXAMPLE 62

11-[2-[4-(2-Thienylsulfonyl)-1-piperazinyl]ethyl]thio-6,11-dihydrodibenz[b,e]oxepin-2-carboxylic acid.0.5 isopropanol.dihydrate (Compound 25b′)

EXAMPLE 63

11-[2-[4-(2,3,4-Trimethoxybenzoyl)-1-piperazinyl]ethyl]-thio-6,11-dihydrodibenz[b,e]oxepin-2-carboxylic acid (Compound 27b)

EXAMPLE 64

11-[2-[4-(2,3,4-Trimethoxybenzoyl)-1-piperazinyl]ethyl]-thio-6,11-dihydrodibenz[b,e]oxepin-2-carboxylic acid. monohydrochloride.1.1 hydrate (Compound 27b′)

The objective compound was prepared as the hydrochloride from Compound 27b obtained in Example 63 in a manner similar to Example 2.

In Examples 65 through 68 below, the objective compound was prepared by hydrolyzing esters of the corresponding oxepine derivatives in a manner similar to Example 23.

EXAMPLE 65

11-[2-[4-(Cinnamoyl)-1-piperazinyl]ethyl]thio-6,11-dihydro -dibenz[b,e]oxepin-2-carboxylic acid (Compound 28b)

EXAMPLE 66

11-2-[4-(Benzyloxycarbonyl)-1-piperazinyl]ethyl]thio-6,11-dihydrodibenz[b,e]oxepin-2-carboxylic acid.dehydrate (Compound 31b′)

EXAMPLE 67

(E)-11-[2-[4-(Styrylsulfonyl)-1-piperazinyl]ethylidene]-6,11-dihydrodibenz[b,e]oxepin-2-carboxylic acid-0.1 iso -propanol.0.1 hydrate (Compound E-78b′)

EXAMPLE 68

(E)-11-[2-[4-(2-Thienylsulfonyl)-1-piperazinyl]ethylidene]-6,11-dihydrodibenz[b,e]oxepin-2-carboxylic acid.0.5 hydrate (Compound E-79b′)

Physicochemical properties of the compounds obtained in Examples 61 to 68 are shown in Table 7-5.

TABLE 7-5

| Example No. (Compound No.) | Appearance | MP (°C.) [Solvent for recrystallization] | NMR (solvent) δ, ppm | IR (method) cm$^{-1}$ | MS m/z | Elemental analysis (%) Upper column: found Lower column: calcd. |
|---|---|---|---|---|---|---|
| 61 (24b′) | white crystal | 232–235 [isopropanol] | (DMSO-d$_6$) 2.3–2.7(m, 8H), 3.0–3.3 (m, 4H), 5.44(s, 1H), 5.10& 6.31(ABq, J=19.2Hz, 2H), 6.86(d, J=13.5Hz, 1H), 7.25–7.65(m, 10H), 7.65–7.9(m, 2H), 7.98(d, J=3.0Hz, 1H) | (KBr tablet) 1685, 1603, 1313, 1246, 1157, 1002, 957 | — | C$_{29}$H$_{30}$N$_2$O$_5$S$_2$.0.5H$_2$O<br>C  H  N<br>62.30  5.63  4.82<br>62.23  5.58  5.00 |
| 62 (25b′) | white crystal | 167–168 [isopropanol] | (DMSO-d$_6$) 2.50–3.46(m, 12H), 5.05&6.17(ABq, J=12.7Hz, 2H), 5.47(s, 1H), 6.86–8.11(m, 10H), 12.76(bs, 1H) | (KBr tablet) 3400, 2860, 1687, 1607, 1354, 1159 | 530 (M+) | C$_{25}$H$_{26}$N$_2$O$_5$S$_3$.0.5 C$_3$H$_8$O.2H$_2$O<br>C  H  N<br>53.53  5.20  4.55<br>53.34  5.41  4.69 |
| 63 (27b) | pale yellow amorphous | — | (DMSO-d$_6$) 2.85–3.65(m, 12H), 3.75–3.85(m, 9H), 5.52(s, 1H), 5.09&6.15(ABq, J=12.9Hz, 2H), 6.85–7.00(m, 3H), 7.4–7.5(m, 4H), 7.73(dd, J=2.1, 8.6Hz, 1H), 8.04(d, J=2.1Hz, 1H) | — | 578 (M+) | — |
| 64 (27b′) | white crystal | 165–168 [isopropyl ether] | — | (KBr tablet) 2934, 1583, 1462, 1227, 1011 | — | C$_{31}$H$_{34}$N$_2$O$_7$S.HCl.1H$_2$O<br>C  H  N<br>58.63  6.23  4.23<br>58.64  5.90  4.41 |
| 65 (28b) | white crystal | 218–219 [isopropanol] | (DMSO-d$_6$) 2.25–3.75(m, 12H), 5.05&6.28(ABq, J=12.5Hz, 2H), 5.45(s, 1H), 6.87(d, J=8.5Hz, 1H), 7.24(d, J=15.5Hz, 1H), 7.3–7.5 (m, 5H), 7.48(d, J=15.5Hz, 1H), 7.65–7.8(m, 3H), 8.00(d, J=2.1Hz, 1H) | (KBr tablet) 1692, 1642, 1566, 1227, 1004, 987 | 514 (M+) | C$_{30}$H$_{30}$N$_2$O$_4$S<br>C  H  N<br>69.91  5.96  5.39<br>70.02  5.88  5.44 |
| 66 (31b′) | white crystal | 207–208 [toluene] | (DMSO-d$_6$) 2.8–4.2(m, 12H), 5.12 (s, 2H), 5.09&6.15(ABq, J=12.9 Hz, 2H), 5.52(s, 1H), 6.90(d, J= | (KBr tablet) 1714, 1677, 1611, 1436, | 518 (M+) | C$_{29}$H$_{30}$N$_2$O$_5$S.2H$_2$O<br>C  H  N<br>62.43  6.51  4.96 |

TABLE 7-5-continued

| Example No. (Compound No.) | Appearance | MP (°C.) [Solvent for recrystallization] | NMR (solvent) δ, ppm | IR (method) cm⁻¹ | MS m/z | Elemental analysis (%) Upper column: found Lower column: calcd. | | |
|---|---|---|---|---|---|---|---|---|
| | | | 8.6Hz, 1H), 7.3–7.6(m, 9H), 7.73 (dd, J=2.2, 8.6Hz, 1H), 8.04(d, J=2.2Hz, 1H), 11.25(bs, 1H) | 1200, 1161, 1005 | | 62.80 | 6.18 | 5.05 |
| 67 (E-78b') | white crystal | 233–235 (dec.) [isopropanol] | (DMSO-d₆) 2.2–3.5(m, 10H), 5.00 &5.52(each bs, 2H), 6.10(t, J= 6.6Hz, 1H), 6.83(d, J=8.5Hz, 1H), 7.2–7.9(m, 11H) | (KBr tablet) 1685, 1603, 1570, 1348, 1313, 1246, 1002, 957 | 516 (M+) | C₂₉H₂₈N₂O₅S.0.5H₂O.0.1C₃H₈O | | |
| | | | | | | C | H | N |
| | | | | | | 66.37 | 5.70 | 5.11 |
| | | | | | | 66.20 | 5.65 | 5.27 |
| 68 (E-79b') | white crystal | 250–251 (dec.) [isopropanol] | (DMSO-d₆) 2.3–3.5(m, 10H), 4.99 &5.50(each bs, 2H), 6.07(bs, 1H), 6.82(d, J=8.5Hz, 1H), 7.2–7.65 (m, 6H), 7.71(dd, J=2.2, 8.5 Hz, 1H), 7.87(d, J=2.2Hz, 1H), 8.05–8.10(m, 1H) | (KBr tablet) 1685, 1607, 1353, 1316, 1246, 1166, 1009, 954 | 496 (M+) | C₂₅H₂₄N₂O₅S₂.0.5H₂O | | |
| | | | | | | C | H | N |
| | | | | | | 59.33 | 4.74 | 5.47 |
| | | | | | | 59.39 | 4.98 | 5.54 |

---

Pharmaceutical Preparation 1 Tablet
A tablet having the following composition is prepared in a conventional manner.

| | |
|---|---|
| Compound 1b' | 100 mg |
| Lactose | 60 mg |
| Potato starch | 30 mg |
| Polyvinyl alcohol | 2 mg |
| Magnesium stearate | 1 mg |
| Tar pigment | trace |

Pharmaceutical Preparation 2 Powder
Powders having the following composition are prepared in a conventional manner.

| | |
|---|---|
| Compound 38b' | 100 mg |
| Lactose | 300 mg |

Pharmaceutical Preparation 3 Syrup
Syrup having the following composition is prepared in a conventional manner.

| | |
|---|---|
| Compound 38b' | 100 mg |
| Refined sugar | 30 g |
| Ethyl p-hydroxybenzoate | 40 mg |
| Propyl p-hydroxybenzoate | 10 mg |
| Strawberry flavor | 0.1 cc |
| Water is added until the whole volume is 100 cc. | |

Pharmaceutical Preparation 4 Tablet
A tablet having the following composition is prepared in a conventional manner.

| | |
|---|---|
| Compound E-78b' | 100 mg |
| Lactose | 60 mg |
| Potato starch | 30 mg |
| Polyvinyl alcohol | 2 mg |
| Magnesium stearate | 1 mg |
| Tar pigment | trace |

Pharmaceutical Preparation 5 Syrup
Syrup having the following composition is prepared in a conventional manner.

| | |
|---|---|
| Compound E-78b' | 100 mg |
| Refined sugar | 30 g |
| Ethyl p-hydroxybenzoate | 40 mg |
| Propyl p-hydroxybenzoate | 10 mg |
| Strawberry flavor | 0.1 cc |
| Water is added until the whole volume is 100 cc. | |

While the invention has been described in detail and with reference to specific embodiments thereof, it will be apparent to one skilled in the art that various changes and modifications can be made therein without departing from the spirit and scope thereof.

What is claimed is:

1. A tricyclic compound represented by formula (I):

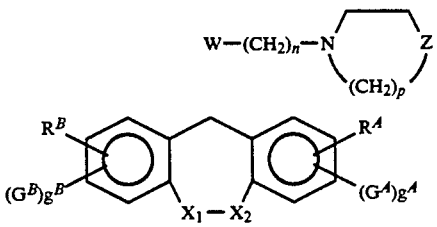

wherein == represents single bond or double bond;
$X_1$–$X_2$ represents —$CH_2$—$CH_2$—, or —CH=CH—;
W represents —S— or =CH—;
n is 1, 2, 3, or 4;
one of $R^A$ and $R^B$ represents hydrogen and the other represents —Y—M wherein Y represents single bond, —$CR^1R^2$—$(CH_2)_m$—, or —$CR^1$=C-$R^2$—$(CH_2)_m$— wherein each of $R^1$ and $R^2$ independently represents hydrogen or lower alkyl and m is 0, 1, 2, 3 or 4, in which the left side of each formula is bound to the mother nucleus; and M represents —$CONR^{3a}R^{3b}$ wherein each of $R^{3a}$ and $R^{3b}$ independently has the same significances for $R^3$ as described above, or tetrazolyl;
each of $G^A$ and $G^B$ independently represents lower alkyl, halogen, hydroxyl, or lower alkoxyl;
each of $g^A$ and $g^B$ independently represents 0, 1, 2 or 3;
Z represents

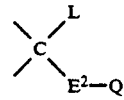

wherein Q represents aryl, aralkyl or aralkenyl which is optionally substituted with 1 to 3 substituents independently selected from the group consisting of lower alkyl, halogen, trifluoromethyl, hydroxyl, lower alkoxyl and methylene dioxy formed together with the ortho-position of the aromatic ring;
wherein L represents hydrogen, hydroxyl, or lower alkoxy; and $E^2$ represents single bond, —CO—, or

wherein $R^4$ represents hydrogen or lower alkyl;
>C=CH—Q wherein Q has the same significance as described above;
p is 1, 2 or 3;
and a pharmaceutically acceptable salt thereof.

2. A compound according to claim 1, wherein one of $R^A$ and $R^B$ represents hydrogen and the other represents —Y—COOH.

3. A compound according to claim 2, wherein Y is a member selected from the group consisting of single bond, —CH$_2$—,

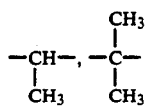

and —CH$_2$CH$_2$—.

4. A compound according to any one of claims 1-3 wherein Z is

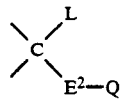

and p is 2 or 3.

5. A compound according to 4, wherein Q represents optionally substituted aryl having 6 to 10 carbon atoms, optionally substituted aralkyl having 7 to 20 carbon atoms or optionally substituted aralkenyl having 8 to 18 carbon atoms.

6. A compound according to any one of claims 1-3 wherein p is 2; and Z is

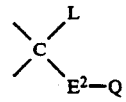

wherein L represents hydrogen or hydroxyl, $E^2$ represents single bond or —CO—, and Q is selected from the group consisting of optionally substituted phenyl, optionally substituted benzyl, optionally substituted benzhydryl, phenethyl, stryl, and cinnamyl.

7. A compound according to claim 1, wherein said salt is selected from the group consisting of acid addition salt, metal salt, ammonium salt, organic amine addition salt and amino acid addition salt.

8. 5-[2-(4-Benzyl-1-piperidinyl)ethyl]thio-5 H-dibenzo [a,d]-cyclohepten-3-carboxylic acid.

9. 5-[2-(4-Benzyl-1-piperidinyl)ethyl]thio-10, 11-dihydro-5 H-dibenzo[a,d]cyclohepten-3-carboxylic acid, or a pharmaceutically acceptable salt thereof.

10. A pharmaceutical composition comprising a pharmaceutical carrier and, as an active ingredient, an effective amount of a tricyclic compound as defined by claim 1.

* * * * *

UNITED STATES PATENT AND TRADEMARK OFFICE
CERTIFICATE OF CORRECTION

PATENT NO. : 5,302,602

DATED : April 12, 1994

INVENTORS : ETSUO OSHIMA ET AL.

It is certified that error appears in the above-identified patent and that said Letters Patent is hereby corrected as shown below:

ON THE TITLE PAGE

AT [57] ABSTRACT

Form (I), " 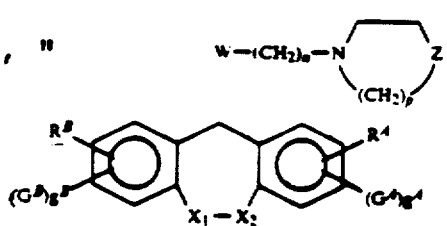 " should read

-- 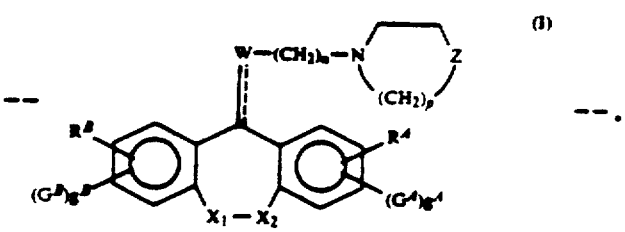 --.

COLUMN 1

Line 50, "(cf." should read --[cf.--.

UNITED STATES PATENT AND TRADEMARK OFFICE
CERTIFICATE OF CORRECTION

PATENT NO. : 5,302,602

DATED : April 12, 1994

INVENTORS : ETSUO OSHIMA ET AL.

It is certified that error appears in the above-identified patent and that said Letters Patent is hereby corrected as shown below:

COLUMN 2

Line 9, "Publisher" should read --Published--.

Line 17, " 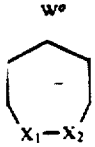 " should read -- 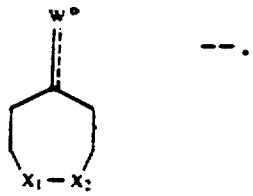 --.

COLUMN 3

Line 46, "$X_1X_2$" should read --$X_1$-$X_2$--.

COLUMN 4

Line 61, "heterocyclic," should read --heterocyclic--.

COLUMN 5

Line 41, "etc., an" should read --etc.; and--.
Line 64, "N7-" should read --N- --.

COLUMN 6

Line 7, "ttifluo-" should read --trifluo---.

UNITED STATES PATENT AND TRADEMARK OFFICE
CERTIFICATE OF CORRECTION

PATENT NO. : 5,302,602

DATED : April 12, 1994

INVENTORS : ETSUO OSHIMA ET AL.

It is certified that error appears in the above-identified patent and that said Letters Patent is hereby corrected as shown below:

COLUMN 7

Line 14, "Moreover" should read --Moreover,--.
Line 39, "step." should read --step:--.

COLUMN 8

Line 4, "p-toi-" should read --p-tol--.
Line 5, "theisame" should read --the same--.

COLUMN 11

Line 30, "slide" shold read --ylide--.

COLUMN 13

Line 2, "use" should read --used--.
Line 22, "to a" should read --to the--.

COLUMN 14

Line 24, "preferred" should read --performed--.
Line 43, "$G_B$, z," should read --$G^B$, Z,--.

COLUMN 15

Line 39, "Further" should read --Further,--.
Line 65, "Further" should read --Further,--.

UNITED STATES PATENT AND TRADEMARK OFFICE
CERTIFICATE OF CORRECTION

PATENT NO. : 5,302,602

DATED : April 12, 1994

INVENTORS: ETSUO OSHIMA ET AL.

It is certified that error appears in the above-identified patent and that said Letters Patent is hereby corrected as shown below:

COLUMN 16

Line 68, "(p-nitroplienyl" should read --(p-nitrophenyl-- and "N-hvdroxysuc-" should read --N-hydroxysuc---.

COLUMN 18

Line 35, "$R_{A2}$," should read --$R^{A2}$,--.

COLUMN 19

Line 13, "$CH_{2OR}10$" should read --$CH_2OR^{10}$--.

COLUMN 41

Line 35, "possesses" should read --exhibit--.

COLUMN 43

Line 42, "platelets" should read --platelets,--.
Line 59, "and" should read --and the--.

COLUMN 44

Line 12, "diphtberia-" should read --diphtheria--.
Line 45, "rate-of" should read --rate of--.

UNITED STATES PATENT AND TRADEMARK OFFICE
CERTIFICATE OF CORRECTION

PATENT NO. : 5,302,602

DATED : April 12, 1994

INVENTORS : ETSUO OSHIMA ET AL.

It is certified that error appears in the above-identified patent and that said Letters Patent is hereby corrected as shown below:

COLUMN 45

Line 29, "represents" should read --represent--.

COLUMN 47

Line 5, "chang et al." should read --Chang et al.--.
Line 43, "tics)." should read --ticals).--.
Line 64, "as" should read --as a--.

COLUMN 48

Line 31, "administration, oral" should read --administration. Oral--.
Line 35, "intravenfus route etc.,," should read --intravenous routes, etc. are mentioned.--.
Line 36, "administration" should read --administration,--.
Line 47, "pepper" should read --pepper- --.

COLUMN 50

Line 2, "YR)i" should be deleted.
Line 6, "propertier" should read --properties--.

COLUMN 51

Line 50, "at-room" should read --at room--.

UNITED STATES PATENT AND TRADEMARK OFFICE
CERTIFICATE OF CORRECTION

PATENT NO. : 5,302,602

DATED : April 12, 1994

INVENTORS : ETSUO OSHIMA ET AL.

It is certified that error appears in the above-identified patent and that said Letters Patent is hereby corrected as shown below:

COLUMN 54

Line 20, "2-yllpropionate" should read --2-yl]propionate--.
Line 38, "2-mercap" should read --2-mercaptoethanol--.
Line 39, "for" should read --for an--.

COLUMN 57

Line 55, "7.02(s, 111)," should read --7.02(s,1H),--.
Line 68, "3.83(s, 111)," should read --3.83(s,H),--.

COLUMN 58

Line 27, "1 k" should read --1 l--.
Line 31, "hydorus" should read --hydrous--.
Line 44, "and" should read --under--.

COLUMN 59

Line 32, "6,L3f" should read --off--.

COLUMN 62

Line 2, "piperldine" should read --piperidine--.

COLUMN 65

Line 27, "precared" should read --prepared--.

UNITED STATES PATENT AND TRADEMARK OFFICE
CERTIFICATE OF CORRECTION

PATENT NO. : 5,302,602

DATED : April 12, 1994

INVENTORS : ETSUO OSHIMA ET AL.

It is certified that error appears in the above-identified patent and that said Letters Patent is hereby corrected as shown below:

COLUMN 66

Line 25, "piperidino[ethyl]" should read --piperidino]ethyl]--.
Line 27, "iso-propanol" should read --isopropanol--.

COLUMN 71

Line 62, "sodi=chlo-" should read --sodium-chlo- --.

COLUMN 76, TABLE 7-4

Example No. 54, under "NMR"; "6.80(d,J=12.9H," should read --6.80(d,J=12.9Hz,--.

COLUMN 78

Line 17, "dihydro -dibenz" should read --dihydrodibenz--.
Line 23, ""dehydrate" should read --dihydrate--.
Line 28, "iso -propanol." should read --isopropanol--.

UNITED STATES PATENT AND TRADEMARK OFFICE
CERTIFICATE OF CORRECTION

PATENT NO. : 5,302,602

DATED : April 12, 1994

INVENTORS : ETSUO OSHIMA ET AL.

It is certified that error appears in the above-identified patent and that said Letters Patent is hereby corrected as shown below:

COLUMN 80

Line 44, "represents" should read --represents $-COOR^3$ wherein $R^3$ represents hydrogen or lower alkyl,--.

UNITED STATES PATENT AND TRADEMARK OFFICE
CERTIFICATE OF CORRECTION

PATENT NO. : 5,302,602

DATED : April 12, 1994

INVENTORS : ETSUO OSHIMA ET AL.

It is certified that error appears in the above-identified patent and that said Letters Patent is hereby corrected as shown below:

COLUMN 80

Form (I), " 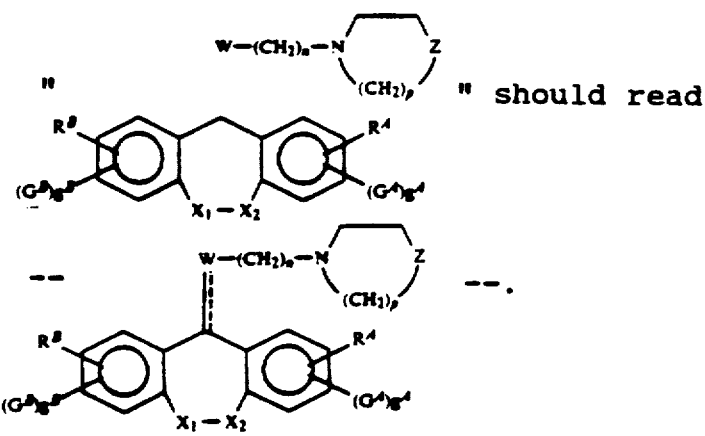 " should read

-- -- .

Signed and Sealed this

Twenty-third Day of May, 1995

Attest:

BRUCE LEHMAN

Attesting Officer

Commissioner of Patents and Trademarks